United States Patent
Cifter et al.

(10) Patent No.: US 10,105,316 B2
(45) Date of Patent: *Oct. 23, 2018

(54) INHALATION COMPOSITIONS COMPRISING MUSCARINIC RECEPTOR ANTAGONIST

(71) Applicant: Arven Ilac Sanayi Ve Ticaret A.S., Istanbul (TR)

(72) Inventors: Ümit Cifter, Istanbul (TR); Ali Turkyilmaz, Istanbul (TR); Onur Mutlu, Istanbul (TR)

(73) Assignee: Arven Ilac Sanayi ve Ticaret A.S., Istanbul (TR)

( * ) Notice: Subject to any disclaimer, the term of this patent is extended or adjusted under 35 U.S.C. 154(b) by 0 days.

This patent is subject to a terminal disclaimer.

(21) Appl. No.: 14/412,595

(22) PCT Filed: Jun. 27, 2013

(86) PCT No.: PCT/TR2013/000198
§ 371 (c)(1),
(2) Date: Jan. 2, 2015

(87) PCT Pub. No.: WO2014/007771
PCT Pub. Date: Jan. 9, 2014

(65) Prior Publication Data
US 2015/0157567 A1    Jun. 11, 2015

(30) Foreign Application Priority Data

| Jul. 5, 2012 | (TR) | 2012/07842 |
| Sep. 12, 2012 | (TR) | 2012/10438 |
| Oct. 2, 2012 | (TR) | 2012/11213 |
| Jun. 18, 2013 | (TR) | 2013/07336 |

(51) Int. Cl.
| A61K 9/14 | (2006.01) |
| A61K 9/48 | (2006.01) |
| B65D 83/06 | (2006.01) |
| A61K 31/56 | (2006.01) |
| A61K 31/535 | (2006.01) |
| A61K 31/44 | (2006.01) |
| A61K 31/40 | (2006.01) |
| A61K 9/00 | (2006.01) |
| A61K 45/06 | (2006.01) |
| A61K 31/137 | (2006.01) |
| A61K 31/138 | (2006.01) |
| A61K 31/167 | (2006.01) |
| A61K 31/27 | (2006.01) |
| A61K 31/439 | (2006.01) |
| A61K 31/4704 | (2006.01) |
| A61K 31/538 | (2006.01) |
| A61K 31/573 | (2006.01) |
| A61M 15/00 | (2006.01) |
| A61K 9/16 | (2006.01) |
| A61K 31/24 | (2006.01) |
| A61K 31/46 | (2006.01) |
| A61K 31/569 | (2006.01) |
| A61K 31/58 | (2006.01) |

(52) U.S. Cl.
CPC .......... *A61K 9/0075* (2013.01); *A61K 9/1623* (2013.01); *A61K 31/137* (2013.01); *A61K 31/138* (2013.01); *A61K 31/167* (2013.01); *A61K 31/24* (2013.01); *A61K 31/27* (2013.01); *A61K 31/40* (2013.01); *A61K 31/439* (2013.01); *A61K 31/44* (2013.01); *A61K 31/46* (2013.01); *A61K 31/4704* (2013.01); *A61K 31/538* (2013.01); *A61K 31/569* (2013.01); *A61K 31/573* (2013.01); *A61K 31/58* (2013.01); *A61K 45/06* (2013.01); *A61M 15/003* (2014.02); *A61M 15/0025* (2014.02); *A61M 15/0045* (2013.01); *A61M 2202/064* (2013.01); *A61M 2205/19* (2013.01)

(58) Field of Classification Search
None
See application file for complete search history.

(56) References Cited

U.S. PATENT DOCUMENTS

| 2,956,062 | A | 10/1960 | Lunsford et al. |
| 3,472,861 | A | 10/1969 | Zeile et al. |
| 3,505,337 | A | 4/1970 | Zeile et al. |
| 3,634,582 | A | 1/1972 | Hartley et al. |
| 3,929,768 | A | 12/1975 | Brattsand et al. |
| 4,335,121 | A | 6/1982 | Phillipps et al. |
| 4,817,551 | A | 4/1989 | Matson |
| 5,478,578 | A | 12/1995 | Arnold et al. |
| 5,482,934 | A | 1/1996 | Calatayud et al. |
| 5,990,793 | A | 11/1999 | Bieback |

(Continued)

FOREIGN PATENT DOCUMENTS

| EP | 0 057 401 | 8/1982 |
| EP | 4 187 16 | 9/1990 |

(Continued)

OTHER PUBLICATIONS

U.S. Appl. No. 14/412,592, Cifter et al.

(Continued)

*Primary Examiner* — Jeffrey T. Palenik
(74) *Attorney, Agent, or Firm* — Liang, Frank & King LLP

(57) ABSTRACT

The invention relates to pharmaceutical powder compositions administered by means of inhalers. More particularly, it relates to pharmaceutical powder compositions having the content uniformity and the desired stability used in inhaler devices.

47 Claims, No Drawings

(56) References Cited

U.S. PATENT DOCUMENTS

| | | |
|---|---|---|
| 5,993,805 A | 11/1999 | Sutton et al. |
| 6,598,603 B1 | 7/2003 | Andersson et al. |
| 6,645,466 B1 | 11/2003 | Keller et al. |
| 2002/0055494 A1 | 5/2002 | Hassan |
| 2002/0110529 A1 | 8/2002 | Bechtold-Peters |
| 2002/0142049 A1 | 10/2002 | Lee |
| 2003/0007932 A1 | 1/2003 | Bechtold-Peters |
| 2003/0018019 A1 | 1/2003 | Meade |
| 2003/0070679 A1 | 4/2003 | Hochrainer |
| 2004/0009963 A1 | 1/2004 | Horstman et al. |
| 2004/0025876 A1 | 2/2004 | Miller et al. |
| 2004/0241232 A1 | 12/2004 | Brown et al. |
| 2005/0121027 A1* | 6/2005 | Nilsson ................ A61K 9/0075 128/200.23 |
| 2005/0186146 A1 | 8/2005 | Gong et al. |
| 2005/0211244 A1 | 9/2005 | Nilsson et al. |
| 2006/0102511 A1 | 5/2006 | Pasbrig |
| 2007/0071691 A1 | 3/2007 | Brown |
| 2008/0057003 A1 | 3/2008 | Bechtold-Peters et al. |
| 2009/0076397 A1 | 3/2009 | Libbus et al. |
| 2009/0188498 A1 | 7/2009 | Thoemmes et al. |
| 2009/0209502 A1 | 8/2009 | Haeberlin et al. |
| 2009/0322513 A1 | 12/2009 | Hwang et al. |
| 2010/0055192 A1 | 3/2010 | Musa et al. |
| 2011/0105449 A1 | 5/2011 | Trofast |
| 2011/0156915 A1 | 6/2011 | Brauers et al. |
| 2012/0123277 A1 | 5/2012 | Blaha et al. |
| 2015/0157567 A1 | 6/2015 | Cifter et al. |
| 2015/0165036 A1 | 6/2015 | Cifter et al. |
| 2015/0165037 A1 | 6/2015 | Turkyilmaz et al. |
| 2015/0165038 A1 | 6/2015 | Cifter et al. |
| 2015/0173654 A1 | 6/2015 | Belanger et al. |
| 2015/0174064 A1 | 6/2015 | Cifter et al. |
| 2015/0224197 A1 | 8/2015 | Cifter et al. |
| 2016/0094700 A1 | 3/2016 | Lee et al. |
| 2016/0119424 A1 | 4/2016 | Kane et al. |
| 2016/0322078 A1 | 11/2016 | Bose et al. |

FOREIGN PATENT DOCUMENTS

| | | |
|---|---|---|
| EP | 1 124 544 B1 | 8/2001 |
| EP | 1 894 568 A1 | 3/2008 |
| EP | 1944018 A1 | 7/2008 |
| EP | 1 968 548 | 9/2008 |
| EP | 2080508 A1 | 7/2009 |
| EP | 2 100 599 A1 | 9/2009 |
| EP | 2191821 A1 | 6/2010 |
| GB | 2434098 | 7/2007 |
| WO | WO 95/31964 | 11/1995 |
| WO | WO 00/27373 | 5/2000 |
| WO | WO 00/33789 | 6/2000 |
| WO | WO 01/78693 A2 | 10/2001 |
| WO | WO 2004/069225 | 8/2004 |
| WO | WO-2005/044187 A2 | 5/2005 |
| WO | WO 2005/097126 A1 | 10/2005 |
| WO | WO 2006/086270 A1 | 8/2006 |
| WO | WO 2007/064912 | 6/2007 |
| WO | WO 2007135409 A1 | 11/2007 |
| WO | WO-2008/000482 A1 | 1/2008 |
| WO | WO-2008/066810 A2 | 6/2008 |
| WO | WO-2008/101591 A1 | 8/2008 |
| WO | WO 2010/144628 A2 | 2/2010 |
| WO | WO-2010/144628 A2 | 12/2010 |
| WO | WO-2011/048379 A2 | 4/2011 |
| WO | WO-2011/076841 A2 | 6/2011 |
| WO | WO 2011/076841 A2 | 6/2011 |
| WO | WO-2011/093815 A2 | 8/2011 |
| WO | WO-2011/093817 A1 | 8/2011 |
| WO | WO-2011/093819 A2 | 8/2011 |
| WO | 2011105975 A1 | 9/2011 |
| WO | WO-2011/145109 A1 | 11/2011 |
| WO | WO 2011/145109 A1 | 11/2011 |
| WO | WO 2012/030308 A2 | 3/2012 |
| WO | WO 2012/030664 A1 | 3/2012 |
| WO | WO-2012/050945 A1 | 4/2012 |
| WO | WO 2012/050945 A1 | 4/2012 |
| WO | WO-2012/106575 A1 | 8/2012 |
| WO | WO-2014/007769 A1 | 1/2014 |
| WO | WO-2014/007770 A2 | 1/2014 |
| WO | WO-2014/007771 A2 | 1/2014 |
| WO | WO-2014/007772 A2 | 1/2014 |
| WO | WO-2014/007773 A1 | 1/2014 |
| WO | WO-2014/007781 A2 | 1/2014 |

OTHER PUBLICATIONS

U.S. Appl. No. 14/412,609, Cifter et al.
U.S. Appl. No. 14/412,617, Cifter et al.
U.S. Appl. No. 14/412,618, Turkyilmaz et al.
U.S. Appl. No. 14/412,632, Cifter et al.
International Search Report and Written Opinion for PCT/TR2013/000212, dated Jan. 27, 2014 (9 pages).
International Search Report and Written Opinion for PCT Application No. PCT/TR2013/000196, dated Dec. 9, 2013 (10 pages).
International Search Report and Written Opinion for PCT Application No. PCT/TR2013/000197, dated Feb. 5, 2014 (9 pages).
International Search Report and Written Opinion for PCT Application No. PCT/TR2013/000199, dated Jan. 31, 2014 (9 pages).
International Search Report and Written Opinion for PCT Application No. PCT/TR2013/000200, dated Dec. 9, 2013 (10 pages).
Search Report and Written Opinion for Turkish Patent Application No. 201207842, completed May 2, 2013 (8 pages).
Search Report and Written Opinion for Turkish Patent Application No. 201210438, completed Jan. 16, 2014 (7 pages).
Search Report and Written Opinion for Turkish Patent Application No. 201307336, completed Dec. 10, 2013 (9 pages).
Search Report and Written Opinion for Turkish Patent Application No. 201307349, completed Jan. 28, 2014 (7 pages).
Tee et al., "The use of different sugars as fine and coarse carriers for aerosolisded salbutamol sulphate," *International Journal of Pharmaceutics*, 208:111-123, 2000.
International Search Report and Written Opinion for PCT/TR2013/000198, dated Jan. 27, 2014 (9 pages).
Search Report and Written Opinion for Turkish Patent Application No. 201307351, completed Apr. 22, 2014 (8 pages).
Non-final Rejection issued in U.S. Appl. No. 14/412,609 dated Aug. 26, 2016.
Final Office Action issued in U.S. Appl. No. 14/412,609 dated Mar. 6, 2017.
Non-final Rejection issued in U.S. Appl. No. 14/412,952 dated Jun. 9, 2017.
Non-final Rejection issued in U.S. Appl. No. 12/412,595 dated May 12, 2017.
Final Office Action issued in U.S. Appl. No. 14/412,595 dated Sep. 13, 2016.
Final Office Action issued in U.S. Appl. No. 14/412,617 dated Aug. 1, 2016.
Non-final Rejection issued in U.S. Appl. No. 14/412,632 dated May 11, 2017.
International Search Report for Int'l Appl. No. PCt/TR2013/000191, dated Oct. 28, 1013, dated Oct. 28, 2013.
International Search Report for Int'l Appl. No. PCt/TR2013/000192, dated Oct. 22, 1013, dated Oct. 22, 2013.
Non-final rejection issued in U.S. Appl. No. 12/412,083, dated Jul. 17, 2017.
Final Office Action issued in U.S. Appl. No. 12/412,083, dated Aug. 8, 2016.
Non-final rejection issued in U.S. Appl. No. 12/412,083, dated Apr. 27, 2016.
Non-final rejection issued in U.S. Appl. No. 14/412,066, dated Jun. 26, 2017.
Final Office Action issued in U.S. Appl. No. 14/412,066, dated Sep. 15, 2016.
Non-final rejection issued in U.S. Appl. No. 14/412,066, dated Apr. 13, 2016.
Non-final rejection issued in U.S. Appl. No. 15/088,492, dated May 16, 2017.

(56) References Cited

OTHER PUBLICATIONS

Non-final rejection issued in U.S. Appl. No. 14/412,595, dated Mar. 3, 2016.
Non-final rejection issued in U.S. Appl. No. 14/412,632, dated Aug. 28, 2017.
Nokhodchi et al., "An Investigation into Alternative Sugars as Potential Carriers for a Dry Powder Formulation of Budesonide and Formoterol," Biomedicine International, 2:43-54, 2011.
Machine English language translation of document EP 4 187 16, Pub'd Mar. 27, 1991.
Cazzola et al (2007), Pulmonary Pharmacology & Therapeutics, vol. 20, pp. 556-561.

\* cited by examiner

INHALATION COMPOSITIONS COMPRISING MUSCARINIC RECEPTOR ANTAGONIST

TECHNICAL FIELD

The invention relates to pharmaceutical powder compositions administered by means of inhaler devices. More particularly, it relates to pharmaceutical powder compositions having the content uniformity and the desired stability used in inhaler devices.

BACKGROUND OF THE INVENTION

Tiotropium bromide anticholinergic bronchodilator used in the management of chronic obstructive pulmonary disease (COPD). Chemical name thereof is (1R,2R,4S,5S,7s)-7-[2-Hydroxy-2,2-di(2-thienyl)acetoxy]-9,9-dimethyl-3-oxa-9 azoniatricyclo[3.3.1.02,4]nonane bromide and its chemical formula is as shown in formula I:

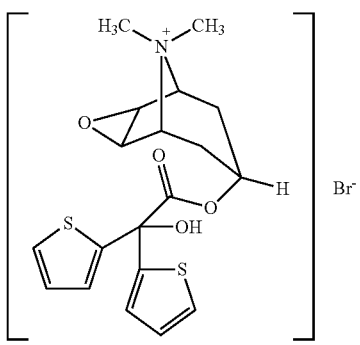

Formula I

Tiotropium molecule was first disclosed in the EP418716.

Ipratropium bromide is an anticholinergic bronchodilator used for the treatment of chronic obstructive pulmonary disease and acute asthma. Its chemical name is (1R,3r,5S-,8r)-8-Isopropyl-3-((+/−)-tropoyloxy)tropanium bromide. Chemical structure thereof is as shown in formula 2.

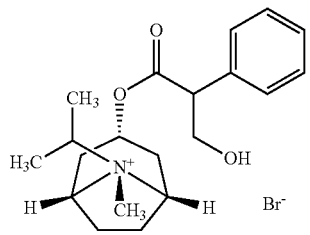

Formula 2

U.S. Pat. No. 3,505,337 is the first patent to disclose ipratropium molecule.

Glycopyrronium bromide is an anticholinergic. Its chemical name is 3-(alpha-Cyclopentylmandeloyloxy)-1,1-dimethylpyrrolidinium bromide. Chemical structure thereof is as shown in formula 3.

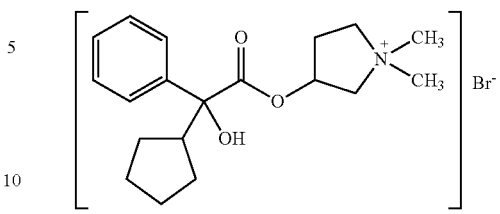

Formula 3

Glycopyrronium molecule was first disclosed in the U.S. Pat. No. 2,956,062.

Oxitropium bromide is an anticholinergic drug. Chemical name thereof is (8r)-6beta,7beta-Epoxy-8-ethyl-3alpha-hydroxy-1alphaH,5alphaH-tropanium bromide (−)-tropate. Chemical structure thereof is as shown in formula 4.

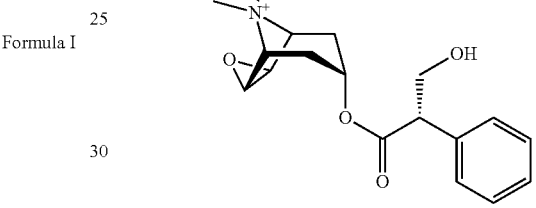

Formula 4

Oxitropium molecule was first disclosed in the U.S. Pat. No. 3,472,861

Aclidinium bromide is a muscarinic antagonist. Chemical name thereof is [(3R)-1-(3-phenoxypropyl)-1-azoniabicyclo[2.2.2]octan-3-yl]2-hydroxy-2,2-dithiophen-2 ylacetate;bromide. Chemical structure thereof is as shown in formula 5.

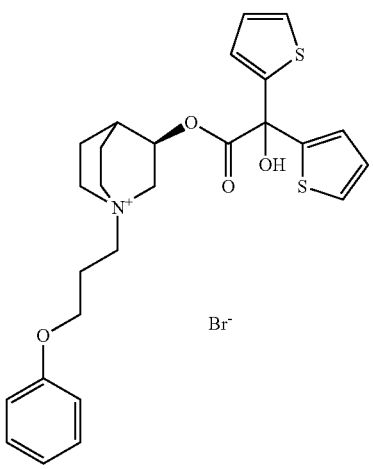

Formula 5

Daratropium is a muscarinic antagonist used in the management of chronic obstructive pulmonary disease (COPD). Chemical name thereof is 3-[(1R,5S)-8,8-dimethyl-8-azoniabicyclo[3.2.1]octan-3-yl]-2,2-diphenylpropanenitrile;bromide. Chemical structure thereof is as shown in formula 6.

Formula 6

Inhalation compositions show activity by reaching directly to the respiratory system. Contriving the compositions is based on containing the active ingredient along with the carrier and the extender having the particle sizes capable of carrying said active ingredient to the respiratory system. On the other hand, carrier particle size enabling conveying the active ingredient to the respiratory system in the desired levels is also critical. Flowing and filling of the components constituting the composition also depend on the particle size and the ratios in-between are determined accordingly. Said ratio to be in desired levels is substantially critical and the filling process rate and the amount of the formulation to be filled depend on this. Achieving the homogeneous mixture and carrying out filling of said mixture economically and in an advantageous manner in terms of process rate is a preferred condition.

It is a pre-condition for the medicament to possess content uniformity, in terms of user safety and effectiveness of the treatment. Difference of the particle sizes between the carrier and the extender used is important in order to ensure the content uniformity. This difference to be beyond measure hampers to achieve the desired content uniformity. Another potential problem is to be unable to achieve the dosage accuracy present in each cavity or capsule. And this is of vital importance in terms of effectiveness of the treatment.

In order to meet all these requirements, dry powder inhalers (DPI) should meet a series of criteria taking particularly into account the following circumstances:

Content Uniformity of the Active Drug:

Each capsule or blister should contain same amount of drug in the single dose system. Whereas in a multi-dose system, same amount of drug must be released in each application in order to ensure that the patient administers the same dosage in each time. Presence of the carrier should support the content uniformity even in a low dose drug.

Fluidity:

Design of the device, characteristics of the active ingredient and the filling platform to be used define the required properties of the carrier needed. Formulation flow characteristics have importance in terms of ensuring that the device carries out all the functions properly and provides a continuous performance. Choosing the carrier is of high importance in that it ensures that the device functions properly and carries accurate amount of active ingredient to the patient. Therefore it is quite important to employ mannitol as the carrier, in two different particle sizes (fine and coarse).

Dose Consistency:

In order that all of the doses coming out of the device contain accurate amount of active ingredient, dry powder inhaler (DPI) devices should exhibit consistent dose uniformity.

Irrespective of the inhalation capability of a patient, it is of substantial importance that the dose released from the dry powder inhaler device to be same in each time. For this reason, employing mannitol as a carrier possessing proper characteristics in the formulation assists the dose to be administered consistently.

Small drug particles are likely to agglomerate. Said coagulation can be prevented by employing suitable carrier or carrier mixtures. It also assists in controlling the fluidity of the drug coming out of the carrier device and ensuring that the active ingredient reaching to lungs is accurate and consistent.

In addition to this, the mixture of the drug particles adhered to the carrier should be homogeneous. Adhesion should be quite strong as the drug could not detach from the carrier particle. Moreover, lower doses of powder should also be filled into the device and the drug should always be released in the same way. One of the main parameters for the formulation is the particle size. Therefore, it has been found to be very important to employ the fine (small) and coarse (large) particles of the selected carrier in the formulations of the present invention in an accurate ratio.

In order to meet all these requirements, dry powder inhaler (DPI) formulations should be adapted especially by carefully choosing the employed carriers. In order to meet these requirements, the inhalable, fine or micro-fine particles of the active compounds are mixed with carriers. By means of mixing process, particle size of the carrier can be changed in order that a certain amount thereof to become inhalable. Particle size of employed carrier depends on the requirements and specifications of the powder inhaler used for application of the formulation. In this mixture, no dissociation should occur during all of the required procedures, transportation, and storage and dosing, i.e., active compound should not dissociate from its carrying particles. However, during the dissociation in the inhaler induced by inhalation of the patient, active compound particles should dissociate as effective as possible, i.e., as much as possible.

Furthermore, in the active ingredients administered via inhalation, one encounters certain stability related problems due to environmental and physical conditions. Mentioned active substances are influenced substantially by the temperature, air and humidity conditions. Exposure to air and moisture causes structural destruction of said active substances and leads them to build up a change in chemical behavior. Stability of the developed products is not in desired levels and shelf-life thereof are getting shorter. In addition, these active substances may react with auxiliary substances used along with them in the step of developing formulation. This, on the other hand, leads to impurities in the formulations and undesired compositions to get involved in the formulations. It is of critical importance for the formulation, to employ auxiliary substances and method not bringing along to mentioned problems. Moisture and air content of the active ingredients kept in the blister or capsule may be determinative for the stability. That is, the air and the moisture content within the closed blister and capsule, is quite important for these kinds of pharmaceutical forms.

For this reason, there is still a need for the carriers capable of overcoming aforementioned problems, problems related to interaction between active ingredient and carrier and moreover, problems related to pulmonary application of the drugs. Present inventions makes it possible as well, to obtain different compositions and compositions of combinations having satisfactory characteristics in a safe and effective manner, in terms of increasing the drug storing for pulmonary application or increasing the drug release rates.

As a result, there is a need for a novelty in the field relating to the compositions administrable by the patients suffering from chronic obstructive pulmonary disease or asthma.

OBJECT AND BRIEF DESCRIPTION OF THE INVENTION

Present invention relates to easily applicable inhalation compositions overcoming all of the aforementioned problems and bringing further advantages to the technical field.

Starting out from the state of the art, main object of the invention is to obtain effective and stable composition applicable in chronic obstructive pulmonary disease and asthma.

Another object of the invention is to enable a composition in which the desired filling rate and content uniformity is achieved.

Still other object of the invention is to obtain inhalation compositions having appropriate particle size and ratios ensuring to facilitate filling process into the blister package or the capsule, and enabling on the other hand to realize a homogeneous mixture.

Dry powder inhalation compositions are developed with the intent of achieving aforementioned purposes and all of the objectives that might come up from the detailed description below.

In a preferred embodiment of the invention, novelty is achieved by,
- at least one muscarinic receptor antagonist or a pharmaceutically acceptable salt thereof,
- fine particle lactose in the ratio of 1-20% by weight of said composition and having (d50) particle size in the range of 4-10 μm and coarse particle mannitol in the ratio of 80-99% by weight of said composition and having (d50) particle size in the range of 50-120 μm.

In a preferred embodiment of the invention, (d50) particle size of said fine particle lactose is preferably 4-7 μm.

In a preferred embodiment of the invention, particle size of said fine particle lactose (d10) is 1-5 μm, preferably 1-4 μm.

In a preferred embodiment of the invention, particle size of said fine particle lactose (d90) is 7-20 μm, preferably 7-15 μm.

In a preferred embodiment of the invention, (d50) particle size of said coarse particle mannitol is preferably 50-75 μm.

In a preferred embodiment of the invention, particle size of said coarse particle mannitol (d10) is preferably 10-50 μm.

In a preferred embodiment of the invention, particle size of said coarse particle mannitol (d90) is 120-300 μm, preferably 75-250 μm.

A preferred embodiment of the invention further comprises coarse particle lactose of (d50) particle size of 50-80 μm, preferably of 50-75 μm.

A preferred embodiment of the invention further comprises coarse particle lactose (d10) having particle size of 10-50 μm.

A preferred embodiment of the invention further comprises coarse particle lactose (d90) having particle size of 120-300 μm, preferably of 75-250 μm.

A preferred embodiment of the invention further comprises fine particle mannitol of (d50) particle size of 4-7 μm.

A preferred embodiment of the invention further comprises fine particle mannitol (d10) having particle size of 1-5 μm, preferably of 1-4 μm.

A preferred embodiment of the invention further comprises fine particle mannitol (d90) having particle size of 10-20 μm, preferably of 7-10 μm.

In a preferred embodiment of the invention, said lactose amount is preferably in the range of 1-15%, more preferably 1-10% by weight.

In a preferred embodiment of the invention, said mannitol amount is preferably in the range of 85-99%, more preferably 90-99% by weight of the composition.

In another preferred embodiment of the invention, said muscarinic receptor antagonist is selected from the group consisting of at least one or a mixture of tiotropium, glycopyronium, aclidinium, darotropium and ipratropium.

In another preferred embodiment of the invention, said retard muscarinic receptor antagonist is tiotropium.

In another preferred embodiment of the invention, said retard muscarinic receptor antagonist is glycopyronium.

In another preferred embodiment of the invention, said retard muscarinic receptor antagonist is aclinidium.

In another preferred embodiment of the invention, said retard muscarinic receptor antagonist is oxitropium.

In another preferred embodiment of the invention, said retard muscarinic receptor antagonist is ipratropium.

In another preferred embodiment of the invention, said retard muscarinic receptor antagonist is darotropium.

Another preferred embodiment of the invention further comprises one or a combination of two or more selected from corticosteroid and β2-adrenergic agonist.

In a preferred embodiment of the invention, said corticosteroid is selected from the group consisting of at least one or a mixture of ciclesonide, budesonide, fluticasone, aldosterone, beklometazone, betametazone, chloprednol, cortisone, cortivasole, deoxycortone, desonide, desoxymetasone, dexametasone, difluorocortolone, fluchlorolone, flumetasone, flunisolide, fluquinolone, fluquinonide, flurocortisone, fluorocortolone, flurometolone, flurandrenolone, halcynonide, hydrocortisone, icometasone, meprednisone, methylprednisolone, mometasone, paramethasone, prednisolone, prednisone, tixocortole, triamcynolondane, or is a combination thereof.

In a preferred embodiment of the invention, said corticosteroid is ciclesonide.

In another preferred embodiment of the invention, said corticosteroid is budesonide.

In another preferred embodiment of the invention, said corticosteroid is fluticasone.

In another preferred embodiment of the invention, said corticosteroid is mometasone.

In a preferred embodiment of the invention, said beta-2 adrenergic agonist is selected from the group consisting of at least one or a mixture of salmeterol, ormoterol, arformoterol, salbutamol, indacaterol, terbutaline, metaproterenol, vilanterol, carmoterol, olodaterol, bambuterol, clenbuterol.

In another preferred embodiment of the invention, said beta-2 adrenergic agonist is salmeterol.

In another preferred embodiment of the invention, said beta-2 adrenergic agonist is formoterol.

In another preferred embodiment of the invention, said beta-2 adrenergic agonist is arfomoterol.

In another preferred embodiment of the invention, said beta-2 adrenergic agonist is salbutomol.

In another preferred embodiment of the invention, said beta-2 adrenergic agonist is bambuterol.

In another preferred embodiment of the invention, said beta-2 adrenergic agonist is carmoterol.

In another preferred embodiment of the invention, said beta-2 adrenergic agonist is olodaterol.

In another preferred embodiment of the invention, said beta-2 adrenergic agonist is vilanterol.

In another preferred embodiment of the invention, said beta-2 adrenergic agonist is indacaterol.

In another preferred embodiment of the invention, said composition comprises muscarinic receptor antagonist and corticosteroid.

In another preferred embodiment of the invention, said composition comprises beta-2 adrenergic agonist and muscarinic antagonist.

In another preferred embodiment of the invention, said composition comprises corticosteroid, β2-adrenergic agonist and muscarinic receptor antagonist.

Another preferred embodiment of the invention further comprises one of or a mixture of the excipients from glucose, glucose anhydrous, trehalose, cellobiose.

In another preferred embodiment of the invention, said composition comprises one of the following therapeutically active combinations:
i. Aclidinium ve tiotropium
ii. Aclidinium ve glycopyrronium
iii. Aclidinium ve darotropyum
iv. Aclidinium ve oxitropium
v. Aclidinium ve ipratropium
vi. Aclidinium ve ciclesonide
vii. Aclidinium ve budesonid
viii. Aclidinium ve fluticasone
ix. Aclidinium ve mometazon
x. Tiotropium ve glycopyrronium
xi. Tiotropium ve darotropyum
xii. Tiotropium ve oxitropium
xiii. Tiotropium ve ipratropium
xiv. Tiotropium ve ciclesonide
xv. Tiotropium ve budesonid
xvi. Tiotropium ve fluticasone
xvii. Tiotropium ve mometazon
xviii. Glycopyrronium ve tiotropium
xix. Glycopyrronium ve glycopyrronium
xx. Glycopyrronium ve darotropyum
xxi. Glycopyrronium ve oxitropium
xxii. Glycopyrronium ve ipratropium
xxiii. Glycopyrronium ve ciclesonide
xxiv. Glycopyrronium ve budesonid
xxv. Glycopyrronium ve fluticasone
xxvi. Glycopyrronium ve mometazon
xxvii. Oxitropium ve tiotropium
xxviii. Oxitropium ve darotropyum
xxix. Oxitropium ve aclidinium
xxx. Oxitropium ve ipratropium
xxxi. Oxitropium ve ciclesonide
xxxii. Oxitropium ve budesonid
xxxiii. Oxitropium ve fluticasone
xxxiv. Oxitropium ve mometazon
xxxv. Darotropyum ve tiotropium
xxxvi. Darotropyum ve aclidinium
xxxvii. Darotropyum ve oxitropium
xxxviii. Darotropyum ve ipratropium
xxxix. Darotropyum ve ciclesonide
xl. Darotropyum ve budesonid
xli. Darotropyum ve fluticasone
xlii. Darotropyum ve mometazon
wherein the above therapeutic agents can be present as a pharmaceutically acceptable salt or ester thereof, or in enantiomerically pure form or as a racemic mixture.

In another preferred embodiment of the invention, said composition comprises one of the following therapeutically active combinations:
i. Aclidinium ve salmeterol
ii. Aclidinium ve formoterol
iii. Aclidinium ve arformoterol
iv. Aclidinium ve salbutamol
v. Aclidinium ve indacaterol
vi. Aclidinium ve vilanterol
vii. Aclidinium ve carmoterol
viii. Aclidinium ve olodaterol
ix. Aclidinium ve bambuterol
x. Tiotropium ve salmeterol
xi. Tiotropium ve formoterol
xii. Tiotropium ve arformoterol
xiii. Tiotropium ve salbutamol
xiv. Tiotropium ve indacaterol
xv. Tiotropium ve vilanterol
xvi. Tiotropium ve carmoterol
xvii. Tiotropium ve olodaterol
xviii. Tiotropium ve bambuterol
xix. Glycopyrronium ve salmeterol
xx. Glycopyrronium ve formoterol
xxi. Glycopyrronium ve arformoterol
xxii. Glycopyrronium ve salbutamol
xxiii. Glycopyrronium ve indacaterol
xxiv. Glycopyrronium ve vilanterol
xxv. Glycopyrronium ve carmoterol
xxvi. Glycopyrronium ve olodaterol
xxvii. Glycopyrronium ve bambuterol
xxviii. Oxitropium ve salmeterol
xxix. Oxitropium ve formoterol
xxx. Oxitropium ve arformoterol
xxxi. Oxitropium ve salbutamol
xxxii. Oxitropium ve indacaterol
xxxiii. Oxitropium ve vilanterol
xxxiv. Oxitropium ve carmoterol
xxxv. Oxitropium ve olodaterol
xxxvi. Oxitropium ve bambuterol
xxxvii. Darotropium ve salmeterol
xxxviii. Darotropium ve formoterol
xxxix. Darotropium ve arformoterol
xl. Darotropium ve salbutamol
xli. Darotropium ve indacaterol
xlii. Darotropium ve vilanterol
xliii. Darotropium ve carmoterol
xliv. Darotropium ve olodaterol
xlv. Darotropium ve bambuterol
wherein the above therapeutic agents can be present as a pharmaceutically acceptable salt or ester thereof, or in enantiomerically pure form or as a racemic mixture.

In another preferred embodiment of the invention, said composition comprises one of the following therapeutically active combinations:
i. Aclidinium, tiotropium ve salmeterol
ii. Aclidinium, tiotropium ve formoterol
iii. Aclidinium, tiotropium ve arformoterol
iv. Aclidinium, tiotropium ve indacaterol
v. Aclidinium, tiotropium ve olodaterol
vi. Aclidinium, tiotropium ve vilanterol
vii. Aclidinium, tiotropium ve carmoterol
viii. Aclidinium, tiotropium ve bambuterol
ix. Aclidinium, glycopyrronium ve salmeterol
x. Aclidinium, glycopyrronium ve formoterol
xi. Aclidinium, glycopyrronium ve arformoterol
xii. Aclidinium, glycopyrronium ve indacaterol
xiii. Aclidinium, glycopyrronium ve olodaterol xiv. Aclidinium, glycopyrronium ve vilanterol
xv. Aclidinium, glycopyrronium ve carmoterol
xvi. Aclidinium, glycopyrronium ve bambuterol
xvii. Aclidinium, oxitropium ve salmeterol
xviii. Aclidinium, oxitropium ve formoterol
xix. Aclidinium, oxitropium ve arformoterol
xx. Aclidinium, oxitropium ve indacaterol
xxi. Aclidinium, oxitropium ve olodaterol
xxii. Aclidinium, oxitropium ve vilanterol
xxiii. Aclidinium, oxitropium ve carmoterol
xxiv. Aclidinium, oxitropium ve bambuterol
xxv. Glycopyrronium, tiotropium ve salmeterol
xxvi. Glycopyrronium, tiotropium ve formoterol
xxvii. Glycopyrronium, tiotropium ve arformoterol
xxviii. Glycopyrronium, tiotropium ve indacaterol
xxix. Glycopyrronium, tiotropium ve olodaterol
xxx. Glycopyrronium, tiotropium ve vilanterol
xxxi. Glycopyrronium, tiotropium ve carmoterol
xxxii. Glycopyrronium, tiotropium ve bambuterol
xxxiii. Glycopyrronium, oxitropium ve salmeterol
xxxiv. Glycopyrronium, oxitropium ve formoterol
xxxv. Glycopyrronium, oxitropium ve arformoterol
xxxvi. Glycopyrronium, oxitropium ve indacaterol
xxxvii. Glycopyrronium, oxitropium ve olodaterol
xxxviii. Glycopyrronium, oxitropium ve vilanterol
xxxix. Glycopyrronium, oxitropium ve carmoterol
xl. Glycopyrronium, oxitropium ve bambuterol
xli. Daratropium, tiotropium ve salmeterol
xlii. Daratropium, tiotropium ve formoterol
xliii. Daratropium, tiotropium ve arformoterol
xliv. Daratropium, tiotropium ve indacaterol
xlv. Daratropium, tiotropium ve olodaterol
xlvi. Daratropium, tiotropium ve vilanterol
xlvii. Daratropium, tiotropium ve carmoterol
xlviii. Daratropium, tiotropium ve bambuterol
xlix. Daratropium, glycopyrronium ve salmeterol
l. Daratropium, gikopironyum ve formoterol
li. Daratropium, glycopyrronium ve arformoterol
lii. Daratropium, glycopyrronium ve indacaterol
liii. Daratropium, glycopyrronium ve olodaterol
liv. Daratropium, glycopyrronium ve vilanterol
lv. Daratropium, glycopyrronium ve carmoterol
lvi. Daratropium, glycopyrronium ve bambuterol
lvii. Daratropium, aclidinium ve salmeterol
lviii. Daratropium, aclidinium ve formoterol
lix. Daratropium, aclidinium ve arformoterol
lx. Daratropium, aclidinium ve indacaterol
lxi. Daratropium, aclidinium ve olodaterol
lxii. Daratropium, aclidinium ve vilanterol
lxiii. Daratropium, aclidinium ve carmoterol
lxiv. Daratropium, aclidinium ve bambuterol
lxv. Daratropium, oxitropium ve salmeterol
lxvi. Daratropium, oxitropium ve formoterol
lxvii. Daratropium, oxitropium ve arformoterol
lxviii. Daratropium, oxitropium ve indacaterol
lxix. Daratropium, oxitropium ve olodaterol
lxx. Daratropium, oxitropium ve vilanterol
lxxi. Daratropium, oxitropium ve carmoterol
lxxii. Daratropium, oxitropium ve bambuterol
lxxiii. İndacaterol, tirotropiyum ve salmeterol
lxxiv. İndacaterol, tirotropiyum ve formoterol
lxxv. İndacaterol, tirotropiyum ve arformoterol
lxxvi. İndacaterol, tirotropiyum ve olodaterol
lxxvii. İndacaterol, tirotropiyum ve vilanterol
lxxviii. İndacaterol, tirotropiyum ve carmoterol
lxxix. İndacaterol, tirotropiyum ve bambuterol
lxxx. İndacaterol, glycopyrronium ve salmeterol
lxxxi. İndacaterol, glycopyrronium ve formoterol
lxxxii. İndacaterol, glycopyrronium ve arformoterol
lxxxiii. İndacaterol, glycopyrronium ve olodaterol
lxxxiv. İndacaterol, glycopyrronium ve vilanterol
lxxxv. İndacaterol, glycopyrronium ve carmoterol
lxxxvi. İndacaterol, glycopyrronium ve bambuterol
lxxxvii. İndacaterol, aclidinium ve salmeterol
lxxxviii. İndacaterol, aclidinium ve formoterol
lxxxix. İndacaterol, aclidinium ve arformoterol
xc. İndacaterol, aclidinium ve olodaterol
xci. İndacaterol, aclidinium ve vilanterol
xcii. İndacaterol, aclidinium ve carmoterol
xciii. İndacaterol, aclidinium ve bambuterol
xciv. İndacaterol, oxitropium ve salmeterol
xcv. İndacaterol, oxitropium ve formoterol
xcvi. İndacaterol, oxitropium ve arformoterol
xcvii. İndacaterol, oxitropium ve olodaterol
xcviii. İndacaterol, oxitropium ve vilanterol
xcix. İndacaterol, oxitropium ve carmoterol
c. İndacaterol, oxitropium ve bambuterol
ci. Vilanterol, tiotropium ve salmeterol
cii. Vilanterol, tiotropium ve formoterol
ciii. Vilanterol, tiotropium ve arformoterol
civ. Vilanterol, tiotropium ve indacaterol
cv. Vilanterol, tiotropium ve olodaterol
cvi. Vilanterol, tiotropium ve carmoterol
cvii. Vilanterol, tiotropium ve bambuterol
cviii. Vilanterol, glycopyrronium ve salmeterol
cix. Vilanterol, glycopyrronium ve formoterol
cx. Vilanterol, glycopyrronium ve arformoterol
cxi. Vilanterol, glycopyrronium ve indacaterol
cxii. Vilanterol, glycopyrronium ve olodaterol
cxiii. Vilanterol, glycopyrronium ve carmoterol
cxiv. Vilanterol, glycopyrronium ve bambuterol
cxv. Vilanterol, aclidinium ve salmeterol
cxvi. Vilanterol, aclidinium ve formoterol
cxvii. Vilanterol, aclidinium ve arformoterol
cxviii. Vilanterol, aclidinium ve indacaterol
cxix. Vilanterol, aclidinium ve olodaterol
cxx. Vilanterol, aclidinium ve carmoterol
cxxi. Vilanterol, aclidinium ve bambuterol
cxxii. Vilanterol, oxitropium ve salmeterol
cxxiii. Vilanterol, oxitropium ve formoterol
cxxiv. Vilanterol, oxitropium ve arformoterol
cxxv. Vilanterol, oxitropium ve indacaterol
cxxvi. Vilanterol, oxitropium ve olodaterol
cxxvii. Vilanterol, oxitropium ve carmoterol
cxxviii. Vilanterol, oxitropium ve bambuterol
cxxix. Carmoterol, tiotropium ve salmeterol
cxxx. Carmoterol, tiotropium ve formoterol
cxxxi. Carmoterol, tiotropium ve arformoterol
cxxxii. Carmoterol, tiotropium ve indacaterol
cxxxiii. Carmoterol, tiotropium ve olodaterol
cxxxiv. Carmoterol, tiotropium ve vilanterol
cxxxv. Carmoterol, tiotropium ve bambuterol
cxxxvi. Carmoterol, glycopyrronium ve salmeterol
cxxxvii. Carmoterol, glycopyrronium ve formoterol
cxxxviii. Carmoterol, glycopyrronium ve arformoterol
cxxxix. Carmoterol, glycopyrronium ve indacaterol
cxl. Carmoterol, glycopyrronium ve olodaterol
cxli. Carmoterol, glycopyrronium ve vilanterol
cxlii. Carmoterol, glycopyrronium ve bambuterol
cxliii. Carmoterol, aclidinium ve salmeterol
cxliv. Carmoterol, aclidinium ve formoterol
cxlv. Carmoterol, aclidinium ve arformoterol
cxlvi. Carmoterol, aclidinium ve indacaterol
cxlvii. Carmoterol, aclidinium ve olodaterol cxlviii. Carmoterol, aclidinium ve vilanterol
cxlix. Carmoterol, aclidinium ve bambuterol
cl. Carmoterol, oxitropium ve salmeterol
cli. Carmoterol, oxitropium ve formoterol
clii. Carmoterol, oxitropium ve arformoterol
cliii. Carmoterol, oxitropium ve indacaterol
cliv. Carmoterol, oxitropium ve olodaterol
clv. Carmoterol, oxitropium ve vilanterol
clvi. Carmoterol, oxitropium ve bambuterol
clvii. Olodaterol, tiotropium ve salmeterol
clviii. Olodaterol, tiotropium ve formoterol
clix. Olodaterol, tiotropium ve arformoterol
clx. Olodaterol, tiotropium ve indacaterol
clxi. Olodaterol, tiotropium ve vilanterol
clxii. Olodaterol, tiotropium ve bambuterol
clxiii. Olodaterol, glycopyrronium ve salmeterol
clxiv. Olodaterol, glycopyrronium ve formoterol
clxv. Olodaterol, glycopyrronium ve arformoterol
clxvi. Olodaterol, glycopyrronium ve indacaterol
clxvii. Olodaterol, glycopyrronium ve vilanterol
clxviii. Olodaterol, glycopyrronium ve bambuterol
clxix. Olodaterol, aclidinium ve salmeterol
clxx. Olodaterol, aclidinium ve formoterol
clxxi. Olodaterol, aclidinium ve arformoterol
clxxii. Olodaterol, aclidinium ve indacaterol
clxxiii. Olodaterol, aclidinium ve vilanterol
clxxiv. Olodaterol, aclidinium ve bambuterol
clxxv. Olodaterol, oxitropium ve salmeterol
clxxvi. Olodaterol, oxitropium ve formoterol
clxxvii. Olodaterol, oxitropium ve arformoterol
clxxviii. Olodaterol, oxitropium ve indacaterol
clxxix. Olodaterol, oxitropium ve vilanterol
clxxx. Olodaterol, oxitropium ve bambuterol wherein the above therapeutic agents can be present as a pharmaceutically acceptable salt or ester thereof, or in enantiomerically pure form or as a racemic mixture.

Said compositions are used for the prevention or treatment of chronic obstructive pulmonary disease and asthma in mammals, especially in humans.

In another preferred embodiment of the invention, said composition comprises a blister having air and moisture barrier property, enabling simultaneous, respective and synchronic application.

In another preferred embodiment of the invention, said composition comprises a dry powder inhaler device suitable for simultaneous, respective and synchronic application in a blister and having at least one locking mechanism ensuring the device to be maintained locked in both of the positions in which it is ready for inhalation and its lid is closed and ensuring the device to be automatically re-set once the lid is closed.

In another preferred embodiment of the invention, said composition comprises a dry powder inhaler device suitable for simultaneous, respective and synchronic application in a blister.

In another preferred embodiment of the invention, pharmaceutically acceptable amount of said composition is administered one a day.

In another preferred embodiment of the invention, pharmaceutically acceptable amount of said composition is administered twice a day.

DETAILED DESCRIPTION OF INVENTION

Examples—A a)

| Content | % Weight (w/w) |
|---|---|
| Muscarinic receptor antagonist | 0.1-12 |
| Lactose (fine particle) | 4.3-5.3 |
| Mannitol (coarse particle) | 84-96 | b)

| Content | % Weight (w/w) |
|---|---|
| Muscarinic receptor antagonist | 0.1-12 |
| Mannitol (fine particle) | 4.3-5.3 |
| Lactose (coarse particle) | 84-96 | c)

| Content | % Weight (w/w) |
|---|---|
| Muscarinic receptor antagonist | 0.1-12 |
| Mannitol + Lactose (fine particle) | 4.3-5.3 |
| Lactose + Mannitol (coarse particle) | 84-96 |

TABLE 1

| Amount | Aklidinyum | | Glycopyrronium | | Darotropyum | | Tiotropium | | ipratropium | | Oxitropium | | Lactose + Mannitol | |
|---|---|---|---|---|---|---|---|---|---|---|---|---|---|---|
| % (w/w) | 5 mg | 25 mg | 5 mg | 25 mg | 5 mg | 25 mg | 5 mg | 25 mg | 5 mg | 25 mg | 5 mg | 25 mg | 5 mg | 25 mg |
| Ex. 1.1 (% w/w) | 4 | 0.8 | — | | — | | — | | — | | — | | 96.0 | 99.2 |
| Ex. 1.2 (% w/w) | 8 | 1.6 | — | | — | | — | | — | | — | | 92.0 | 98.4 |
| Ex. 1.3 (% w/w) | — | | 2 | 0.4 | — | | — | | — | | — | | 98.0 | 99.6 |
| Ex. 1.4 (% w/w) | — | | 4 | 0.8 | — | | — | | — | | — | | 96.0 | 99.2 |
| Ex. 1.5 (% w/w) | — | | — | | 0.4 | 0.08 | — | | — | | — | | 99.6 | 99.92 |
| Ex. 1.6 (% w/w) | — | | — | | — | | 0.36 | 0.072 | — | | — | | 99.64 | 99.28 |
| Ex. 1.7 (% w/w) | — | | — | | — | | — | | 0.5 | 0.1 | — | | 99.5 | 99.9 |
| Ex. 1.8 (% w/w) | — | | — | | — | | — | | — | | 4 | 0.8 | 96 | 99.2 |

Examples B a)

| Content | Amount % (w/w) |
|---|---|
| Muscarinic receptor antagonist | |
| Beta-2 adrenerjik agonist | |
| Lactose + mannitol | |

TABLE 2.1

| Amount % (w/w) 5 mg | Content | | | | | | |
|---|---|---|---|---|---|---|---|
| | Aklidinyum | Glycopyrronium | Darotropyum | Tiotropium | Oxitropium | ipratropium | Carmeterol |
| Ex. 2.1 (% w/w) | 4.0 | 8.0 | — | | | — | — |
| Ex. 2.2 (% w/w) | 4.0 | 8.0 | — | | | — | — |
| Ex. 2.3 (% w/w) | 4.0 | 8.0 | — | | | — | — |
| Ex. 2.4 (% w/w) | 4.0 | 8.0 | — | | | — | — |
| Ex. 2.5 (% w/w) | 4.0 | 8.0 | — | | | — | — |
| Ex. 2.6 (% w/w) | 4.0 | 8.0 | — | | | — | — |
| Ex. 2.7 (% w/w) | 4.0 | 8.0 | — | | | — | — |
| Ex. 2.8 (% w/w) | — | 2.0 | 4.0 | | | — | — |
| Ex. 2.9 (% w/w) | — | 2.0 | 4.0 | | | — | — |
| Ex. 2.10 (% w/w) | — | 2.0 | 4.0 | | | — | — |
| Ex. 2.11 (% w/w) | — | 2.0 | 4.0 | | | — | — |
| Ex. 2.12 (% w/w) | — | 2.0 | 4.0 | | | — | — |
| Ex. 2.13 (% w/w) | — | 2.0 | 4.0 | | | — | — |
| Ex. 2.14 (% w/w) | — | 2.0 | 4.0 | | | — | — |
| Ex. 2.15 (% w/w) | — | — | 0.4 | | | — | — |
| Ex. 2.16 (% w/w) | — | — | 0.4 | | | — | — |
| Ex. 2.17 (% w/w) | — | — | 0.4 | | | — | — |
| Ex. 2.18 (% w/w) | — | — | 0.4 | | | — | — |
| Ex. 2.19 (% w/w) | — | — | 0.4 | | | — | — |
| Ex. 2.20 (% w/w) | — | — | 0.4 | | | — | — |
| Ex. 2.21 (% w/w) | — | — | 0.4 | | | — | — |
| Ex. 2.22 (% w/w) | — | — | — | | | 3.0 | 6.0 | — |
| Ex. 2.23 (% w/w) | — | — | — | | | 3.0 | 6.0 | — |
| Ex. 2.24 (% w/w) | — | — | — | | | 3.0 | 6.0 | — |
| Ex. 2.25 (% w/w) | — | — | — | | | 3.0 | 6.0 | — |
| Ex. 2.26 (% w/w) | — | — | — | | | 3.0 | 6.0 | — |
| Ex. 2.27 (% w/w) | — | — | — | | | 3.0 | 6.0 | — |
| Ex. 2.28 (% w/w) | — | — | — | | | — | — |
| Ex. 2.29 (% w/w) | — | — | — | | | — | — |
| Ex. 2.30 (% w/w) | — | — | — | | | — | — |

TABLE 2.1-continued

| | | | | | | | | | |
|---|---|---|---|---|---|---|---|---|---|
| Ex. 2.31 (% w/w) | — | — | — | | | — | — | | |
| Ex. 2.32 (% w/w) | — | — | — | | | — | — | | |
| Ex. 2.33 (% w/w) | — | — | — | | | — | — | | |
| Ex. 2.34 (% w/w) | — | — | — | | | — | — | 0.04 | 0.08 |
| Ex. 2.35 (% w/w) | — | — | — | | | — | — | 0.04 | 0.08 |
| Ex. 2.36 (% w/w) | — | — | — | | | — | — | 0.04 | 0.08 |
| Ex. 2.37 (% w/w) | — | — | — | | | — | — | 0.04 | 0.08 |
| Ex. 2.38 (% w/w) | — | — | — | | | — | — | 0.04 | 0.08 |
| Ex. 2.39 (% w/w) | — | — | — | | | — | — | 0.04 | 0.08 |
| Ex. 2.40 (% w/w) | — | — | — | | | — | — | — | |
| Ex. 2.41 (% w/w) | — | — | — | | | — | — | — | |
| Ex. 2.42 (% w/w) | — | — | — | | | — | — | — | |
| Ex. 2.43 (% w/w) | — | — | — | | | — | — | — | |
| Ex. 2.44 (% w/w) | — | — | — | | | — | — | — | |
| Ex. 2.45 (% w/w) | — | — | — | | | — | — | — | |
| Ex. 2.46 (% w/w) | | | | 0.36 | | | | | |
| Ex. 2.47 (% w/w) | | | | 0.36 | | | | | |
| Ex. 2.48 (% w/w) | | | | 0.36 | | | | | |
| Ex. 2.49 (% w/w) | | | | 0.36 | | | | | |
| Ex. 2.50 (% w/w) | | | | 0.36 | | | | | |
| Ex. 2.51 (% w/w) | | | | 0.36 | | | | | |
| Ex. 2.52 (% w/w) | | | | 0.36 | | | | | |
| Ex. 2.53 (% w/w) | | | | | 4 | | | | |
| Ex. 2.54 (% w/w) | | | | | 4 | | | | |
| Ex. 2.55 (% w/w) | | | | | 4 | | | | |
| Ex. 2.56 (% w/w) | | | | | 4 | | | | |
| Ex. 2.57 (% w/w) | | | | | 4 | | | | |
| Ex. 2.58 (% w/w) | | | | | 4 | | | | |
| Ex. 2.59 (% w/w) | | | | | 4 | | | | |

| Amount | Content | | | | | | | |
|---|---|---|---|---|---|---|---|---|
| % (w/w) 5 mg | Olodaterol | Salmeterol | Formoterol | | Arformoterol | indacaterol | Olodaterol | Vilanterol | Lactose + Mannitol |
| Ex. 2.1 (% w/w) | — | 1.0 | — | | — | — | — | — | 95.0 91.0 |
| Ex. 2.2 (% w/w) | — | — | 0.10 | 0.24 | — | — | — | — | 95.9 91.76 |
| Ex. 2.3 (% w/w) | — | — | — | | 0.3 | — | — | — | 95.7 91.7 |
| Ex. 2.4 (% w/w) | — | — | — | | — | 3.0 | — | — | 93.0 89.0 |
| Ex. 2.5 (% w/w) | — | — | — | | — | — | 0.1 | — | 95.9 91.9 |
| Ex. 2.6 (% w/w) | — | — | — | | — | — | — | 0.5 | 95.5 91.5 |
| Ex. 2.7 (% w/w) | — | — | — | | — | — | — | — | 95.96 91.92 |
| Ex. 2.8 (% w/w) | — | 1.0 | — | | — | — | — | — | 97.0 95.0 |

TABLE 2.1-continued

| | | | | | | | | | | | |
|---|---|---|---|---|---|---|---|---|---|---|---|
| Ex. 2.9 (% w/w) | — | — | 0.10 | 0.24 | — | — | — | — | 97.9 | 95.76 |
| Ex. 2.10 (% w/w) | — | — | — | — | 0.3 | — | — | — | 97.7 | 95.7 |
| Ex. 2.11 (% w/w) | — | — | — | — | — | 3.0 | — | — | 95.0 | 93.0 |
| Ex. 2.12 (% w/w) | — | — | — | — | — | — | 0.1 | — | 97.9 | 95.9 |
| Ex. 2.13 (% w/w) | — | — | — | — | — | — | — | 0.5 | 97.5 | 95.5 |
| Ex. 2.14 (% w/w) | — | — | — | — | — | — | — | — | 95.96 | 91.92 |
| Ex. 2.15 (% w/w) | — | — | 1.0 | — | — | — | — | — | 98.6 | |
| Ex. 2.16 (% w/w) | — | — | — | 0.10 | 0.24 | — | — | — | — | 99.5 | 99.36 |
| Ex. 2.17 (% w/w) | — | — | — | — | 0.3 | — | — | — | 99.3 | |
| Ex. 2.18 (% w/w) | — | — | — | — | — | 3.0 | — | — | 96.6 | |
| Ex. 2.19 (% w/w) | — | — | — | — | — | — | 0.1 | — | 99.5 | |
| Ex. 2.20 (% w/w) | — | — | — | — | — | — | — | 0.5 | 99.1 | |
| Ex. 2.21 (% w/w) | — | — | — | — | — | — | — | — | 99.56 | 99.52 |
| Ex. 2.22 (% w/w) | — | — | 1.0 | — | — | — | — | — | 96.0 | 93.0 |
| Ex. 2.23 (% w/w) | — | — | — | 0.10 | 0.24 | — | — | — | 96.9 | 96.76 |
| Ex. 2.24 (% w/w) | — | — | — | — | 0.3 | — | — | — | 96.7 | 93.7 |
| Ex. 2.25 (% w/w) | — | — | — | — | — | — | 0.1 | — | 96.9 | 93.9 |
| Ex. 2.26 (% w/w) | — | — | — | — | — | — | — | 0.5 | 96.5 | 93.5 |
| Ex. 2.27 (% w/w) | — | — | — | — | — | — | — | — | 96.96 | 96.92 |
| Ex. 2.28 (% w/w) | — | — | 1.0 | — | — | — | — | — | 98.5 | |
| Ex. 2.29 (% w/w) | — | — | — | 0.10 | 0.24 | — | — | — | 99.4 | 99.26 |
| Ex. 2.30 (% w/w) | — | — | — | — | 0.3 | — | — | — | 99.2 | |
| Ex. 2.31 (% w/w) | — | — | — | — | — | 3.0 | — | — | 96.5 | |
| Ex. 2.32 (% w/w) | — | — | — | — | — | — | 0.1 | — | 99.4 | |
| Ex. 2.33 (% w/w) | — | — | — | — | — | — | — | — | 99.46 | 99.42 |
| Ex. 2.34 (% w/w) | — | — | 1.0 | — | — | — | — | — | 98.96 | 98.92 |
| Ex. 2.35 (% w/w) | — | — | — | 0.10 | 0.24 | — | — | — | 99.86 | 99.68 |
| Ex. 2.36 (% w/w) | — | — | — | — | 0.3 | — | — | — | 99.66 | 99.62 |
| Ex. 2.37 (% w/w) | — | — | — | — | — | 3.0 | — | — | 96.96 | 96.92 |
| Ex. 2.38 (% w/w) | — | — | — | — | — | — | 0.1 | — | 99.86 | 99.82 |
| Ex. 2.39 (% w/w) | — | — | — | — | — | — | — | 0.5 | 99.46 | 99.42 |
| Ex. 2.40 (% w/w) | 0.1 | 0.2 | 1.0 | — | — | — | — | — | 98.9 | 98.8 |
| Ex. 2.41 (% w/w) | 0.1 | 0.2 | — | 0.10 | 0.24 | — | — | — | 99.8 | 99.56 |
| Ex. 2.42 (% w/w) | 0.1 | 0.2 | — | — | 0.3 | — | — | — | 99.6 | 99.5 |
| Ex. 2.43 (% w/w) | 0.1 | 0.2 | — | — | — | 3.0 | — | — | 96.9 | 96.8 |
| Ex. 2.44 (% w/w) | 0.1 | 0.2 | — | — | — | — | — | 0.5 | 99.4 | 99.3 |
| Ex. 2.45 (% w/w) | 0.1 | 0.2 | — | — | — | — | — | — | — | 99.72 |
| Ex. 2.46 (% w/w) | | | 1.0 | — | — | — | — | — | — | 98.64 |
| Ex. 2.47 (% w/w) | | | — | 0.10 | 0.24 | — | — | — | 99.54 | 99.4 |
| Ex. 2.48 (% w/w) | | | | | 0.3 | — | — | — | | 99.34 |

TABLE 2.1-continued

| | | | | | | | | |
|---|---|---|---|---|---|---|---|---|
| Ex. 2.49 (% w/w) | — | — | — | 3.0 | — | — | | 96.64 |
| Ex. 2.50 (% w/w) | — | — | — | — | 0.1 | — | | 99.54 |
| Ex. 2.51 (% w/w) | — | — | — | — | — | 0.5 | | 99.14 |
| Ex. 2.52 (% w/w) | — | — | — | — | — | — | | 99.64 |
| Ex. 2.53 (% w/w) | 1.0 | — | — | — | — | — | | 95 |
| Ex. 2.54 (% w/w) | — | 0.10 | 0.24 | — | — | — | 95.9 | 95.76 |
| Ex. 2.55 (% w/w) | — | — | 0.3 | — | — | — | | 95.7 |
| Ex. 2.56 (% w/w) | — | — | — | 3.0 | — | — | | 95.7 |
| Ex. 2.57 (% w/w) | — | — | — | — | 0.1 | — | | 95.9 |
| Ex. 2.58 (% w/w) | — | — | — | — | — | 0.5 | | 95.5 |
| Ex. 2.59 (% w/w) | — | — | — | — | — | — | | 96 |

TABLE 2.2

| Amount % (w/w) 25 mg | Aklidinyum | Glycopyrronium | Dara-tropium | Tio-tropium | ipra-tropium | Oxi-tropium | indacaterol | Vilanterol | Carmeterol | Olodaterol |
|---|---|---|---|---|---|---|---|---|---|---|
| Ex. 2.1 (% w/w) | 0.8 | 1.6 | — | — | | | | — | — | — | — |
| Ex. 2.2 (% w/w) | 0.8 | 1.6 | — | — | | | | — | — | — | — |
| Ex. 2.3 (% w/w) | 0.8 | 1.6 | — | — | | | | — | — | — | — |
| Ex. 2.4 (% w/w) | 0.8 | 1.6 | — | — | | | | — | — | — | — |
| Ex. 2.5 (% w/w) | 0.8 | 1.6 | — | — | | | | — | — | — | — |
| Ex. 2.6 (% w/w) | 0.8 | 1.6 | — | — | | | | — | — | — | — |
| Ex. 2.7 (% w/w) | 0.8 | 1.6 | — | — | | | | — | — | — | — |
| Ex. 2.8 (% w/w) | — | 0.4 | 0.8 | — | | | | — | — | — | — |
| Ex. 2.9 (% w/w) | — | 0.4 | 0.8 | — | | | | — | — | — | — |
| Ex. 2.10 (% w/w) | — | 0.4 | 0.8 | — | | | | — | — | — | — |
| Ex. 2.11 (% w/w) | — | 0.4 | 0.8 | — | | | | — | — | — | — |
| EX. 2.12 (% w/w) | — | 0.4 | 0.8 | — | | | | — | — | — | — |
| Ex. 2.13 (% w/w) | — | 0.4 | 0.8 | — | | | | — | — | — | — |
| Ex. 2.14 (% w/w) | — | 0.4 | 0.8 | — | | | | — | — | — | — |
| Ex. 2.15 (% w/w) | — | — | 0.08 | | | | | — | — | — | — |
| Ex. 2.16 (% w/w) | — | — | 0.08 | | | | | — | — | — | — |
| Ex. 2.17 (% w/w) | — | — | 0.08 | | | | | — | — | — | — |
| Ex. 2.18 (% w/w) | — | — | 0.08 | | | | | — | — | — | — |
| Ex. 2.19 (% w/w) | — | — | 0.08 | | | | | — | — | — | — |
| Ex. 2.20 (% w/w) | — | — | 0.08 | | | | | — | — | — | — |
| Ex. 2.21 (% w/w) | — | — | 0.08 | | | | | — | — | — | — |
| Ex. 2.22 (% w/w) | — | — | — | | | | | 0.6 | 1.2 | — | — |
| Ex. 2.23 (% w/w) | — | — | — | | | | | 0.6 | 1.2 | — | — |

TABLE 2.2-continued

| | | | | | | | | | | |
|---|---|---|---|---|---|---|---|---|---|---|
| Ex. 2.24 (% w/w) | — | — | — | | 0.6 | 1.2 | — | — | — | |
| Ex. 2.25 (% w/w) | — | — | — | | 0.6 | 1.2 | — | — | — | |
| Ex. 2.26 (% w/w) | — | — | — | | 0.6 | 1.2 | — | — | — | |
| Ex. 2.27 (% w/w) | — | — | — | | 0.6 | 1.2 | — | — | — | |
| Ex. 2.28 (% w/w) | — | — | — | | — | — | 0.1 | — | — | |
| Ex. 2.29 (% w/w) | — | — | — | | — | — | 0.1 | — | — | |
| Ex. 2.30 (% w/w) | — | — | — | | — | — | 0.1 | — | — | |
| Ex. 2.31 (% w/w) | — | — | — | | — | — | 0.1 | — | — | |
| Ex. 2.32 (% w/w) | — | — | — | | — | — | 0.1 | — | — | |
| Ex. 2.33 (% w/w) | — | — | — | | — | — | 0.1 | — | — | |
| Ex. 2.34 (% w/w) | — | — | — | | — | — | — | 0.01 | 0.02 | — |
| Ex. 2.35 (% w/w) | — | — | — | | — | — | — | 0.01 | 0.02 | — |
| Ex. 2.36 (% w/w) | — | — | — | | — | — | — | 0.01 | 0.02 | — |
| Ex. 2.37 (% w/w) | — | — | — | | — | — | — | 0.01 | 0.02 | — |
| Ex. 2.38 (% w/w) | — | — | — | | — | — | — | 0.01 | 0.02 | — |
| Ex. 2.39 (% w/w) | — | — | — | | — | — | — | 0.01 | 0.02 | — |
| Ex. 2.40 (% w/w) | — | — | — | | — | — | — | — | 0.02 | 0.04 |
| Ex. 2.41 (% w/w) | — | — | — | | — | — | — | — | 0.02 | 0.04 |
| Ex. 2.42 (% w/w) | — | — | — | | — | — | — | — | 0.02 | 0.04 |
| Ex. 2.43 (% w/w) | — | — | — | | — | — | — | — | 0.02 | 0.04 |
| Ex. 2.44 (% w/w) | — | — | — | | — | — | — | — | 0.02 | 0.04 |
| Ex. 2.45 (% w/w) | — | — | — | | — | — | — | — | 0.02 | 0.04 |
| Ex. 2.46 (% w/w) | | | 0.072 | | | | | | | |
| Ex. 2.47 (% w/w) | | | 0.072 | | | | | | | |
| Ex. 2.48 (% w/w) | | | 0.072 | | | | | | | |
| Ex 2.49 (% w/w) | | | 0.072 | | | | | | | |
| Ex. 2.50 (% w/w) | | | 0.072 | | | | | | | |
| Ex. 2.51 (% w/w) | | | 0.072 | | | | | | | |
| Ex. 2.52 (% w/w) | | | 0.072 | | | | | | | |
| Ex. 2.53 (% w/w) | | | | 3.0 | 6.0 | | | | | |
| Ex. 2.54 (% w/w) | | | | 3.0 | 6.0 | | | | | |
| Ex. 2.55 (% w/w) | | | | 3.0 | 6.0 | | | | | |
| Ex. 2.56 (% w/w) | | | | 3.0 | 6.0 | | | | | |
| Ex. 2.57 (% w/w) | | | | 3.0 | 6.0 | | | | | |
| Ex. 2.58 (% w/w) | | | | 3.0 | 6.0 | | | | | |
| Ex. 2.59 (% w/w) | | | | 3.0 | 6.0 | | | | | |
| Ex. 2.60 (% w/w) | | | | | 0.8 | | | | | |
| Ex. 2.61 (% w/w) | | | | | 0.8 | | | | | |
| Ex. 2.62 (% w/w) | | | | | 0.8 | | | | | |
| Ex. 2.63 (% w/w) | | | | | 0.8 | | | | | |

TABLE 2.2-continued

| | | | | | | | |
|---|---|---|---|---|---|---|---|
| Ex. 2.64 (% w/w) | | | | 0.8 | | | |
| Ex. 2.65 (% w/w) | | | | 0.8 | | | |
| Ex. 2.66 (% w/w) | | | | 0.8 | | | |

| Amount | Content | | | | | | | | |
|---|---|---|---|---|---|---|---|---|---|
| % (w/w) 25 mg | Salmeterol | Formoterol | Artormoterol | indacaterol | Olodaterol | Vilanterol | Carmeterol | Lactose + Mannitol | |
| Ex. 2.1 (% w/w) | 0.2 | — | — | — | — | — | — | 99.0 | 98.2 |
| Ex. 2.2 (% w/w) | — | 0.02 | 0.05 | — | — | — | — | 99.18 | 98.35 |
| Ex. 2.3 (% w/w) | — | — | 0.06 | — | — | — | — | 99.14 | 98.34 |
| Ex. 2.4 (% w/w) | — | — | — | 0.6 | — | — | — | 98.6 | 97.8 |
| Ex. 2.5 (% w/w) | — | — | — | — | 0.02 | — | — | 99.18 | 98.38 |
| Ex. 2.6 (% w/w) | — | — | — | — | — | 0.1 | — | 99.1 | 98.3 |
| Ex. 2.7 (% w/w) | — | — | — | — | — | — | 0.01 0.02 | 99.19 | 98.38 |
| Ex. 2.8 (% w/w) | 0.2 | — | — | — | — | — | — | 99.4 | 99.0 |
| Ex. 2.9 (% w/w) | — | 0.02 | 0.05 | — | — | — | — | 99.58 | 99.15 |
| Ex. 2.10 (% w/w) | — | — | 0.06 | — | — | — | — | 99.54 | 99.32 |
| Ex. 2.11 (% w/w) | — | — | — | 0.6 | — | — | — | 99.0 | 98.6 |
| EX. 2.12 (% w/w) | — | — | — | — | 0.02 | — | — | 99.58 | 99.18 |
| Ex. 2.13 (% w/w) | — | — | — | — | — | 0.1 | — | 99.5 | 99.1 |
| Ex. 2.14 (% w/w) | — | — | — | — | — | — | 0.01 0.02 | 99.59 | 99.18 |
| Ex. 2.15 (% w/w) | 0.2 | — | — | — | — | — | — | 99.72 | |
| Ex. 2.16 (% w/w) | — | 0.02 | 0.05 | — | — | — | — | 99.90 | 99.87 |
| Ex. 2.17 (% w/w) | — | — | 0.06 | — | — | — | — | 99.86 | |
| Ex. 2.18 (% w/w) | — | — | — | 0.6 | — | — | — | 99.32 | |
| Ex. 2.19 (% w/w) | — | — | — | — | 0.02 | — | — | 99.9 | |
| Ex. 2.20 (% w/w) | — | — | — | — | — | 0.1 | — | 99.82 | |
| Ex. 2.21 (% w/w) | — | — | — | — | — | — | 0.01 0.02 | 99.91 | 99.90 |
| Ex. 2.22 (% w/w) | 0.2 | — | — | — | — | — | — | 99.2 | 98.6 |
| Ex. 2.23 (% w/w) | — | 0.02 | 0.05 | — | — | — | — | 99.38 | 98.75 |
| Ex. 2.24 (% w/w) | — | — | 0.06 | — | — | — | — | 99.43 | 98.74 |
| Ex. 2.25 (% w/w) | — | — | — | — | 0.02 | — | — | 99.38 | 98.78 |
| Ex. 2.26 (% w/w) | — | — | — | — | — | 0.1 | — | 99.3 | 98.7 |
| Ex. 2.27 (% w/w) | — | — | — | — | — | — | 0.01 0.02 | 99.39 | 98.78 |
| Ex. 2.28 (% w/w) | 0.2 | — | — | — | — | — | — | 99.7 | |
| Ex. 2.29 (% w/w) | — | 0.02 | 0.05 | — | — | — | — | 99.88 | 99.85 |
| Ex. 2.30 (% w/w) | — | — | 0.06 | — | — | — | — | 99.84 | |
| Ex. 2.31 (% w/w) | — | — | — | 0.6 | — | — | — | 99.3 | |
| Ex. 2.32 (% w/w) | — | — | — | — | 0.02 | — | — | 99.88 | |
| Ex. 2.33 (% w/w) | — | — | — | — | — | — | 0.01 0.02 | 99.89 | 99.88 |
| Ex. 2.34 (% w/w) | 0.2 | — | — | — | — | — | — | 99.79 | 99.78 |

TABLE 2.2-continued

| | | | | | | | | | | |
|---|---|---|---|---|---|---|---|---|---|---|
| Ex. 2.35 (% w/w) | — | 0.02 | 0.05 | — | — | — | — | — | 99.97 | 99.93 |
| Ex. 2.36 (% w/w) | — | — | 0.06 | — | — | — | — | — | 99.93 | 99.92 |
| Ex. 2.37 (% w/w) | — | — | — | 0.6 | — | — | — | — | 99.39 | 99.38 |
| Ex. 2.38 (% w/w) | — | — | — | — | 0.02 | — | — | — | 99.97 | 99.96 |
| Ex. 2.39 (% w/w) | — | — | — | — | — | 0.1 | — | — | 99.89 | 99.88 |
| Ex. 2.40 (% w/w) | 1.0 | — | — | — | — | — | — | — | 98.88 | 98.86 |
| Ex. 2.41 (% w/w) | — | 0.02 | 0.05 | — | — | — | — | — | 99.96 | 99.91 |
| Ex. 2.42 (% w/w) | — | — | 0.06 | — | — | — | — | — | 99.92 | 99.90 |
| Ex. 2.43 (% w/w) | — | — | — | 0.6 | — | — | — | — | 99.38 | 99.36 |
| Ex. 2.44 (% w/w) | — | — | — | — | — | 0.1 | — | — | 99.88 | 99.86 |
| Ex. 2.45 (% w/w) | — | — | — | — | — | — | 0.01 | 0.02 | 99.97 | 99.94 |
| Ex. 2.46 (% w/w) | 0.2 | — | — | — | — | — | — | — | | 99.728 |
| Ex. 2.47 (% w/w) | — | 0.02 | 0.05 | — | — | — | — | — | 99.908 | 99.878 |
| Ex. 2.48 (% w/w) | — | — | 0.06 | — | — | — | — | — | | 99.868 |
| Ex 2.49 (% w/w) | — | — | — | 0.6 | — | — | — | — | | 99.328 |
| Ex. 2.50 (% w/w) | — | — | — | — | 0.02 | — | — | — | | 99.908 |
| Ex. 2.51 (% w/w) | — | — | — | — | — | 0.1 | — | — | | 99.828 |
| Ex. 2.52 (% w/w) | — | — | — | — | — | — | 0.01 | 0.02 | 99.918 | 99.908 |
| Ex. 2.53 (% w/w) | 0.2 | — | — | — | — | — | — | — | 96.8 | 93.8 |
| Ex. 2.54 (% w/w) | — | 0.02 | 0.05 | — | — | — | — | — | 96.98 | 93.95 |
| Ex. 2.55 (% w/w) | — | — | 0.06 | — | — | — | — | — | 96.94 | 93.94 |
| Ex. 2.56 (% w/w) | — | — | — | 0.6 | — | — | — | — | 96.4 | 93.4 |
| Ex. 2.57 (% w/w) | — | — | — | — | 0.02 | — | — | — | 96.98 | 93.98 |
| Ex. 2.58 (% w/w) | — | — | — | — | — | 0.1 | — | — | 96.9 | 93.9 |
| Ex. 2.59 (% w/w) | — | — | — | — | — | — | 0.01 | 0.02 | 96.99 | 93.98 |
| Ex. 2.60 (% w/w) | 0.2 | — | — | — | — | — | — | — | | 99 |
| Ex. 2.61 (% w/w) | — | 0.02 | 0.05 | — | — | — | — | — | 99.18 | 99.15 |
| Ex. 2.62 (% w/w) | — | — | 0.06 | — | — | — | — | — | | 99.14 |
| Ex. 2.63 (% w/w) | — | — | — | 0.6 | — | — | — | — | | 98.6 |
| Ex. 2.64 (% w/w) | — | — | — | — | 0.02 | — | — | — | | 99.18 |
| Ex. 2.65 (% w/w) | — | — | — | — | — | 0.1 | — | — | | 99.1 |
| Ex. 2.66 (% w/w) | — | — | — | — | — | — | 0.01 | 0.02 | 99.9 | 99.18 |

Examples—C a)

| Content | Değer % (w/w) |
|---|---|
| Muscarinic receptor antagonist | |
| Beta-2 adrenerjik agonist | |
| Lactose + mannitol | |

TABLE 3.1

| Amount % (w/w) 5 mg | Content | | | | | | | | | | | | |
|---|---|---|---|---|---|---|---|---|---|---|---|---|---|
| | Aklidinyum | | Glycopyrronium | | Daratropium | indacaterol | | Vilanterol | Carmeterol | | Olodaterol | |
| Ex. 3.1 (% w/w) | 4.0 | 8.0 | — | | — | — | | — | — | | — | |
| Ex. 3.2 (% w/w) | 4.0 | 8.0 | — | | — | — | | — | — | | — | |
| Ex. 3.3 (% w/w) | 4.0 | 8.0 | — | | — | — | | — | — | | — | |
| Ex. 3.4 (% w/w) | — | | 2.0 | 4.0 | — | — | | — | — | | — | |
| Ex. 3.5 (% w/w) | — | | 2.0 | 4.0 | — | — | | — | — | | — | |
| Ex. 3.6 (% w/w) | — | | 2.0 | 4.0 | — | — | | — | — | | — | |
| Ex. 3.7 (% w/w) | — | | — | | 0.4 | — | | — | — | | — | |
| Ex. 3.8 (% w/w) | — | | — | | 0.4 | — | | — | — | | — | |
| Ex. 3.9 (% w/w) | — | | — | | 0.4 | — | | — | — | | — | |
| Ex. 3.10 (% w/w) | — | | — | | 0.4 | — | | — | — | | — | |
| Ex. 3.11 (% w/w) | — | | — | | — | 3.0 | 6.0 | — | — | | — | |
| Ex. 3.12 (% w/w) | — | | — | | — | 3.0 | 6.0 | — | — | | — | |
| Ex. 3.13 (% w/w) | — | | — | | — | 3.0 | 6.0 | — | — | | — | |
| Ex. 3.14 (% w/w) | — | | — | | — | 3.0 | 6.0 | — | — | | — | |
| Ex. 3.15 (% w/w) | — | | — | | — | — | | 0.5 | — | | — | |
| Ex. 3.16 (% w/w) | — | | — | | — | — | | 0.5 | — | | — | |
| Ex. 3.17 (% w/w) | — | | — | | — | — | | 0.5 | — | | — | |
| Ex. 3.18 (% w/w) | — | | — | | — | — | | 0.5 | — | | — | |
| Ex. 3.19 (% w/w) | — | | — | | — | — | | — | 0.04 | 0.08 | — | |
| Ex. 3.20 (% w/w) | — | | — | | — | — | | — | 0.04 | 0.08 | — | |
| Ex. 3.21 (% w/w) | — | | — | | — | — | | — | 0.04 | 0.08 | — | |
| Ex. 3.22 (% w/w) | — | | — | | — | — | | — | 0.04 | 0.08 | — | |
| Ex. 3.23 (% w/w) | — | | — | | — | — | | — | — | | 0.1 | 0.2 |
| Ex. 3.24 (% w/w) | — | | — | | — | — | | — | — | | 0.1 | 0.2 |
| Ex. 3.25 (% w/w) | — | | — | | — | — | | — | — | | 0.1 | 0.2 |
| Ex. 3.26 (% w/w) | — | | — | | — | — | | — | — | | 0.1 | 0.2 |

| Amount % (w/w) 5 mg | Content | | | | | | | | | |
|---|---|---|---|---|---|---|---|---|---|---|
| | Tiotropium | | Glycopyrronium | | ipratropium | Aklidinyum | | Lactose + Mannitol | | |
| Ex. 3.1 (% w/w) | 0.1 | 0.36 | — | | — | — | | 95.9 | 91.64 | |
| Ex. 3.2 (% w/w) | — | | 2.0 | 4.0 | — | — | | 94.0 | 88.0 | |
| Ex. 3.3 (% w/w) | — | | — | | 0.8 | — | | 95.2 | 91.2 | |
| Ex. 3.4 (% w/w) | 0.1 | 0.36 | — | | — | — | | 97.9 | 95.64 | |
| Ex. 3.5 (% w/w) | — | | — | | 0.8 | — | | 93.2 | 95.2 | |
| Ex. 3.6 (% w/w) | — | | — | | — | 4.0 | 8.0 | 94.0 | 88.0 | |
| Ex. 3.7 (% w/w) | 0.1 | 0.36 | — | | — | — | | 99.5 | 99.24 | |
| Ex. 3.8 (% w/w) | — | | 2.0 | 4.0 | — | — | | 97.6 | 95.6 | |
| Ex. 3.9 (% w/w) | — | | — | | 0.8 | — | | 98.8 | | |
| Ex. 3.10 (% w/w) | — | | — | | — | 4.0 | 8.0 | 95.6 | 91.6 | |
| Ex. 3.11 (% w/w) | 0.1 | 0.36 | — | | — | — | | 96.9 | 93.64 | |
| Ex. 3.12 (% w/w) | — | | 2.0 | 4.0 | — | — | | 95.0 | 90.0 | |
| Ex. 3.13 (% w/w) | — | | — | | 0.8 | — | | 96.2 | 93.2 | |
| Ex. 3.14 (% w/w) | — | | — | | — | 4.0 | 8.0 | 93.0 | 86.0 | |
| Ex. 3.15 (% w/w) | 0.1 | 0.36 | — | | — | — | | 99.4 | 99.14 | |
| Ex. 3.16 (% w/w) | — | | 2.0 | 4.0 | — | — | | 97.5 | 95.5 | |
| Ex. 3.17 (% w/w) | — | | — | | 0.8 | — | | 98.7 | | |
| Ex. 3.18 (% w/w) | — | | — | | — | 4.0 | 8.0 | 95.5 | 91.5 | |
| Ex. 3.19 (% w/w) | 0.1 | 0.36 | — | | — | — | | 99.86 | 99.56 | |
| Ex. 3.20 (% w/w) | — | | 2.0 | 4.0 | — | — | | 97.96 | 95.92 | |
| Ex. 3.21 (% w/w) | — | | — | | 0.8 | — | | 99.16 | 99.12 | |
| Ex. 3.22 (% w/w) | — | | — | | — | 4.0 | 8.0 | 95.96 | 91.96 | |
| Ex. 3.23 (% w/w) | 0.1 | 0.36 | — | | — | — | | 99.8 | 99.44 | |
| Ex. 3.24 (% w/w) | — | | 2.0 | | — | — | | 97.9 | 95.8 | |
| Ex. 3.25 (% w/w) | — | | — | | 0.8 | — | | 99.1 | 99.0 | |
| Ex. 3.26 (% w/w) | — | | — | | — | 4.0 | 8.0 | 95.9 | 91.8 | |

TABLE 3.2

| Amount % (w/w) 25 mg | Content | | | | | | | | | | |
|---|---|---|---|---|---|---|---|---|---|---|---|
| | Aklidinyum | | Glycopyrronium | | Daratropium | indacaterol | Vilanterol | Carmeterol | | Olodaterol | |
| Ex. 3.1 (% w/w) | 0.8 | 1.6 | — | | — | — | — | — | | — | |
| Ex. 3.2 (% w/w) | 0.8 | 1.6 | — | | — | — | — | — | | — | |
| Ex. 3.3 (% w/w) | 0.8 | 1.6 | — | | — | — | — | — | | — | |
| Ex. 3.4 (% w/w) | — | | 0.4 | 0.8 | — | — | — | — | | — | |
| Ex. 3.5 (% w/w) | — | | 0.4 | 0.8 | — | — | — | — | | — | |
| Ex. 3.6 (% w/w) | — | | — | | 0.08 | — | — | — | | — | |

TABLE 3.2-continued

| | | | | | | | | |
|---|---|---|---|---|---|---|---|---|
| Ex. 3.7 (% w/w) | — | — | 0.08 | — | — | — | — | — |
| Ex. 3.8 (% w/w) | — | — | 0.08 | — | — | — | — | — |
| Ex. 3.9 (% w/w) | — | — | 0.08 | — | — | — | — | — |
| Ex. 3.10 (% w/w) | — | — | — | 0.6 | 1.2 | — | — | — |
| Ex. 3.11 (% w/w) | — | — | — | 0.6 | 1.2 | — | — | — |
| Ex. 3.12 (% w/w) | — | — | — | 0.6 | 1.2 | — | — | — |
| Ex. 3.13 (% w/w) | — | — | — | 0.6 | 1.2 | — | — | — |
| Ex. 3.14 (% w/w) | — | — | — | — | 0.1 | — | — | — |
| Ex. 3.15 (% w/w) | — | — | — | — | 0.1 | — | — | — |
| Ex. 3.16 (% w/w) | — | — | — | — | 0.1 | — | — | — |
| Ex. 3.17 (% w/w) | — | — | — | — | 0.1 | — | — | — |
| Ex. 3.18 (% w/w) | — | — | — | — | — | 0.01 | 0.02 | — |
| Ex. 3.19 (% w/w) | — | — | — | — | — | 0.01 | 0.02 | — |
| Ex. 3.20 (% w/w) | — | — | — | — | — | 0.01 | 0.02 | — |
| Ex. 3.21 (% w/w) | — | — | — | — | — | 0.01 | 0.02 | — |
| Ex. 3.22 (% w/w) | — | — | — | — | — | — | 0.02 | 0.04 |
| Ex. 3.23 (% w/w) | — | — | — | — | — | — | 0.02 | 0.04 |
| Ex. 3.24 (% w/w) | — | — | — | — | — | — | 0.02 | 0.04 |
| Ex. 3.25 (% w/w) | — | — | — | — | — | — | 0.02 | 0.04 |

| Amount % (w/w) | Content | | | | | |
|---|---|---|---|---|---|---|
| 25 mg | Tiotropium | Glycopyrronium | ipratropium | Aklidinyum | Lactose + Mannitol | |
| Ex. 3.1 (% w/w) | 0.072  0.02 | — | — | — | 99.13 | 98.38 |
| Ex. 3.2 (% w/w) | — | 0.4  0.8 | — | — | 98.8 | 97.6 |
| Ex. 3.3 (% w/w) | — | — | 0.16 | — | 99.04 | 98.24 |
| Ex. 3.4 (% w/w) | 0.072  0.02 | — | — | — | 99.53 | 99.18 |
| Ex. 3.5 (% w/w) | — | — | 0.16 | — | 99.44 | 99.02 |
| Ex. 3.6 (% w/w) | 0.072  0.02 | — | — | — | 99.85 | 99.90 |
| Ex. 3.7 (% w/w) | — | 0.4  0.8 | — | — | 99.52 | 99.12 |
| Ex. 3.8 (% w/w) | — | — | 0.16 | — | 99.76 | |
| Ex. 3.9 (% w/w) | — | — | — | 0.8  1.6 | 99.12 | 98.32 |
| Ex. 3.10 (% w/w) | 0.072  0.02 | — | — | — | 99.33 | 98.78 |
| Ex. 3.11 (% w/w) | — | 0.4  0.8 | — | — | 99.0 | 98.0 |
| Ex. 3.12 (% w/w) | — | — | 0.16 | — | 99.24 | 98.64 |
| Ex. 3.13 (% w/w) | — | — | — | 0.8  1.6 | 98.6 | 97.2 |
| Ex. 3.14 (% w/w) | 0.072  0.02 | — | — | — | 99.83 | 99.88 |
| Ex. 3.15 (% w/w) | — | 0.4  0.8 | — | — | 99.5 | 99.1 |
| Ex. 3.16 (% w/w) | — | — | 0.16 | — | 99.74 | |
| Ex. 3.17 (% w/w) | — | — | — | 0.8  1.6 | 99.1 | 98.3 |
| Ex. 3.18 (% w/w) | 0.072  0.02 | — | — | — | 99.92 | 99.96 |
| Ex. 3.19 (% w/w) | — | 0.4  0.8 | — | — | 99.59 | 99.18 |
| Ex. 3.20 (% w/w) | — | — | 0.16 | — | 99.83 | 99.82 |
| Ex. 3.21 (% w/w) | — | — | — | 0.8  1.6 | 99.19 | 98.38 |
| Ex. 3.22 (% w/w) | 0.072  0.02 | — | — | — | 99.91 | 99.94 |
| Ex. 3.23 (% w/w) | — | 0.4  0.8 | — | — | 99.58 | 99.16 |
| Ex. 3.24 (% w/w) | — | — | 0.16 | — | 99.82 | 99.80 |
| Ex. 3.25 (% w/w) | — | — | — | 0.8  1.6 | 99.18 | 98.36 |

Examples—D a)

| Content | Değer % (w/w) |
|---|---|
| Muscarinic receptor antagonist | |
| Beta-2 adrenerjik agonist | |
| Lactose + mannitol | |

TABLE 4.1

| Amount % (w/w) | Content | | | | | | | |
|---|---|---|---|---|---|---|---|---|
| 5 mg | Aklidinyum | Glycopyrronium | Daratropium | indacaterol | Vilanterol | Carmeterol | Olodaterol | Salbutamol |
| Ex. 4.1 (% w/w) | 4.0 | 8.0 | — | — | — | — | — | 2.0 |
| Ex. 4.2 (% w/w) | 4.0 | 8.0 | — | — | — | — | — | — |
| Ex. 4.3 (% w/w) | 4.0 | 8.0 | — | — | — | — | — | — |
| Ex. 4.4 (% w/w) | 4.0 | 8.0 | — | — | — | — | — | — |
| Ex. 4.5 (% w/w) | 4.0 | 8.0 | — | — | — | — | — | — |

TABLE 4.1-continued

| | C1 | C2 | C3 | C4 | C5 | C6 | C7 | C8 | C9 |
|---|---|---|---|---|---|---|---|---|---|
| Ex. 4.6 (% w/w) | 4.0 | 8.0 | — | — | — | — | — | — | — |
| Ex. 4.7 (% w/w) | — | 2.0 | 4.0 | — | — | — | — | — | 2.0 |
| Ex. 4.8 (% w/w) | — | 2.0 | 4.0 | — | — | — | — | — | — |
| Ex. 4.9 (% w/w) | — | 2.0 | 4.0 | — | — | — | — | — | — |
| Ex. 4.10 (% w/w) | — | 2.0 | 4.0 | — | — | — | — | — | — |
| Ex. 4.11 (% w/w) | — | 2.0 | 4.0 | — | — | — | — | — | — |
| Ex. 4.12 (% w/w) | — | 2.0 | 4.0 | — | — | — | — | — | — |
| Ex. 4.13 (% w/w) | — | — | 0.4 | — | — | — | — | — | 2.0 |
| Ex. 4.14 (% w/w) | — | — | 0.4 | — | — | — | — | — | — |
| Ex. 4.15 (% w/w) | — | — | 0.4 | — | — | — | — | — | — |
| Ex. 4.16 (% w/w) | — | — | 0.4 | — | — | — | — | — | — |
| Ex. 4.17 (% w/w) | — | — | 0.4 | — | — | — | — | — | — |
| Ex. 4.18 (% w/w) | — | — | 0.4 | — | — | — | — | — | — |
| Ex. 4.19 (% w/w) | — | — | — | 3.0 | 6.0 | — | — | — | 2.0 |
| Ex. 4.20 (% w/w) | — | — | — | 3.0 | 6.0 | — | — | — | — |
| Ex. 4.21 (% w/w) | — | — | — | 3.0 | 6.0 | — | — | — | — |
| Ex. 4.22 (% w/w) | — | — | — | 3.0 | 6.0 | — | — | — | — |
| Ex. 4.23 (% w/w) | — | — | — | 3.0 | 6.0 | — | — | — | — |
| Ex. 4.24 (% w/w) | — | — | — | 3.0 | 6.0 | — | — | — | — |
| Ex. 4.25 (% w/w) | — | — | — | — | 0.5 | — | — | — | 2.0 |
| Ex. 4.26 (% w/w) | — | — | — | — | 0.5 | — | — | — | — |
| Ex. 4.27 (% w/w) | — | — | — | — | 0.5 | — | — | — | — |
| Ex. 4.28 (% w/w) | — | — | — | — | 0.5 | — | — | — | — |
| Ex. 4.29 (% w/w) | — | — | — | — | 0.5 | — | — | — | — |
| Ex. 4.30 (% w/w) | — | — | — | — | 0.5 | — | — | — | — |
| Ex. 4.31 (% w/w) | — | — | — | — | — | 0.04 | 0.08 | — | 2.0 |
| Ex. 4.32 (% w/w) | — | — | — | — | — | 0.04 | 0.08 | — | — |
| Ex. 4.33 (% w/w) | — | — | — | — | — | 0.04 | 0.08 | — | — |
| Ex. 4.34 (% w/w) | — | — | — | — | — | 0.04 | 0.08 | — | — |
| Ex. 4.35 (% w/w) | — | — | — | — | — | 0.04 | 0.08 | — | — |
| Ex. 4.36 (% w/w) | — | — | — | — | — | 0.04 | 0.08 | — | — |
| Ex. 4.37 (% w/w) | — | — | — | — | — | — | 0.1 | 0.2 | 2.0 |
| Ex. 4.38 (% w/w) | — | — | — | — | — | — | 0.1 | 0.2 | — |
| Ex. 4.39 (% w/w) | — | — | — | — | — | — | 0.1 | 0.2 | — |
| Ex. 4.40 (% w/w) | — | — | — | — | — | — | 0.1 | 0.2 | — |
| Ex. 4.41 (% w/w) | — | — | — | — | — | — | 0.1 | 0.2 | — |
| Ex. 4.42 (% w/w) | — | — | — | — | — | — | 0.1 | 0.2 | — |

| Amount % (w/w) 5 mg | Content | | | | | | |
|---|---|---|---|---|---|---|---|
| | Levosalbutamol | Terbutalin 200 mcg | Pirbuterol 200 mcg | Bitolterol 370 mcg | Metaproterenol 650 mcg | Lactose + Mannitol | |
| Ex. 4.1 (% w/w) | — | — | — | — | — | 94.0 | 90.0 |
| Ex. 4.2 (% w/w) | 1.0 | — | — | — | — | 95.0 | 91.0 |
| Ex. 4.3 (% w/w) | — | 4.0 | — | — | — | 92.0 | 88.0 |
| Ex. 4.4 (% w/w) | — | — | 4.0 | — | — | 92.0 | 88.0 |
| Ex. 4.5 (% w/w) | — | — | — | 7.4 | — | 88.6 | 84.6 |
| Ex. 4.6 (% w/w) | — | — | — | — | 13.0 | 83.0 | 79.0 |
| Ex. 4.7 (% w/w) | — | — | — | — | — | 96.0 | 94.0 |
| Ex. 4.8 (% w/w) | 1.0 | — | — | — | — | 97.0 | 95.0 |
| Ex. 4.9 (% w/w) | — | 4.0 | — | — | — | 94.0 | 92.0 |
| Ex. 4.10 (% w/w) | — | — | 4.0 | — | — | 94.0 | 92.0 |
| Ex. 4.11 (% w/w) | — | — | — | 7.4 | — | 90.6 | 88.6 |
| Ex. 4.12 (% w/w) | — | — | — | — | 13.0 | 85.0 | 83.0 |
| Ex. 4.13 (% w/w) | — | — | — | — | — | | 97.6 |
| Ex. 4.14 (% w/w) | 1.0 | — | — | — | — | | 98.6 |
| Ex. 4.15 (% w/w) | — | 4.0 | — | — | — | | 95.6 |
| Ex. 4.16 (% w/w) | — | — | 4.0 | — | — | | 95.6 |
| Ex. 4.17 (% w/w) | — | — | — | 7.4 | — | | 92.2 |
| Ex. 4.18 (% w/w) | — | — | — | — | 13.0 | | 86.6 |
| Ex. 4.19 (% w/w) | — | — | — | — | — | 95.0 | 92.0 |
| Ex. 4.20 (% w/w) | 1.0 | — | — | — | — | 96.0 | 93.0 |
| Ex. 4.21 (% w/w) | — | 4.0 | — | — | — | 93.0 | 90.0 |
| Ex. 4.22 (% w/w) | — | — | 4.0 | — | — | 93.0 | 90.0 |
| Ex. 4.23 (% w/w) | — | — | — | 7.4 | — | 89.6 | 86.6 |
| Ex. 4.24 (% w/w) | — | — | — | — | 13.0 | 84.0 | 81.0 |
| Ex. 4.25 (% w/w) | — | — | — | — | — | | 97.5 |
| Ex. 4.26 (% w/w) | 1.0 | — | — | — | — | | 98.5 |
| Ex. 4.27 (% w/w) | — | 4.0 | — | — | — | | 95.5 |
| Ex. 4.28 (% w/w) | — | — | 4.0 | — | — | | 95.5 |
| Ex. 4.29 (% w/w) | — | — | — | 7.4 | — | | 92.1 |
| Ex. 4.30 (% w/w) | — | — | — | — | 13.0 | | 86.5 |
| Ex. 4.31 (% w/w) | — | — | — | — | — | 97.96 | 97.92 |
| Ex. 4.32 (% w/w) | 1.0 | — | — | — | — | 98.96 | 98.92 |
| Ex. 4.33 (% w/w) | — | 4.0 | — | — | — | 95.96 | 95.92 |
| Ex. 4.34 (% w/w) | — | — | 4.0 | — | — | 95.96 | 95.92 |
| Ex. 4.35 (% w/w) | — | — | — | 7.4 | — | 92.56 | 92.52 |
| Ex. 4.36 (% w/w) | — | — | — | — | 13.0 | 86.96 | 86.92 |
| Ex. 4.37 (% w/w) | — | — | — | — | — | 97.9 | 97.8 |

TABLE 4.1-continued

| | | | | | | | |
|---|---|---|---|---|---|---|---|
| Ex. 4.38 (% w/w) | 1.0 | — | — | — | — | 98.9 | 98.8 |
| Ex. 4.39 (% w/w) | — | 4.0 | — | — | — | 95.9 | 95.8 |
| Ex. 4.40 (% w/w) | — | — | 4.0 | — | — | 95.9 | 95.8 |
| Ex. 4.41 (% w/w) | — | — | — | 7.4 | — | 92.5 | 92.4 |
| Ex. 4.42 (% w/w) | — | — | — | — | 13.0 | 86.9 | 86.8 |

TABLE 4.2

| Amount % (w/w) 25 mg | Aklidinium | | Glycopyrronium | | Daratropium | indacaterol | | Vilanterol | Carmeterol | | Olodaterol | | Salbutamol |
|---|---|---|---|---|---|---|---|---|---|---|---|---|---|
| | | | | | | | | | | | | | Content |
| Ex. 4.1 (% w/w) | 0.8 | 1.6 | — | | — | — | | — | — | | — | | 0.4 |
| Ex. 4.2 (% w/w) | 0.8 | 1.6 | — | | — | — | | — | — | | — | | — |
| Ex. 4.3 (% w/w) | 0.8 | 1.6 | — | | — | — | | — | — | | — | | — |
| Ex. 4.4 (% w/w) | 0.8 | 1.6 | — | | — | — | | — | — | | — | | — |
| Ex. 4.5 (% w/w) | 0.8 | 1.6 | — | | — | — | | — | — | | — | | — |
| Ex. 4.6 (% w/w) | 0.8 | 1.6 | — | | — | — | | — | — | | — | | — |
| Ex. 4.7 (% w/w) | — | | 0.4 | 0.8 | — | — | | — | — | | — | | 0.4 |
| Ex. 4.8 (% w/w) | — | | 0.4 | 0.8 | — | — | | — | — | | — | | — |
| Ex. 4.9 (% w/w) | — | | 0.4 | 0.8 | — | — | | — | — | | — | | — |
| Ex. 4.10 (% w/w) | — | | 0.4 | 0.8 | — | — | | — | — | | — | | — |
| Ex. 4.11 (% w/w) | — | | 0.4 | 0.8 | — | — | | — | — | | — | | — |
| Ex. 4.12 (% w/w) | — | | 0.4 | 0.8 | — | — | | — | — | | — | | — |
| Ex. 4.13 (% w/w) | — | | — | | 0.08 | — | | — | — | | — | | 0.4 |
| Ex. 4.14 (% w/w) | — | | — | | 0.08 | — | | — | — | | — | | — |
| Ex. 4.15 (% w/w) | — | | — | | 0.08 | — | | — | — | | — | | — |
| Ex. 4.16 (% w/w) | — | | — | | 0.08 | — | | — | — | | — | | — |
| Ex. 4.17 (% w/w) | — | | — | | 0.08 | — | | — | — | | — | | — |
| Ex. 4.18 (% w/w) | — | | — | | 0.08 | — | | — | — | | — | | — |
| Ex. 4.19 (% w/w) | — | | — | | — | 0.6 | 1.2 | — | — | | — | | — |
| Ex. 4.20 (% w/w) | — | | — | | — | 0.6 | 1.2 | — | — | | — | | — |
| Ex. 4.21 (% w/w) | — | | — | | — | 0.6 | 1.2 | — | — | | — | | — |
| Ex. 4.22 (% w/w) | — | | — | | — | 0.6 | 1.2 | — | — | | — | | — |
| Ex. 4.23 (% w/w) | — | | — | | — | 0.6 | 1.2 | — | — | | — | | — |
| Ex. 4.24 (% w/w) | — | | — | | — | 0.6 | 1.2 | — | — | | — | | — |
| Ex. 4.25 (% w/w) | — | | — | | — | — | | 0.1 | — | | — | | 0.4 |
| Ex. 4.26 (% w/w) | — | | — | | — | — | | 0.1 | — | | — | | — |
| Ex. 4.27 (% w/w) | — | | — | | — | — | | 0.1 | — | | — | | — |
| Ex. 4.28 (% w/w) | — | | — | | — | — | | 0.1 | — | | — | | — |
| Ex. 4.29 (% w/w) | — | | — | | — | — | | 0.1 | — | | — | | — |
| Ex. 4.30 (% w/w) | — | | — | | — | — | | 0.1 | — | | — | | — |
| Ex. 4.31 (% w/w) | — | | — | | — | — | | — | 0.01 | 0.02 | — | | 0.4 |
| Ex. 4.32 (% w/w) | — | | — | | — | — | | — | 0.01 | 0.02 | — | | — |
| Ex. 4.33 (% w/w) | — | | — | | — | — | | — | 0.01 | 0.02 | — | | — |
| Ex. 4.34 (% w/w) | — | | — | | — | — | | — | 0.01 | 0.02 | — | | — |
| Ex. 4.35 (% w/w) | — | | — | | — | — | | — | 0.01 | 0.02 | — | | — |
| Ex. 4.36 (% w/w) | — | | — | | — | — | | — | 0.01 | 0.02 | — | | — |
| Ex. 4.37 (% w/w) | — | | — | | — | — | | — | — | | 0.02 | 0.04 | 0.4 |
| Ex. 4.38 (% w/w) | — | | — | | — | — | | — | — | | 0.02 | 0.04 | — |
| Ex. 4.39 (% w/w) | — | | — | | — | — | | — | — | | 0.02 | 0.04 | — |
| Ex. 4.40 (% w/w) | — | | — | | — | — | | — | — | | 0.02 | 0.04 | — |
| Ex. 4.41 (% w/w) | — | | — | | — | — | | — | — | | 0.02 | 0.04 | — |
| Ex. 4.42 (% w/w) | — | | — | | — | — | | — | — | | 0.02 | 0.04 | — |

| Amount % (w/w) 25 mg | Levosalbutamol | Terbutaline 200 mcg | Pirbuterol 200 mcg | Bitolterol 370 mcg | Metaproterenol 650 mcg | Lactose + Mannitol | |
|---|---|---|---|---|---|---|---|
| Ex. 4.1 (% w/w) | — | — | — | — | — | 98.8 | 98.0 |
| Ex. 4.2 (% w/w) | 0.2 | — | — | — | — | 99.0 | 98.2 |
| Ex. 4.3 (% w/w) | — | 0.8 | — | — | — | 98.4 | 97.6 |
| Ex. 4.4 (% w/w) | — | — | 0.8 | — | — | 98.4 | 97.6 |
| Ex. 4.5 (% w/w) | — | — | — | 1.5 | — | 97.7 | 96.9 |
| Ex. 4.6 (% w/w) | — | — | — | — | 2.6 | 96.6 | 95.8 |
| Ex. 4.7 (% w/w) | — | — | — | — | — | 99.2 | 98.8 |
| Ex. 4.8 (% w/w) | 0.2 | — | — | — | — | 99.4 | 99.0 |
| Ex. 4.9 (% w/w) | — | 0.8 | — | — | — | 98.8 | 98.4 |
| Ex. 4.10 (% w/w) | — | — | 0.8 | — | — | 98.8 | 98.4 |
| Ex. 4.11 (% w/w) | — | — | — | 1.5 | — | 98.1 | 97.7 |
| Ex. 4.12 (% w/w) | — | — | — | — | 2.6 | 97.0 | 96.6 |
| Ex. 4.13 (% w/w) | — | — | — | — | — | 99.52 | |
| Ex. 4.14 (% w/w) | 0.2 | — | — | — | — | 99.72 | |
| Ex. 4.15 (% w/w) | — | 0.8 | — | — | — | 99.12 | |
| Ex. 4.16 (% w/w) | — | — | 0.8 | — | — | 99.12 | |

TABLE 4.2-continued

|  |  |  |  |  |  |  |
|---|---|---|---|---|---|---|
| Ex. 4.17 (% w/w) | — | — | — | 1.5 | — | 98.42 |
| Ex. 4.18 (% w/w) | — | — | — | — | 2.6 | 97.32 |
| Ex. 4.19 (% w/w) | — | — | — | — | — | 99.0 98.4 |
| Ex. 4.20 (% w/w) | 0.2 | — | — | — | — | 99.2 98.6 |
| Ex. 4.21 (% w/w) | — | 0.8 | — | — | — | 98.6 98.0 |
| Ex. 4.22 (% w/w) | — | — | 0.8 | — | — | 98.6 98.0 |
| Ex. 4.23 (% w/w) | — | — | — | 1.5 | — | 97.9 97.3 |
| Ex. 4.24 (% w/w) | — | — | — | — | 2.6 | 96.8 96.2 |
| Ex. 4.25 (% w/w) | — | — | — | — | — | 99.5 |
| Ex. 4.26 (% w/w) | 0.2 | — | — | — | — | 99.7 |
| Ex. 4.27 (% w/w) | — | 0.8 | — | — | — | 99.1 |
| Ex. 4.28 (% w/w) | — | — | 0.8 | — | — | 99.1 |
| Ex. 4.29 (% w/w) | — | — | — | 1.5 | — | 98.4 |
| Ex. 4.30 (% w/w) | — | — | — | — | 2.6 | 97.3 |
| Ex. 4.31 (% w/w) | — | — | — | — | — | 99.59 99.58 |
| Ex. 4.32 (% w/w) | 0.2 | — | — | — | — | 99.79 99.78 |
| Ex. 4.33 (% w/w) | — | 0.8 | — | — | — | 99.19 99.18 |
| Ex. 4.34 (% w/w) | — | — | 0.8 | — | — | 99.19 99.18 |
| Ex. 4.35 (% w/w) | — | — | — | 1.5 | — | 98.49 98.48 |
| Ex. 4.36 (% w/w) | — | — | — | — | 2.6 | 97.39 97.38 |
| Ex. 4.37 (% w/w) | — | — | — | — | — | 99.58 99.56 |
| Ex. 4.38 (% w/w) | 0.2 | — | — | — | — | 99.78 99.76 |
| Ex. 4.39 (% w/w) | — | 0.8 | — | — | — | 99.18 99.14 |
| Ex. 4.40 (% w/w) | — | — | 0.8 | — | — | 99.18 99.14 |
| Ex. 4.41 (% w/w) | — | — | — | 1.5 | — | 98.48 98.44 |
| Ex. 4.42 (% w/w) | — | — | — | — | 2.6 | 97.38 97.34 |

Examples—E a)

| Content | Amount % (w/w) |
|---|---|
| Muscarinic receptor antagonist | |
| Beta-2 adrenerjik agonist | |
| Corticosteroid | |
| Lactose + mannitol | |

TABLE 6.1

| Amount % (w/w) | Content | | | | | | |
|---|---|---|---|---|---|---|---|
| 5 mg | Aklidinyum | Glycopyrronium | Daratropium | indacaterol | Vilanterol | Carmeterol | Olodaterol |
| Ex. 5.1 (% w/w) | 4.0 | 8.0 | — | — | — | — | — |
| Ex. 5.2 (% w/w) | 4.0 | 8.0 | — | — | — | — | — |
| Ex. 5.3 (% w/w) | 4.0 | 8.0 | — | — | — | — | — |
| Ex. 5.4 (% w/w) | 4.0 | 8.0 | — | — | — | — | — |
| Ex. 5.5 (% w/w) | 4.0 | 8.0 | — | — | — | — | — |
| Ex. 5.9 (% w/w) | — | 2.0 | 4.0 | — | — | — | — |
| Ex. 5.10 (% w/w) | — | 2.0 | 4.0 | — | — | — | — |
| Ex. 5.11 (% w/w) | — | 2.0 | 4.0 | — | — | — | — |
| Ex. 5.12 (% w/w) | — | 2.0 | 4.0 | — | — | — | — |
| Ex. 5.13 (% w/w) | — | 2.0 | 4.0 | — | — | — | — |
| Ex. 5.17 (% w/w) | — | — | 0.4 | — | — | — | — |
| Ex. 5.18 (% w/w) | — | — | 0.4 | — | — | — | — |
| Ex. 5.19 (% w/w) | — | — | 0.4 | — | — | — | — |
| Ex. 5.20 (% w/w) | — | — | 0.4 | — | — | — | — |
| Ex. 5.21 (% w/w) | — | — | 0.4 | — | — | — | — |
| Ex. 5.25 (% w/w) | — | — | — | 3.0 | 6.0 | — | — |
| Ex. 5.26 (% w/w) | — | — | — | 3.0 | 6.0 | — | — |
| Ex. 5.27 (% w/w) | — | — | — | 3.0 | 6.0 | — | — |
| Ex. 5.28 (% w/w) | — | — | — | 3.0 | 6.0 | — | — |
| Ex. 5.29 (% w/w) | — | — | — | 3.0 | 6.0 | — | — |
| Ex. 5.33 (% w/w) | — | — | — | — | 0.5 | — | — |
| Ex. 5.34 (% w/w) | — | — | — | — | 0.5 | — | — |
| Ex. 5.35 (% w/w) | — | — | — | — | 0.5 | — | — |
| Ex. 5.36 (% w/w) | — | — | — | — | 0.5 | — | — |
| Ex. 5.37 (% w/w) | — | — | — | — | 0.5 | — | — |
| Ex. 5.41 (% w/w) | — | — | — | — | — | 0.04 | 0.08 |
| Ex. 5.42 (% w/w) | — | — | — | — | — | 0.04 | 0.08 |
| Ex. 5.43 (% w/w) | — | — | — | — | — | 0.04 | 0.08 |

TABLE 6.1-continued

| | | | | | | | | |
|---|---|---|---|---|---|---|---|---|
| Ex. 5.44 (% w/w) | — | — | — | — | — | 0.04 | 0.08 | — |
| Ex. 5.45 (% w/w) | — | — | — | — | — | 0.04 | 0.08 | — |
| Ex. 5.49 (% w/w) | — | — | — | — | — | — | 0.1 | 0.2 |
| Ex. 5.50 (% w/w) | — | — | — | — | — | — | 0.1 | 0.2 |
| Ex. 5.51 (% w/w) | — | — | — | — | — | — | 0.1 | 0.2 |
| Ex. 5.52 (% w/w) | — | — | — | — | — | — | 0.1 | 0.2 |
| Ex. 5.53 (% w/w) | — | — | — | — | — | — | 0.1 | 0.2 |

| Amount % (w/w) | Content | | | | | | |
|---|---|---|---|---|---|---|---|
| 5 mg | Flutikason | Siklesoinid | Budesonid | Mometazon | Beklometazon | Lactose + Mannitol | |
| Ex. 5.1 (% w/w) | 2.0  10.0 | — | — | — | — | 94.0 | 82.0 |
| Ex. 5.2 (% w/w) | — | 4.0 | — | — | — | — | 88.0 |
| Ex. 5.3 (% w/w) | — | — | 4.0  8.0 | — | — | 92.0 | 84.0 |
| Ex. 5.4 (% w/w) | — | — | — | 2.0  4.0 | — | 94.0 | 88.0 |
| Ex. 5.5 (% w/w) | — | — | — | — | 2.0  8.0 | 94.0 | 84.0 |
| Ex. 5.9 (% w/w) | 2.0  10.0 | — | — | — | — | 96.0 | 86.0 |
| Ex. 5.10 (% w/w) | — | 4.0 | — | — | — | 94.0 | 92.0 |
| Ex. 5.11 (% w/w) | — | — | 4.0  8.0 | — | — | 94.0 | 88.0 |
| Ex. 5.12 (% w/w) | — | — | — | 2.0  4.0 | — | 96.0 | 92.0 |
| Ex. 5.13 (% w/w) | — | — | — | — | 2.0  8.0 | 96.0 | 88.0 |
| Ex. 5.17 (% w/w) | — 10.0 | — | — | — | — | 97.6 | 89.6 |
| Ex. 5.18 (% w/w) | — | 4.0 | — | — | — | 95.6 | |
| Ex. 5.19 (% w/w) | — | — | 4.0  8.0 | — | — | 95.6 | 91.6 |
| Ex. 5.20 (% w/w) | — | — | — | 2.0  4.0 | — | 97.6 | 95.6 |
| Ex. 5.21 (% w/w) | — | — | — | — | 2.0  8.0 | 97.6 | 91.6 |
| Ex. 5.25 (% w/w) | 2.0  10.0 | — | — | — | — | 95.0 | 84.0 |
| Ex. 5.26 (% w/w) | — | 4.0 | — | — | — | 93.0 | 90.0 |
| Ex. 5.27 (% w/w) | — | — | 4.0  8.0 | — | — | 93.0 | 96.0 |
| Ex. 5.28 (% w/w) | — | — | — | 2.0  4.0 | — | 95.0 | 90.0 |
| Ex. 5.29 (% w/w) | — | — | — | — | 2.0  8.0 | 95.0 | 86.0 |
| Ex. 5.33 (% w/w) | 2.0  10.0 | — | — | — | — | 97.5 | 89.5 |
| Ex. 5.34 (% w/w) | — | 4.0 | — | — | — | 95.5 | |
| Ex. 5.35 (% w/w) | — | — | 4.0  8.0 | — | — | 95.5 | 91.5 |
| Ex. 5.36 (% w/w) | — | — | — | 2.0  4.0 | — | 97.5 | 95.5 |
| Ex. 5.37 (% w/w) | — | — | — | — | 2.0  8.0 | 97.5 | 91.5 |
| Ex. 5.41 (% w/w) | 2.0  10.0 | — | — | — | — | 97.96 | 89.92 |
| Ex. 5.42 (% w/w) | — | 4.0 | — | — | — | 95.96 | |
| Ex. 5.43 (% w/w) | — | — | 4.0  8.0 | — | — | 95.96 | 91.96 |
| Ex. 5.44 (% w/w) | — | — | — | 2.0  4.0 | — | 97.96 | 95.96 |
| Ex. 5.45 (% w/w) | — | — | — | — | 2.0  8.0 | 97.96 | 91.97 |
| Ex. 5.49 (% w/w) | 2.0  10.0 | — | — | — | — | 97.9 | 89.8 |
| Ex. 5.50 (% w/w) | — | 4.0 | — | — | — | 95.9 | 95.8 |
| Ex. 5.51 (% w/w) | — | — | 4.0  8.0 | — | — | 95.9 | 91.8 |
| Ex. 5.52 (% w/w) | — | — | — | 2.0  4.0 | — | 97.9 | 95.8 |
| Ex. 5.53 (% w/w) | — | — | — | — | 2.0  8.0 | 97.9 | 91.8 |

TABLE 6.2

| Amount % (w/w) | Content | | | | | | |
|---|---|---|---|---|---|---|---|
| 25 mg | Aklidinyum | Glycopyrronium | Daratropium | indacaterol | Vilanterol | Carmeterol | Olodaterol |
| Ex. 5.1 (% w/w) | 0.8 | 1.6 | — | — | — | — | — |
| Ex. 5.2 (% w/w) | 0.8 | 1.6 | — | — | — | — | — |
| Ex. 5.3 (% w/w) | 0.8 | 1.6 | — | — | — | — | — |
| Ex. 5.4 (% w/w) | 0.8 | 1.6 | — | — | — | — | — |
| Ex. 5.5 (% w/w) | 0.8 | 1.6 | — | — | — | — | — |
| Ex. 5.9 (% w/w) | — | 0.4  0.8 | — | — | — | — | — |
| Ex. 5.10 (% w/w) | — | 0.4  0.8 | — | — | — | — | — |
| Ex. 5.11 (% w/w) | — | 0.4  0.8 | — | — | — | — | — |
| Ex. 5.12 (% w/w) | — | 0.4  0.8 | — | — | — | — | — |
| Ex. 5.13 (% w/w) | — | 0.4  0.8 | — | — | — | — | — |
| Ex. 5.17 (% w/w) | — | — | 0.08 | — | — | — | — |
| Ex. 5.18 (% w/w) | — | — | 0.08 | — | — | — | — |
| Ex. 5.19 (% w/w) | — | — | 0.08 | — | — | — | — |
| Ex. 5.20 (% w/w) | — | — | 0.08 | — | — | — | — |
| Ex. 5.21 (% w/w) | — | — | 0.08 | — | — | — | — |
| Ex. 5.25 (% w/w) | — | — | — | 0.6  1.2 | — | — | — |
| Ex. 5.26 (% w/w) | — | — | — | 0.6  1.2 | — | — | — |
| Ex. 5.27 (% w/w) | — | — | — | 0.6  1.2 | — | — | — |
| Ex. 5.28 (% w/w) | — | — | — | 0.6  1.2 | — | — | — |
| Ex. 5.29 (% w/w) | — | — | — | 0.6  1.2 | — | — | — |
| Ex. 5.33 (% w/w) | — | — | — | — | 0.1 | — | — |

TABLE 6.2-continued

| | | | | | | | | |
|---|---|---|---|---|---|---|---|---|
| Ex. 5.34 (% w/w) | — | — | — | — | 0.1 | | | — |
| Ex. 5.35 (% w/w) | — | — | — | — | 0.1 | | | — |
| Ex. 5.36 (% w/w) | — | — | — | — | 0.1 | | | — |
| Ex. 5.37 (% w/w) | — | — | — | — | 0.1 | | | — |
| Ex. 5.41 (% w/w) | — | — | — | — | — | 0.01 | 0.02 | — |
| Ex. 5.42 (% w/w) | — | — | — | — | — | 0.01 | 0.02 | — |
| Ex. 5.43 (% w/w) | — | — | — | — | — | 0.01 | 0.02 | — |
| Ex. 5.44 (% w/w) | — | — | — | — | — | 0.01 | 0.02 | — |
| Ex. 5.45 (% w/w) | — | — | — | — | — | 0.01 | 0.02 | — |
| Ex. 5.49 (% w/w) | — | — | — | — | — | — | 0.02 | 0.04 |
| Ex. 5.50 (% w/w) | — | — | — | — | — | — | 0.02 | 0.04 |
| Ex. 5.51 (% w/w) | — | — | — | — | — | — | 0.02 | 0.04 |
| Ex. 5.52 (% w/w) | — | — | — | — | — | — | 0.02 | 0.04 |
| Ex. 5.53 (% w/w) | — | — | — | — | — | — | 0.02 | 0.04 |

| Amount % (w/w) 25 mg | Content | | | | | | |
|---|---|---|---|---|---|---|---|
| | Fluticasone | Siklesoinid | Budesonid | Mometazon | Beklametazon | Lactose + Mannitol | |
| Ex. 5.1 (% w/w) | 0.4 2.0 | — | — | — | — | 98.8 | 96.4 |
| Ex. 5.2 (% w/w) | — | 0.8 | — | — | — | — | 97.6 |
| Ex. 5.3 (% w/w) | — | — | 0.8 1.6 | — | — | 98.4 | 96.8 |
| Ex. 5.4 (% w/w) | — | — | — | 0.4 0.8 | — | 98.8 | 97.6 |
| Ex. 5.5 (% w/w) | — | — | — | — | 0.4 1.6 | 99.88 | |
| Ex. 5.9 (% w/w) | 0.4 | — | — | — | — | 99.2 | 97.2 |
| Ex. 5.10 (% w/w) | — | 0.8 | — | — | — | 98.8 | 98.4 |
| Ex. 5.11 (% w/w) | — | — | 0.8 1.6 | — | — | 98.2 | 97.6 |
| Ex. 5.12 (% w/w) | — | — | — | 0.4 0.8 | — | 99.2 | 97.6 |
| Ex. 5.13 (% w/w) | — | — | — | — | 0.4 1.6 | 99.2 | 97.6 |
| Ex. 5.17 (% w/w) | — 2.0 | — | — | — | — | 99.52 | 97.92 |
| Ex. 5.18 (% w/w) | — | 0.8 | — | — | — | 99.12 | |
| Ex. 5.19 (% w/w) | — | — | 0.8 1.6 | — | — | 99.12 | 98.32 |
| Ex. 5.20 (% w/w) | — | — | — | 0.4 0.8 | — | 99.52 | 99.12 |
| Ex. 5.21 (% w/w) | — | — | — | — | 0.4 1.6 | 99.52 | 98.32 |
| Ex. 5.25 (% w/w) | 0.4 2.0 | — | — | — | — | 99.0 | 96.8 |
| Ex. 5.26 (% w/w) | — | 0.8 | — | — | — | 98.6 | 98.0 |
| Ex. 5.27 (% w/w) | — | — | 0.8 1.6 | — | — | 98.6 | 97.2 |
| Ex. 5.28 (% w/w) | — | — | — | 0.4 0.8 | — | 99.0 | 98.0 |
| Ex. 5.29 (% w/w) | — | — | — | — | 0.4 1.6 | 99.0 | 97.2 |
| Ex. 5.33 (% w/w) | 0.4 2.0 | — | — | — | — | 99.5 | 97.9 |
| Ex. 5.34 (% w/w) | — | 0.8 | — | — | — | 99.1 | |
| Ex. 5.35 (% w/w) | — | — | 0.8 1.6 | — | — | 99.1 | 98.3 |
| Ex. 5.36 (% w/w) | — | — | — | 0.4 0.8 | — | 99.5 | 99.1 |
| Ex. 5.37 (% w/w) | — | — | — | — | 0.4 1.6 | 99.5 | 98.3 |
| Ex. 5.41 (% w/w) | 0.4 2.0 | — | — | — | — | 99.59 | 97.98 |
| Ex. 5.42 (% w/w) | — | 0.8 | — | — | — | 99.19 | 99.18 |
| Ex. 5.43 (% w/w) | — | — | 0.8 1.6 | — | — | 99.19 | 98.38 |
| Ex. 5.44 (% w/w) | — | — | — | 0.4 0.8 | — | 99.59 | 99.18 |
| Ex. 5.45 (% w/w) | — | — | — | — | 0.4 1.6 | 99.59 | 98.38 |
| Ex. 5.49 (% w/w) | 0.4 2.0 | — | — | — | — | 99.58 | 97.96 |
| Ex. 5.50 (% w/w) | — | 0.8 | — | — | — | 99.18 | 99.16 |
| Ex. 5.51 (% w/w) | — | — | 0.8 1.6 | — | — | 99.18 | 98.36 |
| Ex. 5.52 (% w/w) | — | — | — | 0.4 0.8 | — | 99.58 | 99.16 |
| Ex. 5.53 (% w/w) | — | — | — | — | 0.4 1.6 | 99.58 | 98.36 |

Örnek—F

| Content | Amount % (w/w) |
|---|---|
| Muscarinic receptor antagonist | |
| Corticosteroid | |
| Lactose + mannitol | |

TABLE 7.1

| Amount % (w/w) 5 mg | Content | | | | | | |
|---|---|---|---|---|---|---|---|
| | Aklidinyum | Glycopyrronium | Daratropium | Tiotropium | ipratropium | Oxitropium | Fluticasone |
| Ex. 5.1 (% w/w) | 4.0 | 8.0 | — | — | — | — | — 2.0 10.0 |
| Ex. 5.2 (% w/w) | 4.0 | 8.0 | — | — | — | — | — |
| Ex. 5.3 (% w/w) | 4.0 | 8.0 | — | — | — | — | — |

TABLE 7.1-continued

| | | | | | | | | | |
|---|---|---|---|---|---|---|---|---|---|
| Ex. 5.4 (% w/w) | 4.0 | 8.0 | — | — | — | — | — | — | — |
| Ex. 5.5 (% w/w) | 4.0 | 8.0 | — | — | — | — | — | — | — |
| Ex. 5.9 (% w/w) | — | 2.0 | 4.0 | — | — | — | — | 2.0 | 10.0 |
| Ex. 5.10 (% w/w) | — | 2.0 | 4.0 | — | — | — | — | — | — |
| Ex. 5.11 (% w/w) | — | 2.0 | 4.0 | — | — | — | — | — | — |
| Ex. 5.12 (% w/w) | — | 2.0 | 4.0 | — | — | — | — | — | — |
| Ex. 5.13 (% w/w) | — | 2.0 | 4.0 | — | — | — | — | — | — |
| Ex. 5.17 (% w/w) | — | — | 0.4 | — | — | — | — | — | 10.0 |
| Ex. 5.18 (% w/w) | — | — | 0.4 | — | — | — | — | — | — |
| Ex. 5.19 (% w/w) | — | — | 0.4 | — | — | — | — | — | — |
| Ex. 5.20 (% w/w) | — | — | 0.4 | — | — | — | — | — | — |
| Ex. 5.21 (% w/w) | — | — | 0.4 | — | — | — | — | — | — |
| Ex. 5.25 (% w/w) | — | — | — | 0.36 | — | — | — | 2.0 | 10.0 |
| Ex. 5.26 (% w/w) | — | — | — | 0.36 | — | — | — | — | — |
| Ex. 5.27 (% w/w) | — | — | — | 0.36 | — | — | — | — | — |
| Ex. 5.28 (% w/w) | — | — | — | 0.36 | — | — | — | — | — |
| Ex. 5.29 (% w/w) | — | — | — | 0.36 | — | — | — | — | — |
| Ex. 5.33 (% w/w) | — | — | — | — | 3 | 6 | — | 2.0 | 10.0 |
| Ex. 5.34 (% w/w) | — | — | — | — | 3 | 6 | — | — | — |
| Ex. 5.35 (% w/w) | — | — | — | — | 3 | 6 | — | — | — |
| Ex. 5.36 (% w/w) | — | — | — | — | 3 | 6 | — | — | — |
| Ex. 5.37 (% w/w) | — | — | — | — | 3 | 6 | — | — | — |
| Ex. 5.41 (% w/w) | — | — | — | — | — | — | 4 | 2.0 | 10.0 |
| Ex. 5.42 (% w/w) | — | — | — | — | — | — | 4 | — | — |
| Ex. 5.43 (% w/w) | — | — | — | — | — | — | 4 | — | — |
| Ex. 5.44 (% w/w) | — | — | — | — | — | — | 4 | — | — |
| Ex. 5.45 (% w/w) | — | — | — | — | — | — | 4 | — | — |
| Ex. 5.49 (% w/w) | — | — | — | — | — | — | — | 2.0 | 10.0 |
| Ex. 5.50 (% w/w) | — | — | — | — | — | — | — | — | — |
| Ex. 5.51 (% w/w) | — | — | — | — | — | — | — | — | — |
| Ex. 5.52 (% w/w) | — | — | — | — | — | — | — | — | — |
| Ex. 5.53 (% w/w) | — | — | — | — | — | — | — | — | — |

| Amount % (w/w) | Content | | | | | |
|---|---|---|---|---|---|---|
| 5 mg | Ciclesonide | Budesonid | | Mometazon | | Beklametazon | | Lactose + Mannitol | |
| Ex. 5.1 (% w/w) | — | — | | — | | — | | 94.0 | 82.0 |
| Ex. 5.2 (% w/w) | 4.0 | — | | — | | — | | — | 88.0 |
| Ex. 5.3 (% w/w) | — | 4.0 | 8.0 | — | | — | | 92.0 | 84.0 |
| Ex. 5.4 (% w/w) | — | — | | 2.0 | 4.0 | — | | 94.0 | 88.0 |
| Ex. 5.5 (% w/w) | — | — | | — | | 2.0 | 8.0 | 94.0 | 84.0 |
| Ex. 5.9 (% w/w) | — | — | | — | | — | | 96.0 | 86.0 |
| Ex. 5.10 (% w/w) | 4.0 | — | | — | | — | | 94.0 | 92.0 |
| Ex. 5.11 (% w/w) | — | 4.0 | 8.0 | — | | — | | 94.0 | 88.0 |
| Ex. 5.12 (% w/w) | — | — | | 2.0 | 4.0 | — | | 96.0 | 92.0 |
| Ex. 5.13 (% w/w) | — | — | | — | | 2.0 | 8.0 | 96.0 | 88.0 |
| Ex. 5.17 (% w/w) | — | — | | — | | — | | 97.6 | 89.6 |
| Ex. 5.18 (% w/w) | 4.0 | — | | — | | — | | 95.6 | |
| Ex. 5.19 (% w/w) | — | 4.0 | 8.0 | — | | — | | 95.6 | 91.6 |
| Ex. 5.20 (% w/w) | — | — | | 2.0 | 4.0 | — | | 97.6 | 95.6 |
| Ex. 5.21 (% w/w) | — | — | | — | | 2.0 | 8.0 | 97.6 | 91.6 |
| Ex. 5.25 (% w/w) | — | — | | — | | — | | 97.64 | 89.64 |
| Ex. 5.26 (% w/w) | 4.0 | — | | — | | — | | 95.64 | |
| Ex. 5.27 (% w/w) | — | 4.0 | 8.0 | — | | — | | 95.64 | 91.64 |
| Ex. 5.28 (% w/w) | — | — | | 2.0 | 4.0 | — | | 97.64 | 95.64 |
| Ex. 5.29 (% w/w) | — | — | | — | | 2.0 | 8.0 | 97.64 | 91.64 |
| Ex. 5.33 (% w/w) | — | — | | — | | — | | 97.5 | 89.5 |
| Ex. 5.34 (% w/w) | 4.0 | — | | — | | — | | 93 | 90 |
| Ex. 5.35 (% w/w) | — | 4.0 | 8.0 | — | | — | | 93 | 86 |
| Ex. 5.36 (% w/w) | — | — | | 2.0 | 4.0 | — | | 95 | 90 |
| Ex. 5.37 (% w/w) | — | — | | — | | 2.0 | 8.0 | 95 | 86 |
| Ex. 5.41 (% w/w) | — | — | | — | | — | | 94 | 86 |
| Ex. 5.42 (% w/w) | 4.0 | — | | — | | — | | — | 92 |
| Ex. 5.43 (% w/w) | — | 4.0 | 8.0 | — | | — | | 92 | 88 |
| Ex. 5.44 (% w/w) | — | — | | 2.0 | 4.0 | — | | 94 | 92 |
| Ex. 5.45 (% w/w) | — | — | | — | | 2.0 | 8.0 | 96 | 88 |
| Ex. 5.49 (% w/w) | — | — | | — | | — | | 97.9 | 89.8 |
| Ex. 5.50 (% w/w) | 4.0 | — | | — | | — | | 95.9 | 95.8 |
| Ex. 5.51 (% w/w) | — | 4.0 | 8.0 | — | | — | | 95.9 | 91.8 |
| Ex. 5.52 (% w/w) | — | — | | 2.0 | 4.0 | — | | 97.9 | 95.8 |
| Ex. 5.53 (% w/w) | — | — | | — | | 2.0 | 8.0 | 97.9 | 91.8 |

TABLE 7.2

| Amount % (w/w) 25 mg | Content | | | | | | | | | | | |
|---|---|---|---|---|---|---|---|---|---|---|---|---|
| | Aklidinyum | | Glycopyrronium | | Daratropium | Tiotropium | ipratropium | | Oxitropium | Fluticazon | | |
| Ex. 5.1 (% w/w) | 0.8 | 1.6 | — | | — | — | — | | — | 0.4 | 2.0 | |
| Ex. 5.2 (% w/w) | 0.8 | 1.6 | — | | — | — | — | | — | — | | |
| Ex. 5.3 (% w/w) | 0.8 | 1.6 | — | | — | — | — | | — | — | | |
| Ex. 5.4 (% w/w) | 0.8 | 1.6 | — | | — | — | — | | — | — | | |
| Ex. 5.5 (% w/w) | 0.8 | 1.6 | — | | — | — | — | | — | — | | |
| Ex. 5.9 (% w/w) | — | | 0.4 | 0.8 | — | — | — | | — | 0.4 | | |
| Ex. 5.10 (% w/w) | — | | 0.4 | 0.8 | — | — | — | | — | — | | |
| Ex. 5.11 (% w/w) | — | | 0.4 | 0.8 | — | — | — | | — | — | | |
| Ex. 5.12 (% w/w) | — | | 0.4 | 0.8 | — | — | — | | — | — | | |
| Ex. 5.13 (% w/w) | — | | 0.4 | 0.8 | — | — | — | | — | — | | |
| Ex. 5.17 (% w/w) | — | | — | | 0.08 | — | — | | — | — | 2.0 | |
| Ex. 5.18 (% w/w) | — | | — | | 0.08 | — | — | | — | — | | |
| Ex. 5.19 (% w/w) | — | | — | | 0.08 | — | — | | — | — | | |
| Ex. 5.20 (% w/w) | — | | — | | 0.08 | — | — | | — | — | | |
| Ex. 5.21 (% w/w) | — | | — | | 0.08 | — | — | | — | — | | |
| Ex. 5.25 (% w/w) | — | | — | | — | 0.072 | — | | — | 0.4 | 2.0 | |
| Ex. 5.26 (% w/w) | — | | — | | — | 0.072 | — | | — | — | | |
| Ex. 5.27 (% w/w) | — | | — | | — | 0.072 | — | | — | — | | |
| Ex. 5.28 (% w/w) | — | | — | | — | 0.072 | — | | — | — | | |
| Ex. 5.29 (% w/w) | — | | — | | — | 0.072 | — | | — | — | | |
| Ex. 5.33 (% w/w) | — | | — | | — | — | 3 | 6 | — | 0.4 | 2.0 | |
| Ex. 5.34 (% w/w) | — | | — | | — | — | 3 | 6 | — | — | | |
| Ex. 5.35 (% w/w) | — | | — | | — | — | 3 | 6 | — | — | | |
| Ex. 5.36 (% w/w) | — | | — | | — | — | 3 | 6 | — | — | | |
| Ex. 5.37 (% w/w) | — | | — | | — | — | 3 | 6 | — | — | | |
| Ex. 5.41 (% w/w) | — | | — | | — | — | — | | 0.8 | 0.4 | 2.0 | |
| Ex. 5.42 (% w/w) | — | | — | | — | — | — | | 0.8 | — | | |
| Ex. 5.43 (% w/w) | — | | — | | — | — | — | | 0.8 | — | | |
| Ex. 5.44 (% w/w) | — | | — | | — | — | — | | 0.8 | — | | |
| Ex. 5.45 (% w/w) | — | | — | | — | — | — | | 0.8 | — | | |
| Ex. 5.49 (% w/w) | — | | — | | — | — | — | | — | 0.4 | 2.0 | |
| Ex. 5.50 (% w/w) | — | | — | | — | — | — | | — | — | | |
| Ex. 5.51 (% w/w) | — | | — | | — | — | — | | — | — | | |
| Ex. 5.52 (% w/w) | — | | — | | — | — | — | | — | — | | |
| Ex. 5.53 (% w/w) | — | | — | | — | — | — | | — | — | | |

| Amount % (w/w) 25 mg | Content | | | | | | | |
|---|---|---|---|---|---|---|---|---|
| | Ciclesonide | Budesonid | | Mometason | | Beklametazon | | Lactose + Mannitol |
| Ex. 5.1 (% w/w) | — | — | | — | | — | | 98.8 96.4 |
| Ex. 5.2 (% w/w) | 0.8 | — | | — | | — | | 97.6 |
| Ex. 5.3 (% w/w) | — | 0.8 | 1.6 | — | | — | | 98.4 96.8 |
| Ex. 5.4 (% w/w) | — | — | | 0.4 | 0.8 | — | | 98.8 97.6 |
| Ex. 5.5 (% w/w) | — | — | | — | | 0.4 | 1.6 | 99.88 |
| Ex. 5.9 (% w/w) | — | — | | — | | — | | 99.2 97.2 |
| Ex. 5.10 (% w/w) | 0.8 | — | | — | | — | | 98.8 98.4 |
| Ex. 5.11 (% w/w) | — | 0.8 | 1.6 | — | | — | | 98.2 97.6 |
| Ex. 5.12 (% w/w) | — | — | | 0.4 | 0.8 | — | | 99.2 97.6 |
| Ex. 5.13 (% w/w) | — | — | | — | | 0.4 | 1.6 | 99.2 97.6 |
| Ex. 5.17 (% w/w) | — | — | | — | | — | | 99.52 97.92 |
| Ex. 5.18 (% w/w) | 0.8 | — | | — | | — | | 99.12 |
| Ex. 5.19 (% w/w) | — | 0.8 | 1.6 | — | | — | | 99.12 98.32 |
| Ex. 5.20 (% w/w) | — | — | | 0.4 | 0.8 | — | | 99.52 99.12 |
| Ex. 5.21 (% w/w) | — | — | | — | | 0.4 | 1.6 | 99.52 98.32 |
| Ex. 5.25 (% w/w) | — | — | | — | | — | | 99.0 96.8 |
| Ex. 5.26 (% w/w) | 0.8 | — | | — | | — | | 98.6 98.0 |
| Ex. 5.27 (% w/w) | — | 0.8 | 1.6 | — | | — | | 98.6 97.2 |
| Ex. 5.28 (% w/w) | — | — | | 0.4 | 0.8 | — | | 99.0 98.0 |
| Ex. 5.29 (% w/w) | — | — | | — | | 0.4 | 1.6 | 99.0 97.2 |
| Ex. 5.33 (% w/w) | — | — | | — | | — | | 96.6 92 |
| Ex. 5.34 (% w/w) | 0.8 | — | | — | | — | | 96.2 93.2 |
| Ex. 5.35 (% w/w) | — | 0.8 | 1.6 | — | | — | | 96.2 92.4 |
| Ex. 5.36 (% w/w) | — | — | | 0.4 | 0.8 | — | | 96.6 93.2 |
| Ex. 5.37 (% w/w) | — | — | | — | | 0.4 | 1.6 | 96.6 92.4 |
| Ex. 5.41 (% w/w) | — | — | | — | | — | | 98.8 97.2 |
| Ex. 5.42 (% w/w) | 0.8 | — | | — | | — | | 98.4 |
| Ex. 5.43 (% w/w) | — | 0.8 | 1.6 | — | | — | | 98.4 97.6 |
| Ex. 5.44 (% w/w) | — | — | | 0.4 | 0.8 | — | | 98.8 98.4 |
| Ex. 5.45 (% w/w) | — | — | | — | | 0.4 | 1.6 | 98.2 97.6 |

TABLE 7.2-continued

| | | | | | | | |
|---|---|---|---|---|---|---|---|
| Ex. 5.49 (% w/w) | — | — | — | — | — | 99.58 | 97.96 |
| Ex. 5.50 (% w/w) | 0.8 | — | — | — | — | 99.18 | 99.16 |
| Ex. 5.51 (% w/w) | — | 0.8 | 1.6 | — | — | 99.18 | 98.36 |
| Ex. 5.52 (% w/w) | — | — | 0.4 | 0.8 | — | 99.58 | 99.16 |
| Ex. 5.53 (% w/w) | — | — | — | 0.4 | 1.6 | 99.58 | 98.36 |

Örnek—G

| Content | % Weight (w/w) |
|---|---|
| Muscarinic receptor antagonist | |
| Corticosteroid | |
| Lactose | |
| Mannitol | |

1—

| | Weight and percentage amount | | | |
|---|---|---|---|---|
| Content | 25 mg | % | 5 mg | % |
| Tiotropium | 0.018 | 0.072 | 0.018 | 0.36 |
| Budesonid | 0.2 | 0.8 | 0.2 | 4 |
| Lactose | 1.2391 | 4.9564 | 0.2391 | 4.782 |
| Mannitol | 23.5429 | 94.1716 | 4.5429 | 90.858 |
| TOTAL | 25 | | 5 | |

2—

| | Weight and percentage amount | | | |
|---|---|---|---|---|
| Content | 25 mg | % | 5 mg | % |
| Tiotropium | 0.018 | 0.072 | 0.018 | 0.36 |
| Budesonid | 0.2 | 0.8 | 0.2 | 4 |
| Mannitol | 1.2391 | 4.9564 | 0.2391 | 4.782 |
| Lactose | 23.5429 | 94.1716 | 4.5429 | 90.858 |
| TOTAL | 25 | | 5 | |

3—

| | Weight and percentage amount | | | |
|---|---|---|---|---|
| Content | 25 mg | % | 5 mg | % |
| Tiotropium | 0.018 | 0.072 | 0.018 | 0.36 |
| Budesonid | 0.4 | 1.6 | 0.4 | 8 |
| Lactose | 1.2291 | 4.9164 | 0.2291 | 4.582 |
| Mannitol | 23.3529 | 93.4116 | 4.3529 | 87.058 |
| TOTAL | 25 | | 5 | |

4—

| | Weight and percentage amount | | | |
|---|---|---|---|---|
| Content | 25 mg | % | 5 mg | % |
| Tiotropium | 0.018 | 0.072 | 0.018 | 0.36 |
| Budesonid | 0.4 | 1.6 | 0.4 | 8 |
| Mannitol | 1.2291 | 4.9164 | 0.2291 | 4.582 |
| Lactose | 23.3529 | 93.4116 | 4.3529 | 87.058 |
| TOTAL | 25 | | 5 | |

5—

| | Weight and percentage amount | | | |
|---|---|---|---|---|
| Content | 25 mg | % | 5 mg | % |
| Tiotropium | 0.018 | 0.072 | 0.018 | 0.36 |
| Fluticasone | 0.1 | 0.4 | 0.1 | 2 |
| Lactose | 1.2441 | 4.9764 | 0.2441 | 4.882 |
| Mannitol | 23.6379 | 94.5516 | 4.6379 | 92.758 |
| TOTAL | 25 | | 5 | |

6—

| | Weight and percentage amount | | | |
|---|---|---|---|---|
| Content | 25 mg | % | 5 mg | % |
| Tiotropium | 0.018 | 0.072 | 0.018 | 0.36 |
| Fluticasone | 0.1 | 0.4 | 0.1 | 2 |
| Mannitol | 1.2441 | 4.9764 | 0.2441 | 4.882 |
| Lactose | 23.6379 | 64.5516 | 4.6379 | 92.758 |
| TOTAL | 25 | | 5 | |

7—

| | Weight and percentage amount | | | |
|---|---|---|---|---|
| Content | 25 mg | % | 5 mg | % |
| Tiotropium | 0.018 | 0.072 | 0.018 | 0.36 |
| Fluticasone | 0.25 | 1 | 0.25 | 5 |
| Lactose | 1.2366 | 4.9464 | 0.2366 | 4.732 |
| Mannitol | 23.4954 | 93.9816 | 4.4954 | 89.908 |
| TOTAL | 25 | | 5 | |

8—

| | Weight and percentage amount | | | |
|---|---|---|---|---|
| Content | 25 mg | % | 5 mg | % |
| Tiotropium | 0.018 | 0.072 | 0.018 | 0.36 |
| Fluticasone | 0.25 | 1 | 0.25 | 5 |

47

-continued

| Content | Weight and percentage amount | | | |
|---|---|---|---|---|
| | 25 mg | % | 5 mg | % |
| Mannitol | 1.2366 | 4.9464 | 0.2366 | 4.732 |
| Lactose | 23.4954 | 93.9816 | 4.4954 | 89.908 |
| TOTAL | 25 | | 5 | |

9—

| Content | Weight and percentage amount | | | |
|---|---|---|---|---|
| | 25 mg | % | 5 mg | % |
| Tiotropium | 0.018 | 0.072 | 0.018 | 0.36 |
| Fluticasone | 0.05 | 0.2 | 0.05 | 1 |
| Lactose | 1.2466 | 4.9864 | 0.2466 | 4.932 |
| Mannitol | 23.6854 | 94.7416 | 4.6854 | 93.708 |
| TOTAL | 25 | | 5 | |

10—

| Content | Weight and percentage amount | | | |
|---|---|---|---|---|
| | 25 mg | % | 5 mg | % |
| Tiotropium | 0.018 | 0.072 | 0.018 | 0.36 |
| Fluticasone | 0.05 | 0.2 | 0.05 | 1 |
| Mannitol | 1.2466 | 4.9864 | 0.2466 | 4.932 |
| Lactose | 23.6854 | 94.7416 | 4.6854 | 93.708 |
| TOTAL | 25 | | 5 | |

Examples—F

| Content | % Weight (w/w) |
|---|---|
| Corticosteroid | |
| β2-adrenerjik agonist | |
| Muscarinic receptor antagonist | |
| Lactose | |
| Mannitol | |
| eksipiyan | |

1—

| Content | Weight and percentage amount | | | |
|---|---|---|---|---|
| | mg | % | mg | % |
| Budesonid | 0.2 | 0.8 | 0.2 | 4 |
| Formoterol | 0.012 | 0.048 | 0.012 | 0.24 |
| Tiotropium | 0.018 | 0.072 | 0.018 | 0.36 |
| Lactose | 1.2385 | 4.954 | 0.2385 | 4.77 |
| Mannitol | 23.5315 | 94.126 | 4.5315 | 90.63 |
| TOTAL | 25 | 100 | 5 | 100 |

48

2—

| Content | Weight and percentage amount | | | |
|---|---|---|---|---|
| | mg | % | mg | % |
| Budesonid | 0.2 | 0.8 | 0.2 | 4 |
| Formoterol | 0.012 | 0.048 | 0.012 | 0.24 |
| Tiotropium | 0.018 | 0.072 | 0.018 | 0.36 |
| Mannitol | 1.2385 | 4.954 | 0.2385 | 4.77 |
| Lactose | 23.5315 | 94.126 | 4.5315 | 90.63 |
| TOTAL | 25 | | 5 | |

3—

| Content | Weight and percentage amount | | | |
|---|---|---|---|---|
| | mg | % | mg | % |
| Budesonid | 0.4 | 1.6 | 0.4 | 8 |
| Formoterol | 0.012 | 0.048 | 0.012 | 0.24 |
| Tiotropium | 0.018 | 0.072 | 0.018 | 0.36 |
| Lactose | 1.2285 | 4.914 | 0.2285 | 4.57 |
| Mannitol | 23.3415 | 93.366 | 4.3415 | 86.83 |
| TOTAL | 25 | 100 | 5 | 100 |

4—

| Content | Weight and percentage amount | | | |
|---|---|---|---|---|
| | mg | % | mg | % |
| Budesonid | 0.4 | 1.6 | 0.4 | 8 |
| Formoterol | 0.012 | 0.048 | 0.012 | 0.24 |
| Tiotropium | 0.018 | 0.072 | 0.018 | 0.36 |
| Mannitol | 1.2285 | 4.914 | 0.2285 | 4.57 |
| Lactose | 23.3415 | 93.366 | 4.3415 | 86.83 |
| TOTAL | 25 | | 5 | |

5—

| Content | Weight and percentage amount | | | |
|---|---|---|---|---|
| | mg | % | mg | % |
| Ciclesonide | 0.2 | 0.8 | 0.2 | 4 |
| Formoterol | 0.006 | 0.024 | 0.006 | 0.12 |
| Tiotropium | 0.009 | 0.036 | 0.009 | 0.18 |
| Lactose | 1.23925 | 4.957 | 0.23925 | 4.785 |
| Mannitol | 23.54575 | 94.183 | 4.54575 | 90.915 |
| TOTAL | 25 | | 5 | |

6—

| Content | Weight and percentage amount | | | |
|---|---|---|---|---|
| | mg | % | mg | % |
| Ciclesonide | 0.2 | 0.8 | 0.2 | 4 |
| Formoterol | 0.006 | 0.024 | 0.006 | 0.12 |
| Tiotropium | 0.018 | 0.072 | 0.018 | 0.36 |
| Mannitol | 1.2388 | 4.9552 | 0.2388 | 4.776 |
| Lactose | 23.5372 | 94.1488 | 4.5372 | 90.744 |
| TOTAL | 25 | | 5 | |

7—

| Content | Weight and percentage amount | | | |
|---|---|---|---|---|
| | mg | % | mg | % |
| Fluticasone | 0.1 | 0.4 | 0.1 | 2 |
| salmeterol | 0.05 | 0.2 | 0.05 | 1 |
| Tiotropium | 0.018 | 0.072 | 0.018 | 0.36 |
| Lactose | 1.2416 | 4.9664 | 0.2416 | 4.832 |
| Mannitol | 23.5904 | 94.3616 | 4.5904 | 91.808 |
| TOTAL | 25 | | 5 | |

8—

| Content | Weight and percentage amount | | | |
|---|---|---|---|---|
| | mg | % | mg | % |
| Fluticasone | 0.1 | 0.4 | 0.1 | 2 |
| salmeterol | 0.05 | 0.2 | 0.05 | 1 |
| Tiotropium | 0.018 | 0.072 | 0.018 | 0.36 |
| Mannitol | 1.2416 | 4.9664 | 0.2416 | 4.832 |
| Lactose | 23.5904 | 94.3616 | 4.5904 | 91.808 |
| TOTAL | 25 | | 5 | |

9—

| Content | Weight and percentage amount | | | |
|---|---|---|---|---|
| | mg | % | mg | % |
| Fluticasone | 0.25 | 1 | 0.25 | 5 |
| salmeterol | 0.05 | 0.2 | 0.05 | 1 |
| Tiotropium | 0.018 | 0.072 | 0.018 | 0.36 |
| Lactose | 1.2341 | 4.9364 | 0.2341 | 4.682 |
| Mannitol | 23.4479 | 93.7916 | 4.4479 | 8.958 |
| TOTAL | 25 | | 5 | |

10—

| Content | Weight and percentage amount | | | |
|---|---|---|---|---|
| | mg | % | mg | % |
| Fluticasone | 0.25 | 1 | 0.25 | 5 |
| salmeterol | 0.05 | 0.2 | 0.05 | 1 |
| Tiotropium | 0.018 | 0.072 | 0.018 | 0.36 |
| Mannitol | 1.2341 | 4.9364 | 0.2341 | 4.682 |
| Lactose | 23.4479 | 93.7916 | 4.4479 | 88.958 |
| TOTAL | 25 | | 5 | |

11—

| Content | Weight and percentage amount | | | |
|---|---|---|---|---|
| | mg | % | mg | % |
| Fluticasone | 0.05 | 0.2 | 0.05 | 1 |
| salmeterol | 0.05 | 0.2 | 0.05 | 1 |

-continued

| Content | Weight and percentage amount | | | |
|---|---|---|---|---|
| | mg | % | mg | % |
| Tiotropium | 0.018 | 0.072 | 0.018 | 0.36 |
| Lactose | 1.2441 | 4.9764 | 0.2441 | 4.882 |
| Mannitol | 23.6379 | 94.5516 | 4.6379 | 92.758 |
| TOTAL | 25 | | 5 | |

12—

| Content | Weight and percentage amount | | | |
|---|---|---|---|---|
| | mg | % | mg | % |
| Fluticasone | 0.05 | 0.2 | 0.05 | 1 |
| salmeterol | 0.05 | 0.2 | 0.05 | 1 |
| Tiotropium | 0.018 | 0.072 | 0.018 | 0.36 |
| Mannitol | 1.2441 | 4.9764 | 0.2441 | 4.882 |
| Lactose | 23.6379 | 94.5516 | 4.6379 | 92.758 |
| TOTAL | 25 | | 5 | |

13—

| Content | Weight and percentage amount | | | |
|---|---|---|---|---|
| | mg | % | mg | % |
| Fluticasone | 0.1 | 0.4 | 0.1 | 2 |
| Arformeterol | 0.015 | 0.06 | 0.015 | 0.3 |
| Tiotropium | 0.018 | 0.072 | 0.018 | 0.36 |
| Lactose | 1.24335 | 4.9734 | 0.24335 | 4.867 |
| Mannitol | 23.62365 | 94.4946 | 4.62365 | 92.473 |
| TOTAL | 25 | | 5 | |

14—

| Content | Weight and percentage amount | | | |
|---|---|---|---|---|
| | mg | % | mg | % |
| Fluticasone | 0.1 | 0.4 | 0.1 | 2 |
| Arformeterol | 0.015 | 0.06 | 0.015 | 0.3 |
| Tiotropium | 0.018 | 0.072 | 0.018 | 0.36 |
| Mannitol | 1.24335 | 4.9734 | 0.24335 | 4.867 |
| Lactose | 23.62365 | 94.4946 | 4.62365 | 92.473 |
| TOTAL | 25 | | 5 | |

15—

| Content | Weight and percentage amount | | | |
|---|---|---|---|---|
| | mg | % | mg | % |
| Fluticasone | 0.25 | 1 | 0.25 | 5 |
| Arformeterol | 0.015 | 0.06 | 0.015 | 0.3 |
| Tiotropium | 0.018 | 0.072 | 0.018 | 0.36 |

-continued

|  | Weight and percentage amount | | | |
|---|---|---|---|---|
| Content | mg | % | mg | % |
| Lactose | 1.23585 | 4.9434 | 0.23585 | 4.717 |
| Mannitol | 23.48115 | 93.9246 | 4.48115 | 89.623 |
| TOTAL | 25 | | 5 | |

16—

|  | Weight and percentage amount | | | |
|---|---|---|---|---|
| Content | mg | % | mg | % |
| Fluticasone | 0.25 | 1 | 0.25 | 5 |
| Arformeterol | 0.015 | 0.06 | 0.015 | 0.3 |
| Tiotropium | 0.018 | 0.072 | 0.018 | 0.36 |
| Mannitol | 1.23585 | 4.9434 | 0.23585 | 4.717 |
| Lactose | 23.48115 | 93.9246 | 4.48115 | 89.623 |
| TOTAL | 25 | | 5 | |

17—

|  | Weight and percentage amount | | | |
|---|---|---|---|---|
| Content | mg | % | mg | % |
| Fluticasone | 0.05 | 0.2 | 0.05 | 1 |
| Arformeterol | 0.015 | 0.06 | 0.015 | 0.3 |
| Tiotropium | 0.018 | 0.072 | 0.018 | 0.36 |
| Lactose | 1.24585 | 4.9834 | 0.24585 | 4.917 |
| Mannitol | 23.67115 | 94.6846 | 4.67115 | 93.423 |
| TOTAL | 25 | | 5 | |

18—

|  | Weight and percentage amount | | | |
|---|---|---|---|---|
| Content | mg | % | mg | % |
| Fluticasone | 0.05 | 0.2 | 0.05 | 1 |
| Arformeterol | 0.015 | 0.06 | 0.015 | 0.3 |
| Tiotropium | 0.018 | 0.072 | 0.018 | 0.36 |
| Mannitol | 1.24585 | 4.9834 | 0.24585 | 4.917 |
| Lactose | 23.67115 | 94.6846 | 4.67115 | 93.423 |
| TOTAL | 25 | | 5 | |

19—

|  | Weight and percentage amount | | | |
|---|---|---|---|---|
| Content | mg | % | mg | % |
| Fluticasone | 0.1 | 0.4 | 0.1 | 2 |
| Indacaterol | 0.15 | 0.6 | 0.15 | 3 |
| Tiotropium | 0.018 | 0.072 | 0.018 | 0.36 |
| Lactose | 1.2366 | 4.9464 | 0.2366 | 4.732 |
| Mannitol | 23.4954 | 93.9816 | 4.4954 | 89.908 |
| TOTAL | 25 | | 5 | |

20—

|  | Weight and percentage amount | | | |
|---|---|---|---|---|
| Content | mg | % | mg | % |
| Fluticasone | 0.1 | 0.4 | 0.1 | 2 |
| Indacaterol | 0.15 | 0.6 | 0.15 | 3 |
| Tiotropium | 0.018 | 0.072 | 0.018 | 0.36 |
| Mannitol | 1.2366 | 4.9464 | 0.2366 | 4.732 |
| Lactose | 23.4954 | 93.9816 | 4.4954 | 89.908 |
| TOTAL | 25 | | 5 | |

21—

|  | Weight and percentage amount | | | |
|---|---|---|---|---|
| Content | mg | % | mg | % |
| Fluticasone | 0.25 | 1 | 0.25 | 5 |
| Indacaterol | 0.15 | 0.6 | 0.15 | 3 |
| Tiotropium | 0.018 | 0.072 | 0.018 | 0.36 |
| Lactose | 1.2291 | 4.9164 | 0.2291 | 4.582 |
| Mannitol | 23.3529 | 93.4116 | 4.3529 | 87.058 |
| TOTAL | 25 | | 5 | |

22—

|  | Weight and percentage amount | | | |
|---|---|---|---|---|
| Content | mg | % | mg | % |
| Fluticasone | 0.25 | 1 | 0.25 | 5 |
| Indacaterol | 0.15 | 0.6 | 0.15 | 3 |
| Tiotropium | 0.018 | 0.072 | 0.018 | 0.36 |
| Mannitol | 1.2291 | 4.9164 | 0.2291 | 4.582 |
| Lactose | 23.3529 | 93.4116 | 4.3529 | 87.058 |
| TOTAL | 25 | | 5 | |

23—

|  | Weight and percentage amount | | | |
|---|---|---|---|---|
| Content | mg | % | mg | % |
| Fluticasone | 0.05 | 0.2 | 0.05 | 1 |
| Indacaterol | 0.15 | 0.6 | 0.15 | 3 |
| Tiotropium | 0.018 | 0.072 | 0.018 | 0.36 |
| Lactose | 1.2391 | 4.9564 | 0.2391 | 4.782 |
| Mannitol | 23.5429 | 94.1716 | 4.5429 | 90.858 |
| TOTAL | 25 | | 5 | |

24—

|  | Weight and percentage amount | | | |
|---|---|---|---|---|
| Content | mg | % | mg | % |
| Fluticasone | 0.05 | 0.2 | 0.05 | 1 |
| Indacaterol | 0.15 | 0.6 | 0.15 | 3 |

|  | Weight and percentage amount | | | |
|---|---|---|---|---|
| Content | mg | % | mg | % |
| Tiotropium | 0.018 | 0.072 | 0.018 | 0.36 |
| Mannitol | 1.2391 | 4.9564 | 0.2391 | 4.782 |
| Lactose | 23.5429 | 94.1716 | 4.5429 | 90.858 |
| TOTAL | 25 | | 5 | |

25—

|  | Weight and percentage amount | | | |
|---|---|---|---|---|
| Content | mg | % | mg | % |
| Budesonid | 0.2 | 0.8 | 0.2 | 4 |
| Indacaterol | 0.15 | 0.6 | 0.15 | 3 |
| Tiotropium | 0.018 | 0.072 | 0.018 | 0.36 |
| Lactose | 1.2316 | 4.9264 | 0.2316 | 4.632 |
| Mannitol | 23.4004 | 93.6016 | 4.4004 | 88.008 |
| TOTAL | 25 | | 5 | |

26—

|  | Weight and percentage amount | | | |
|---|---|---|---|---|
| Content | mg | % | mg | % |
| Budesonid | 0.2 | 0.8 | 0.2 | 4 |
| Indacaterol | 0.15 | 0.6 | 0.15 | 3 |
| Tiotropium | 0.018 | 0.072 | 0.018 | 0.36 |
| Mannitol | 1.2316 | 4.9264 | 0.2316 | 4.632 |
| Lactose | 23.4004 | 93.6016 | 4.4004 | 88.008 |
| TOTAL | 25 | | 5 | |

27—

|  | Weight and percentage amount | | | |
|---|---|---|---|---|
| Content | mg | % | mg | % |
| Budesonid | 0.4 | 1.6 | 0.4 | 8 |
| Indacaterol | 0.15 | 0.6 | 0.15 | 3 |
| Tiotropium | 0.018 | 0.072 | 0.018 | 0.36 |
| Lactose | 1.2216 | 4.8864 | 0.2216 | 4.432 |
| Mannitol | 23.2104 | 92.8416 | 4.2104 | 84.208 |
| TOTAL | 25 | | 5 | |

28—

|  | Weight and percentage amount | | | |
|---|---|---|---|---|
| Content | mg | % | mg | % |
| Budesonid | 0.4 | 1.6 | 0.4 | 8 |
| Indacaterol | 0.15 | 0.6 | 0.15 | 3 |
| Tiotropium | 0.018 | 0.072 | 0.018 | 0.36 |
| Mannitol | 1.2216 | 4.8864 | 0.2216 | 4.432 |
| Lactose | 23.2104 | 92.8416 | 4.2104 | 84.208 |
| TOTAL | 25 | | 5 | |

29—

|  | Weight and percentage amount | | | |
|---|---|---|---|---|
| Content | mg | % | mg | % |
| Budesonid | 0.2 | 0.8 | 0.2 | 4 |
| Olodeterol | 0.005 | 0.02 | 0.005 | 0.1 |
| Tiotropium | 0.018 | 0.072 | 0.018 | 0.36 |
| Lactose | 1.23885 | 4.9554 | 0.23885 | 4.777 |
| Mannitol | 23.53815 | 94.1526 | 4.53815 | 90.763 |
| TOTAL | 25 | | 5 | |

30—

|  | Weight and percentage amount | | | |
|---|---|---|---|---|
| Content | mg | % | mg | % |
| Budesonid | 0.2 | 0.8 | 0.2 | 4 |
| Olodeterol | 0.005 | 0.02 | 0.005 | 0.1 |
| Tiotropium | 0.018 | 0.072 | 0.018 | 0.36 |
| Mannitol | 1.23885 | 4.9554 | 0.23885 | 4.777 |
| Lactose | 23.53815 | 94.1526 | 4.53815 | 90.763 |
| TOTAL | 25 | | 5 | |

31—

|  | Weight and percentage amount | | | |
|---|---|---|---|---|
| Content | mg | % | mg | % |
| Budesonid | 0.4 | 1.6 | 0.4 | 8 |
| Olodeterol | 0.005 | 0.02 | 0.005 | 0.1 |
| Tiotropium | 0.018 | 0.072 | 0.018 | 0.36 |
| Lactose | 1.22885 | 4.9154 | 0.22885 | 4.577 |
| Mannitol | 23.34815 | 93.3926 | 4.34815 | 86.963 |
| TOTAL | 25 | | 5 | |

32—

|  | Weight and percentage amount | | | |
|---|---|---|---|---|
| Content | mg | % | mg | % |
| Budesonid | 0.4 | 1.6 | 0.4 | 8 |
| Olodeterol | 0.005 | 0.02 | 0.005 | 0.1 |
| Tiotropium | 0.018 | 0.072 | 0.018 | 0.36 |

-continued

| Content | Weight and percentage amount | | | |
|---|---|---|---|---|
| | mg | % | mg | % |
| Mannitol | 1.22885 | 4.9154 | 0.22885 | 4.577 |
| Lactose | 23.34815 | 93.3926 | 4.34815 | 86.963 |
| TOTAL | 25 | | 5 | |

33—

| Content | Weight and percentage amount | | | |
|---|---|---|---|---|
| | mg | % | mg | % |
| Budesonid | 0.2 | 0.8 | 0.2 | 4 |
| Vilanterol | 0.025 | 0.1 | 0.025 | 0.5 |
| Tiotropium | 0.018 | 0.072 | 0.018 | 0.36 |
| Lactose | 1.23785 | 4.9514 | 0.23785 | 4.757 |
| Mannitol | 23.51915 | 94.0766 | 4.51915 | 90.383 |
| TOTAL | 25 | | 5 | |

34—

| Content | Weight and percentage amount | | | |
|---|---|---|---|---|
| | mg | % | mg | % |
| Budesonid | 0.2 | 0.8 | 0.2 | 4 |
| Vilanterol | 0.025 | 0.1 | 0.025 | 0.5 |
| Tiotropium | 0.018 | 0.072 | 0.018 | 0.36 |
| Mannitol | 1.23785 | 4.9514 | 0.23785 | 4.757 |
| Lactose | 23.51915 | 94.0766 | 4.51915 | 90.383 |
| TOTAL | 25 | | 5 | |

35—

| Content | Weight and percentage amount | | | |
|---|---|---|---|---|
| | mg | % | mg | % |
| Budesonid | 0.4 | 1.6 | 0.4 | 8 |
| Vilanterol | 0.025 | 0.1 | 0.025 | 0.5 |
| Tiotropium | 0.018 | 0.072 | 0.018 | 0.36 |
| Lactose | 1.22785 | 4.9114 | 0.22785 | 4.557 |
| Mannitol | 23.32915 | 93.3166 | 4.32915 | 86.583 |
| TOTAL | 25 | | 5 | |

36—

| Content | Weight and percentage amount | | | |
|---|---|---|---|---|
| | mg | % | mg | % |
| Budesonid | 0.4 | 1.6 | 0.4 | 8 |
| Vilanterol | 0.025 | 0.1 | 0.025 | 0.5 |
| Tiotropium | 0.018 | 0.072 | 0.018 | 0.36 |
| Lactose | 1.22785 | 4.9114 | 0.22785 | 4.557 |
| Mannitol | 23.32915 | 93.3166 | 4.32915 | 86.583 |
| TOTAL | 25 | | 5 | |

37—

| Content | Weight and percentage amount | | | |
|---|---|---|---|---|
| | mg | % | mg | % |
| Mometazon | 0.1 | 0.4 | 0.1 | 2 |
| Indacaterol | 0.15 | 0.6 | 0.15 | 3 |
| Glikoporonyum | 0.1 | 0.4 | 0.1 | 2 |
| Lactose | 1.2325 | 4.93 | 0.2325 | 4.65 |
| Mannitol | 23.4175 | 93.67 | 4.4175 | 88.35 |
| TOTAL | 25 | | 5 | |

38—

| Content | Weight and percentage amount | | | |
|---|---|---|---|---|
| | mg | % | mg | % |
| Mometazon | 0.1 | 0.4 | 0.1 | 2 |
| Indacaterol | 0.15 | 0.6 | 0.15 | 3 |
| Glikoporonyum | 0.1 | 0.4 | 0.1 | 2 |
| Mannitol | 1.2325 | 4.93 | 0.2325 | 4.65 |
| Lactose | 23.4175 | 93.67 | 4.4175 | 88.35 |
| TOTAL | 25 | | 5 | |

39—

| Content | Weight and percentage amount | | | |
|---|---|---|---|---|
| | mg | % | mg | % |
| Mometazon | 0.2 | 0.8 | 0.2 | 4 |
| Indacaterol | 0.15 | 0.6 | 0.15 | 3 |
| Glikoporonyum | 0.1 | 0.4 | 0.1 | 2 |
| Lactose | 1.2275 | 4.91 | 0.2275 | 4.55 |
| Mannitol | 23.3225 | 93.29 | 4.3225 | 86.45 |
| TOTAL | 25 | | 5 | |

40—

| Content | Weight and percentage amount | | | |
|---|---|---|---|---|
| | mg | % | mg | % |
| Mometazon | 0.2 | 0.8 | 0.2 | 4 |
| Indacaterol | 0.15 | 0.6 | 0.15 | 3 |
| Glikoporonyum | 0.1 | 0.4 | 0.1 | 2 |

-continued

|         | Weight and percentage amount | | | |
|---------|------|-------|--------|-------|
| Content | mg   | %     | mg     | %     |
| Mannitol | 1.2275 | 4.91 | 0.2275 | 4.55 |
| Lactose  | 23.3225 | 93.29 | 4.3225 | 86.45 |
| TOTAL   | 25   |       | 5      |       |

41—

|         | Weight and percentage amount | | | |
|---------|------|-------|--------|-------|
| Content | mg   | %     | mg     | %     |
| Fluticasone | 0.1 | 0.4 | 0.1 | 2 |
| Salmeterol  | 0.05 | 0.2 | 0.05 | 1 |
| Salbutamol  | 0.1 | 0.4 | 0.1 | 2 |
| Lactose     | 1.2375 | 4.95 | 0.2375 | 4.75 |
| Mannitol    | 23.5125 | 94.05 | 4.5125 | 90.25 |
| TOTAL       | 25 | | 5 | |

42—

|         | Weight and percentage amount | | | |
|---------|------|-------|--------|-------|
| Content | mg   | %     | mg     | %     |
| Fluticasone | 0.1 | 0.4 | 0.1 | 2 |
| Salmeterol  | 0.05 | 0.2 | 0.05 | 1 |
| Salbutamol  | 0.1 | 0.4 | 0.1 | 2 |
| Mannitol    | 1.2375 | 4.95 | 0.2375 | 4.75 |
| Lactose     | 23.5125 | 94.05 | 4.5125 | 90.25 |
| TOTAL       | 25 | | 5 | |

43—

|         | Weight and percentage amount | | | |
|---------|------|-------|--------|-------|
| Content | mg   | %     | mg     | %     |
| Fluticasone | 0.25 | 1 | 0.25 | 5 |
| Salmeterol  | 0.05 | 0.2 | 0.05 | 1 |
| Salbutamol  | 0.1 | 0.4 | 0.1 | 2 |
| Lactose     | 1.23 | 4.92 | 0.23 | 4.6 |
| Mannitol    | 23.37 | 93.48 | 4.37 | 87.4 |
| TOTAL       | 25 | | 5 | |

44—

|         | Weight and percentage amount | | | |
|---------|------|-------|--------|-------|
| Content | mg   | %     | mg     | %     |
| Fluticasone | 0.25 | 1 | 0.25 | 5 |
| Salmeterol  | 0.05 | 0.2 | 0.05 | 1 |
| Salbutamol  | 0.1 | 0.4 | 0.1 | 2 |

-continued

|         | Weight and percentage amount | | | |
|---------|------|-------|--------|-------|
| Content | mg   | %     | mg     | %     |
| Mannitol | 1.23 | 4.92 | 0.23 | 4.6 |
| Lactose  | 23.37 | 93.48 | 4.37 | 87.4 |
| TOTAL   | 25   |       | 5      |       |

45—

|         | Weight and percentage amount | | | |
|---------|------|-------|--------|-------|
| Content | mg   | %     | mg     | %     |
| Fluticasone | 0.5 | 2 | 0.5 | 10 |
| Salmeterol  | 0.05 | 0.2 | 0.05 | 1 |
| Salbutamol  | 0.1 | 0.4 | 0.1 | 2 |
| Lactose     | 1.2175 | 4.87 | 0.2175 | 4.35 |
| Mannitol    | 23.1325 | 92.53 | 4.1325 | 82.65 |
| TOTAL       | 25 | | 5 | |

46—

|         | Weight and percentage amount | | | |
|---------|------|-------|--------|-------|
| Content | mg   | %     | mg     | %     |
| Fluticasone | 0.5 | 2 | 0.5 | 10 |
| Salmeterol  | 0.05 | 0.2 | 0.05 | 1 |
| Salbutamol  | 0.1 | 0.4 | 0.1 | 2 |
| Mannitol    | 1.2175 | 4.87 | 0.2175 | 4.35 |
| Lactose     | 23.1325 | 92.53 | 4.1325 | 82.65 |
| TOTAL       | 25 | | 5 | |

47—

|         | Weight and percentage amount | | | |
|---------|------|-------|--------|-------|
| Content | mg   | %     | mg     | %     |
| Fluticasone | 0.1 | 0.4 | 0.1 | 2 |
| Arformeterol | 0.015 | 0.06 | 0.015 | 0.3 |
| Salbutamol  | 0.1 | 0.4 | 0.1 | 2 |
| Lactose     | 1.23925 | 4.957 | 0.23925 | 4.785 |
| Mannitol    | 23.54575 | 94.183 | 4.54575 | 90.915 |
| TOTAL       | 25 | | 5 | |

48—

|         | Weight and percentage amount | | | |
|---------|------|-------|--------|-------|
| Content | mg   | %     | mg     | %     |
| Fluticasone | 0.1 | 0.4 | 0.1 | 2 |
| Arformeterol | 0.015 | 0.06 | 0.015 | 0.3 |
| Salbutamol  | 0.1 | 0.4 | 0.1 | 2 |

-continued

|  | Weight and percentage amount | | | |
|---|---|---|---|---|
| Content | mg | % | mg | % |
| Mannitol | 1.23925 | 4.957 | 0.23925 | 4.785 |
| Lactose | 23.54575 | 94.183 | 4.54575 | 90.915 |
| TOTAL | 25 | | 5 | |

49—

|  | Weight and percentage amount | | | |
|---|---|---|---|---|
| Content | mg | % | mg | % |
| Fluticasone | 0.25 | 1 | 0.25 | 5 |
| Arformeterol | 0.015 | 0.06 | 0.015 | 0.3 |
| Salbutamol | 0.1 | 0.4 | 0.1 | 2 |
| Lactose | 1.23175 | 4.927 | 0.23175 | 4.635 |
| Mannitol | 23.40325 | 93.613 | 4.40325 | 88.065 |
| TOTAL | 25 | | 5 | |

50—

|  | Weight and percentage amount | | | |
|---|---|---|---|---|
| Content | mg | % | mg | % |
| Fluticasone | 0.25 | 1 | 0.25 | 5 |
| Arformeterol | 0.015 | 0.06 | 0.015 | 0.3 |
| Salbutamol | 0.1 | 0.4 | 0.1 | 2 |
| Mannitol | 1.23175 | 4.927 | 0.23175 | 4.635 |
| Lactose | 23.40325 | 93.613 | 4.40325 | 88.065 |
| TOTAL | 25 | | 5 | |

51—

|  | Weight and percentage amount | | | |
|---|---|---|---|---|
| Content | mg | % | mg | % |
| Fluticasone | 0.5 | 2 | 0.5 | 10 |
| Arformeterol | 0.015 | 0.06 | 0.015 | 0.3 |
| Salbutamol | 0.1 | 0.4 | 0.1 | 2 |
| Lactose | 1.21925 | 4.877 | 0.21925 | 4.385 |
| Mannitol | 23.16575 | 92.663 | 4.16575 | 83.315 |
| TOTAL | 25 | | 5 | |

52—

|  | Weight and percentage amount | | | |
|---|---|---|---|---|
| Content | mg | % | mg | % |
| Fluticasone | 0.5 | 2 | 0.5 | 10 |
| Arformeterol | 0.015 | 0.06 | 0.015 | 0.3 |
| Salbutamol | 0.1 | 0.4 | 0.1 | 2 |
| Mannitol | 1.21925 | 4.877 | 0.21925 | 4.385 |
| Lactose | 23.16575 | 92.663 | 4.16575 | 83.315 |
| TOTAL | 25 | | 5 | |

Compositions according to the invention are manufactured by the processes of the state of art in such a way that they include mixtures of fine particle lactose-coarse particle mannitol, fine particle mannitol-coarse particle lactose and the active ingredients.

For Fine Particle Carriers (Lactose or Mannitol) Might be in the Range of:
d10; 1.0-5.0 μm or d10; 1.0-4.0 μm,
d50; 4.0-10.0 μm or d50; 4.0-7.0 μm,
d90; 7.0-20.0 μm or d90; 7.0-15.0 μm For Coarse Particle Carriers (Lactose or Mannitol) Might be in the Range of:
d10; 10.0-50.0 μm
d50; 50.0-120.0 μm or d50; 50.0-75.0 μm,
d90; 120.0-300.0 μm or d90; 75.0-250.0 μm.

Said compositions may be formed as:
i. Active ingredient+fine particle lactose+coarse particle mannitol,
ii. Active ingredient+fine particle lactose+coarse particle lactose,
iii. Active ingredient+fine particle lactose+fine particle mannitol+coarse particle mannitol,
iv. Active ingredient+fine particle lactose+fine particle mannitol+coarse particle lactose,
v. Active ingredient+fine particle lactose+coarse particle mannitol+coarse particle lactose,
vi. Active ingredient+fine particle lactose+fine particle mannitol+coarse particle mannitol+coarse particle lactose.

Surprisingly, said mannitol in the invention increases stability by absorbing moisture to it contained in the active ingredients inside the blister having air and moisture barriers or the airtight and moisture-tight capsule. Dehumidification of the active ingredient or ingredients bring the stability values to desired level. Furthermore, by means of ideal lactose and mannitol ratio and their determined particle sizes, compositions with content uniformity are developed. In addition to this, dosage accuracy present in each cavity or capsule is ensured as well. These preferred values facilitate the flowing and filling of the components as well, during the process. It is ensured that a homogeneous mixture is obtained and this filling is economical and fast.

Coarse carrier particles are used in or order to prevent agglomeration (anew) of the fine particles of the active ingredient. In order to obtain this effect, a carrier, the particle size of which is 10 times that of the active ingredient is used. In general, a single layer composed of the active ingredient particles is formed over the large carrier particles. During inhalation, as the active ingredient and the carrier substance need to be separated from each other, shape and surface roughness of the carrier particles are especially important. Particles of smooth surface will be separated much easier from the active ingredient compared to the particles in the same size but of high porosity.

Fine carrier particles are used so as to assist the active ingredient to reach to the lungs safer and in high doses. Active ingredient will tend to concentrate on the regions having higher energy as the surface energy normally does not dissipate on the carrier particle evenly. This might obstruct the active ingredient to separate from the carrier after pulmonary administration, especially in low dose formulations. As the high-energy regions will be covered by fine carrier particles and thus the active ingredient will tend to bind to low energy regions, usage of small fine carrier particles, size of which are less than 10.0 microns or 5.0 microns will help to prevent this situation. It has been discovered that by increasing the fraction of the fine carrier particles, taking into lungs will also increase. According to this, a decrease in the particle size (having finer particles) increases the fluidizing energy and this, in return, increases the amount of drug reached to the lungs.

Drug particles will adhere then to weak adhesion regions and will be released easier during inhalation. Surface area will significantly increase upon addition of fine particles and carrying capacity will decrease. The fact that the fine carrier particles are slightly coarser than the drug particles is sufficient to eliminate the frictional forces between the drug and the carrier during mixing process.

Another object of the invention is to adjust the fluidity of the formulations accurately in order to ensure that correct amounts of active ingredient are given to the DPIs by suitable devices. In other words, present invention provides freely-flowable formulations by choosing right carriers in order to ensure continuous production of formulations, mechanical filling of the powder inhaler, right dosage and release with powder inhaler.

Another object of the invention is to prevent agglomeration by using a suitable carrier except lactose. Active particles have fine or sometimes micro-fine particles in order to be able to penetrate deep into lungs. For this reason, these small drug particles tend to agglomerate.

In an ideal drug carrier system, binding of the active ingredient to the carrier should be as strong as to prevent decaying of the mixture yet it should be so strong as the active ingredient and the carrier need to separate during inhalation. Accordingly, shape of the carrier particles and surface roughness are of particular importance. Spray-dried mannitol particles are observed to detach from the active ingredient easier in comparison with the particles of high porosity in same size. Since, spray-dried mannitol forms more particles of spherical shape and a smooth surface. The characteristic of such particles is that they have a smaller contact area and a smaller and more homogeneous particle size distribution, which leads the inhalable particles to be more, compared to the carriers the diameters of which are diminished mechanically. An advantage of using spray-dried mannitol is to obtain particles in which the particle size distribution is narrow and the diameters are of a few micrometers. And this ensures the drug embedded in the trachea-bronchial and deep alveoli regions to be stored at maximum ratios by normal inhalation rate, once the suitable particle size is obtained. Furthermore, spray-dried mannitol exhibits narrow particle size, i.e., the ratio between the particle size (d50) and (d90) is equal to 0.40 or greater. The ratio between the d50 particle size and d90 is preferably between 0.45 and 0.50, more preferably between 0.50 and 0.70.

In addition to this, this narrow particle size distribution that is equal to 0.40 or greater applies also to mannitol contained in the compositions of present invention. Preferably, narrow particle size distribution is between 0.45 and 0.50, more preferably between 0.50 and 0.70.

Particle size analysis is performed by Malvern Mastersizer 2000 device with laser difraction technique. According to selected active ingredient may prefer particle characterization techniques that it can be wet dispersion (particles dispersed in a liquid) or dry dispersion (particles dispersed in a gas (usually air)). Particle size distribution measured volume-base.

According to a preferred embodiment of the invention, therapeutically active amount of said pharmaceutical compositions is administered once a day and/or twice a day.

According to a preferred embodiment, pharmaceutical compositions are used in the treatment of the respiratory diseases selected from asthma and chronic obstructive pulmonary disease and other obstructive respiratory diseases. Combinations of present invention are particularly useful in the treatment of the respiratory diseases or disorders including asthma, acute respiratory failure, chronic pulmonary inflammatory disease, bronchitis, chronic bronchitis, chronic obstructive pulmonary disease and silicosis or immune diseases and disorders including allergic rhinitis or chronic sinusitis.

According to another application, pharmaceutical compositions are suitable for separate, respective or simultaneous administration with a blister resistant to moisture and encapsulated with a secure barrier or with a capsule.

Blister especially contains aluminum in order to prevent moisture intake and thereby fine particle fraction (FPF) of the dose of the pharmaceutical composition is maintained. Blister is further encapsulated with a secure barrier resistant to moisture. By this means, blister prevents water penetration into the drug dose and moisture intake from outside into the container has been prevented.

In another preferred embodiment of the invention, dry powder is inside a capsule and this capsule may be a gelatin or a natural or synthetic pharmaceutically acceptable polymer such as hydroxypropyl methylcellulose.

Dosage amounts of 25 mg are stored inside air-tight and moisture-tight capsules, whereas dosage amounts of 5 mf are stored inside blisters.

Moreover, as said formulas may contain active ingredient in amounts of 3 or 5 mg alone or else in the amounts that are the multiples of 3 or 5 mg, it is also possible to manufacture combinations of said active ingredient comprising the amounts of 3 or 5 mg or else that are the multiples of 3 or 5 mg.

A pharmaceutically acceptable salt, solvate, polymorph or racemic mixture of said active ingredient may also be used.

Said ciclesonide may contain pharmaceutically acceptable salt, solvate, polymorph or racemic mixture thereof.

Said budesonide may contain pharmaceutically acceptable salt, solvate, polymorph or racemic mixture thereof.

As said fluticasone may contain pharmaceutically acceptable salt, solvate, polymorph or racemic mixture thereof, it is preferably propionate or fluticasone furoate.

As said mometasone may contain pharmaceutically acceptable salt, solvate, polymorph or racemic mixture thereof, it is preferably mometasone furoate or mometasone furoate anhydrate.

As said tiotropium may contain pharmaceutically acceptable salt, solvate, polymorph or racemic mixture thereof, it is preferably tiotropium bromide.

As said glycopyrronium may contain pharmaceutically acceptable salt, solvate, polymorph or racemic mixture thereof, it is preferably glycopyrronium bromide.

Said aclinidium may contain pharmaceutically acceptable salt, solvate, polymorph or racemic mixture thereof.

As said darotropium may contain pharmaceutically acceptable salt, solvate, polymorph or racemic mixture thereof, it is preferably darotropium bromide.

As said salmaterol may contain pharmaceutically acceptable salt, solvate, polymorph or racemic mixture thereof, it is preferably salmeterol xinafoate.

As said formoterol may contain pharmaceutically acceptable salt, solvate, polymorph or racemic mixture thereof, it is preferably formoterol fumarate.

As said arfomoterol may contain pharmaceutically acceptable salt, solvate, polymorph or racemic mixture thereof, it is preferably arfomoterol tartarate.

As said indacaterol may contain pharmaceutically acceptable salt, solvate, polymorph or racemic mixture thereof, it is preferably indaceterol maleate.

Said salbutamol may contain pharmaceutically acceptable salt, solvate, polymorph or racemic mixture thereof.

Said vilanterol may contain pharmaceutically acceptable salt, solvate, polymorph or racemic mixture thereof.

Said carmoterol may contain pharmaceutically acceptable salt, solvate, polymorph or racemic mixture thereof.

Said olodaterol may contain pharmaceutically acceptable salt, solvate, polymorph or racemic mixture thereof.

Said compositions are inserted in a dry powder inhaler device containing a blister and a cap.

Said device has at least one locking mechanism ensuring the device to be maintained locked in both of the positions in which it is ready for inhalation and its cap is closed and ensuring the device to be automatically re-set once the cap is closed.

Subsequent to opening of the device cap, a force is exerted to the device cock by the user. Afterwards, the cock is bolted by being guided by the tracks within the body of the device and the tracks on itself. Mechanism is assured to function via this action. In the end of bolting, cock is locked upon clamping and single dose drug come out of the blister is enabled to be administered. Pushing of the cock by the user completely until the locking position ensures the blister to be completely peeled off and the dosage amount to be accurately administered. As a result of this locking cock is immobilized and is disabled for a short time. This pushing action further causes the spring inside the mechanism to be compressed between the cock and the inner body of the device. Said device becomes ready to re-use following the closing of the cap by the user after the administration of the powder composition, without needing to be set again, thanks to the mechanism involved.

When said compositions are used in a dry powder inhaler comprising capsule, said capsule is put one by one in the device and used by means of exploding the capsule.

The invention claimed is:

1. A dry powder inhalation composition comprising,
   (a) at least one muscarinic receptor antagonist or a pharmaceutically acceptable salt thereof;
   (b) fine particle lactose in the amount of 1-20% by weight of said composition and having a (d50) particle size in the range of 4-10 µm; and
   (c) coarse particle mannitol in the amount of 80-99% by weight of said composition and having a (d50) particle size in the range of 50-120 µm and a (d90) particle size of 120-300 µm.

2. The pharmaceutical composition according to claim 1, wherein the (d50) particle size of said fine particle lactose is 4-7 µm, a (d10) particle size of said fine particle lactose is 1-5 µm, and/or a (d90) particle size of said fine particle lactose is 7-20 µm.

3. The pharmaceutical composition according to claim 1, further comprising coarse particle lactose with a (d50) particle size of 50-80 µm, coarse particle lactose with a (d10) particle size of 10-50 µm, and/or coarse particle lactose with a (d90) particle size of 120-300 µm.

4. The pharmaceutical composition according to claim 1, further comprising fine particle mannitol with a (d50) particle size of 4-7 µm; fine particle mannitol with a (d10) particle size of 1-5 µm; and/or fine particle mannitol with a (d90) particle size of 10-20 µm.

5. The pharmaceutical composition according to claim 1, wherein the amount of said lactose is in the range of 1-15%, by weight of the composition.

6. The pharmaceutical composition according to claim 1, wherein the amount of said course particle mannitol is in the range of 85-99% by weight of the composition.

7. The pharmaceutical composition claim 1, wherein said muscarinic receptor antagonist is selected from the group consisting of at least one or a mixture of tiotropium, glycopyronium, aclidinium, darotropium, oxitropium, and ipratropium.

8. The pharmaceutical composition according to claim 1, wherein said composition further comprises one or more β2-adrenergic agonists.

9. The pharmaceutical composition according to claim 8, wherein said one or more beta-2 adrenergic agonists are selected from at least one or a mixture of salmeterol, formoterol, arformoterol, salbutamol, indacaterol, terbutaline, metaproterenol, vilanterol, carmoterol, olodaterol, bambuterol, and clenbuterol.

10. The pharmaceutical composition according to claim 1, further comprising one or more corticosteroids selected from at least one or a mixture of ciclesonide, budesonide, fluticasone, aldosterone, beclomethasone, betametazone, chloprednol, cortisone, cortivasol, deoxycortone, desonide, desoxymethasone, dexamethasone, difluocortolone, fluchloralin, flumetasone, flunisolide, fluocinolone, fluocinonide, flurocortisone, fluocortolone, flurometolone, flurandrenolone, halcinonide, hydrocortisone, icometasone, meprednisone, methylprednisolone, mometasone, paramethasone, prednisolone, prednisone, tixocortole, and/or triamcinolone.

11. The pharmaceutical composition according to claim 10, wherein the one or more corticosteroids are selected from ciclesonide, budesonide, fluticasone, and mometasone.

12. The pharmaceutical composition according to claim 1, further comprising (a) one or more corticosteroids, (b) one or more β2-adrenergic agonists; or (c) one or more corticosteroids and one or more β2-adrenergic agonists.

13. The pharmaceutical composition according to claim 1, further comprising an excipient selected from at least one or a mixture of glucose, glucose anhydrous, trehalose, cellobiose, and sorbitol.

14. The pharmaceutical composition according to claim 1, wherein said composition comprises one of the following therapeutically active combinations:
   i. Aclidinium and tiotropium
   ii. Aclidinium and glycopyrronium
   iii. Aclidinium and darotropyum
   iv. Aclidinium and oxitropium
   v. Aclidinium and ipratropium
   vi. Aclidinium and ciclesonide
   vii. Aclidinium and budesonid
   viii. Aclidinium and fluticasone ix. Aclidinium and mometazon
x. Tiotropium and glycopyrronium
xi. Tiotropium and darotropyum
xii. Tiotropium and oxitropium
xiii. Tiotropium and ipratropium
xiv. Tiotropium and ciclesonide
xv. Tiotropium and budesonid
xvi. Tiotropium and fluticasone
xvii. Tiotropium and mometazon
xviii. Glycopyrronium and tiotropium
xix. Glycopyrronium and glycopyrronium
xx. Glycopyrronium and darotropyum
xxi. Glycopyrronium and oxitropium
xxii. Glycopyrronium and ipratropium
xxiii. Glycopyrronium and ciclesonide
xxiv. Glycopyrronium and budesonid
xxv. Glycopyrronium and fluticasone
xxvi. Glycopyrronium and mometazon
xxvii. Oxitropium and tiotropium
xxviii. Oxitropium and darotropyum
xxix. Oxitropium and aclidinium
xxx. Oxitropium and ipratropium
xxxi. Oxitropium and ciclesonide
xxxii. Oxitropium and budesonid
xxxiii. Oxitropium and fluticasone
xxxiv. Oxitropium and mometazon
xxxv. Darotropyum and tiotropium
xxxvi. Darotropyum and aclidinium
xxxvii. Darotropyum and oxitropium
xxxviii. Darotropyum and ipratropium
xxxix. Darotropyum and ciclesonide
xl. Darotropyum and budesonid
xli. Darotropyum and fluticasone
xlii. Darotropyum and mometazon
xliii. Aclidinium and salmeterol
xliv. Aclidinium and formoterol
xlv. Aclidinium and arformoterol
xlvi. Aclidinium and salbutamol
xlvii. Aclidinium and indacaterol
xlviii. Aclidinium and vilanterol
xlix. Aclidinium and carmoterol
l. Aclidinium and olodaterol
li. Aclidinium and bambuterol
lii. Tiotropium and salmeterol
liii. Tiotropium and formoterol
liv. Tiotropium and arformoterol
lv. Tiotropium and salbutamol
lvi. Tiotropium and indacaterol
lvii. Tiotropium and vilanterol
lviii. Tiotropium and carmoterol
lix. Tiotropium and olodaterol
lx. Tiotropium and bambuterol
lxi. Glycopyrronium and salmeterol
lxii. Glycopyrronium and formoterol
lxiii. Glycopyrronium and arformoterol
lxiv. Glycopyrronium and salbutamol
lxv. Glycopyrronium and indacaterol
lxvi. Glycopyrronium and vilanterol
lxvii. Glycopyrronium and carmoterol
lxviii. Glycopyrronium and olodaterol
lxix. Glycopyrronium and bambuterol
lxx. Oxitropium and salmeterol
lxxi. Oxitropium and formoterol
lxxii. Oxitropium and arformoterol
lxxiii. Oxitropium and salbutamol
lxxiv. Oxitropium and indacaterol
lxxv. Oxitropium and vilanterol
lxxvi. Oxitropium and carmoterol
lxxvii. Oxitropium and olodaterol
lxxviii. Oxitropium and bambuterol
lxxix. Darotropium and salmeterol
lxxx. Darotropium and formoterol
lxxxi. Darotropium and arformoterol
lxxxii. Darotropium and salbutamol
lxxxiii. Darotropium and indacaterol
lxxxiv. Darotropium and vilanterol
lxxxv. Darotropium and carmoterol
lxxxvi. Darotropium and olodaterol
lxxxvii. Darotropium and bambuterol
lxxxviii. Aclidinium, tiotropium and salmeterol
lxxxix. Aclidinium, tiotropium and formoterol
xc. Aclidinium, tiotropium and arformoterol
xci. Aclidinium, tiotropium and indacaterol
xcii. Aclidinium, tiotropium and olodaterol
xciii. Aclidinium, tiotropium and vilanterol
xciv. Aclidinium, tiotropium and carmoterol
xcv. Aclidinium, tiotropium and bambuterol
xcvi. Aclidinium, glycopyrronium and salmeterol
xcvii. Aclidinium, glycopyrronium and formoterol
xcviii. Aclidinium, glycopyrronium and arformoterol
xcix. Aclidinium, glycopyrronium and indacaterol
c. Aclidinium, glycopyrronium and olodaterol
ci. Aclidinium, glycopyrronium and vilanterol
cii. Aclidinium, glycopyrronium and carmoterol
ciii. Aclidinium, glycopyrronium and bambuterol
civ. Aclidinium, oxitropium and salmeterol
cv. Aclidinium, oxitropium and formoterol
cvi. Aclidinium, oxitropium and arformoterol
cvii. Aclidinium, oxitropium and indacaterol
cviii. Aclidinium, oxitropium and olodaterol
cix. Aclidinium, oxitropium and vilanterol
cx. Aclidinium, oxitropium and carmoterol
cxi. Aclidinium, oxitropium and bambuterol
cxii. Glycopyrronium, tiotropium and salmeterol
cxiii. Glycopyrronium, tiotropium and formoterol
cxiv. Glycopyrronium, tiotropium and arformoterol
cxv. Glycopyrronium, tiotropium and indacaterol
cxvi. Glycopyrronium, tiotropium and olodaterol
cxvii. Glycopyrronium, tiotropium and vilanterol
cxviii. Glycopyrronium, tiotropium and carmoterol
cxix. Glycopyrronium, tiotropium and bambuterol
cxx. Glycopyrronium, oxitropium and salmeterol
cxxi. Glycopyrronium, oxitropium and formoterol
cxxii. Glycopyrronium, oxitropium and arformoterol
cxxiii. Glycopyrronium, oxitropium and indacaterol
cxxiv. Glycopyrronium, oxitropium and olodaterol
cxxv. Glycopyrronium, oxitropium and vilanterol
cxxvi. Glycopyrronium, oxitropium and carmoterol
cxxvii. Glycopyrronium, oxitropium and bambuterol
cxxviii. Daratropium, tiotropium and salmeterol
cxxix. Daratropium, tiotropium and formoterol
cxxx. Daratropium, tiotropium and arformoterol
cxxxi. Daratropium, tiotropium and indacaterol
cxxxii. Daratropium, tiotropium and olodaterol
cxxxiii. Daratropium, tiotropium and vilanterol
cxxxiv. Daratropium, tiotropium and carmoterol
cxxxv. Daratropium, tiotropium and bambuterol
cxxxvi. Daratropium, glycopyrronium and salmeterol
cxxxvii. Daratropium, gikopironyum and formoterol
cxxxviii. Daratropium, glycopyrronium and arformoterol
cxxxix. Daratropium, glycopyrronium and indacaterol
cxl. Daratropium, glycopyrronium and olodaterol
cxli. Daratropium, glycopyrronium and vilanterol
cxlii. Daratropium, glycopyrronium and carmoterol cxliii. Daratropium, glycopyrronium and bambuterol
cxliv. Daratropium, aclidinium and salmeterol
cxlv. Daratropium, aclidinium and formoterol
cxlvi. Daratropium, aclidinium and arformoterol
cxlvii. Daratropium, aclidinium and indacaterol
cxlviii. Daratropium, aclidinium and olodaterol
cxlix. Daratropium, aclidinium and vilanterol
cl. Daratropium, aclidinium and carmoterol
cli. Daratropium, aclidinium and bambuterol
clii. Daratropium, oxitropium and salmeterol
cliii. Daratropium, oxitropium and formoterol
cliv. Daratropium, oxitropium and arformoterol
clv. Daratropium, oxitropium and indacaterol
clvi. Daratropium, oxitropium and olodaterol
clvii. Daratropium, oxitropium and vilanterol
clviii. Daratropium, oxitropium and carmoterol
clix. Daratropium, oxitropium and bambuterol
clx. İndacaterol, tiotropium and salmeterol
clxi. İndacaterol, tiotropium and formoterol
clxii. İndacaterol, tiotropium and arformoterol
clxiii. İndacaterol, tiotropium and olodaterol
clxiv. İndacaterol, tiotropium and vilanterol
clxv. İndacaterol, tiotropium and carmoterol
clxvi. İndacaterol, tiotropium and bambuterol
clxvii. İndacaterol, glycopyrronium and salmeterol
clxviii. İndacaterol, glycopyrronium and formoterol
clxix. İndacaterol, glycopyrronium and arformoterol
clxx. İndacaterol, glycopyrronium and olodaterol
clxxi. İndacaterol, glycopyrronium and vilanterol
clxxii. İndacaterol, glycopyrronium and carmoterol
clxxiii. İndacaterol, glycopyrronium and bambuterol
clxxiv. İndacaterol, aclidinium and salmeterol
clxxv. İndacaterol, aclidinium and formoterol
clxxvi. İndacaterol, aclidinium and arformoterol
clxxvii. İndacaterol, aclidinium and olodaterol
clxxviii. İndacaterol, aclidinium and vilanterol
clxxix. İndacaterol, aclidinium and carmoterol
clxxx. İndacaterol, aclidinium and bambuterol
clxxxi. İndacaterol, oxitropium and salmeterol
clxxxii. İndacaterol, oxitropium and formoterol
clxxxiii. İndacaterol, oxitropium and arformoterol
clxxxiv. İndacaterol, oxitropium and olodaterol
clxxxv. İndacaterol, oxitropium and vilanterol
clxxxvi. İndacaterol, oxitropium and carmoterol
clxxxvii. İndacaterol, oxitropium and bambuterol
clxxxviii. Vilanterol, tiotropium and salmeterol
clxxxix. Vilanterol, tiotropium and formoterol
cxc. Vilanterol, tiotropium and arformoterol
cxci. Vilanterol, tiotropium and indacaterol
cxcii. Vilanterol, tiotropium and olodaterol
cxciii. Vilanterol, tiotropium and carmoterol
cxciv. Vilanterol, tiotropium and bambuterol
cxcv. Vilanterol, glycopyrronium and salmeterol
cxcvi. Vilanterol, glycopyrronium and formoterol
cxcvii. Vilanterol, glycopyrronium and arformoterol
cxcviii. Vilanterol, glycopyrronium and indacaterol
cxcix. Vilanterol, glycopyrronium and olodaterol
cc. Vilanterol, glycopyrronium and carmoterol
cci. Vilanterol, glycopyrronium and bambuterol
ccii. Vilanterol, aclidinium and salmeterol
cciii. Vilanterol, aclidinium and formoterol
cciv. Vilanterol, aclidinium and arformoterol
ccv. Vilanterol, aclidinium and indacaterol
ccvi. Vilanterol, aclidinium and olodaterol
ccvii. Vilanterol, aclidinium and carmoterol
ccviii. Vilanterol, aclidinium and bambuterol
ccix. Vilanterol, oxitropium and salmeterol
ccx. Vilanterol, oxitropium and formoterol
ccxi. Vilanterol, oxitropium and arformoterol
ccxii. Vilanterol, oxitropium and indacaterol
ccxiii. Vilanterol, oxitropium and olodaterol
ccxiv. Vilanterol, oxitropium and carmoterol
ccxv. Vilanterol, oxitropium and bambuterol
ccxvi. Carmoterol, tiotropium and salmeterol
ccxvii. Carmoterol, tiotropium and formoterol
ccxviii. Carmoterol, tiotropium and arformoterol
ccxix. Carmoterol, tiotropium and indacaterol
ccxx. Carmoterol, tiotropium and olodaterol
ccxxi. Carmoterol, tiotropium and vilanterol
ccxxii. Carmoterol, tiotropium and bambuterol
ccxxiii. Carmoterol, glycopyrronium and salmeterol
ccxxiv. Carmoterol, glycopyrronium and formoterol
ccxxv. Carmoterol, glycopyrronium and arformoterol
ccxxvi. Carmoterol, glycopyrronium and indacaterol
ccxxvii. Carmoterol, glycopyrronium and olodaterol
ccxxviii. Carmoterol, glycopyrronium and vilanterol
ccxxix. Carmoterol, glycopyrronium and bambuterol
ccxxx. Carmoterol, aclidinium and salmeterol
ccxxxi. Carmoterol, aclidinium and formoterol
ccxxxii. Carmoterol, aclidinium and arformoterol
ccxxxiii. Carmoterol, aclidinium and indacaterol
ccxxxiv. Carmoterol, aclidinium and olodaterol
ccxxxv. Carmoterol, aclidinium and vilanterol
ccxxxvi. Carmoterol, aclidinium and bambuterol
ccxxxvii. Carmoterol, oxitropium and salmeterol
ccxxxviii. Carmoterol, oxitropium and formoterol
ccxxxix. Carmoterol, oxitropium and arformoterol
ccxl. Carmoterol, oxitropium and indacaterol
ccxli. Carmoterol, oxitropium and olodaterol
ccxlii. Carmoterol, oxitropium and vilanterol
ccxliii. Carmoterol, oxitropium and bambuterol
ccxliv. Olodaterol, tiotropium and salmeterol
ccxlv. Olodaterol, tiotropium and formoterol
ccxlvi. Olodaterol, tiotropium and arformoterol
ccxlvii. Olodaterol, tiotropium and indacaterol
ccxlviii. Olodaterol, tiotropium and vilanterol
ccxlix. Olodaterol, tiotropium and bambuterol
ccl. Olodaterol, glycopyrronium and salmeterol
ccli. Olodaterol, glycopyrronium and formoterol
cclii. Olodaterol, glycopyrronium and arformoterol
ccliii. Olodaterol, glycopyrronium and indacaterol
ccliv. Olodaterol, glycopyrronium and vilanterol
cclv. Olodaterol, glycopyrronium and bambuterol
cclvi. Olodaterol, aclidinium and salmeterol
cclvii. Olodaterol, aclidinium and formoterol
cclviii. Olodaterol, aclidinium and arformoterol
cclix. Olodaterol, aclidinium and indacaterol
cclx. Olodaterol, aclidinium and vilanterol
cclxi. Olodaterol, aclidinium and bambuterol
cclxii. Olodaterol, oxitropium and salmeterol
cclxiii. Olodaterol, oxitropium and formoterol
cclxiv. Olodaterol, oxitropium and arformoterol
cclxv. Olodaterol, oxitropium and indacaterol
cclxvi. Olodaterol, oxitropium and vilanterol
cclxvii. Olodaterol, oxitropium and bambuterol wherein each of the above therapeutic agents can be present as a pharmaceutically acceptable salt or ester thereof, or in enantiomerically pure form or as a racemic mixture.

15. The pharmaceutical composition according to claim 1, wherein said composition comprises a blister having air and moisture barrier property, enabling simultaneous, respective and synchronic application.

16. The pharmaceutical composition according to claim 1, wherein said composition comprises a blister having air and moisture tightness property, enabling simultaneous, respective and synchronic application.

17. The pharmaceutical composition according to claim 1, wherein said composition comprises a dry powder inhaler device suitable for simultaneous, respective and synchronic application in a blister and having at least one locking mechanism ensuring the device to be maintained locked in both of the positions in which it is ready for inhalation and its lid is closed and ensuring the device to be automatically re-set once the lid is closed.

18. The pharmaceutical composition according to claim 1, wherein said composition comprises a dry powder inhaler device suitable for simultaneous, respective and synchronic application in a capsule.

19. The pharmaceutical composition according to claim 1, wherein the amount of said fine particle lactose is in the range of 1-10% by weight of said composition.

20. The pharmaceutical composition according to claim 1, wherein the amount of said course particle mannitol is in the range of 90-99% by weight of the composition.

21. The pharmaceutical composition according to claim 1, wherein said coarse particle mannitol has a (d10) particle size of 10-50 μm.

22. The pharmaceutical composition according to claim 21, wherein said fine particle lactose has a (d10) particle size of 1-4 μm.

23. The pharmaceutical composition according to claim 21, wherein said fine particle lactose has a (d90) particle size of 7-15 μm.

24. The pharmaceutical composition according to claim 21, wherein said fine particle lactose has a (d10) particle size of 1-4 μm and a (d90) particle size of 7-15 μm.

25. The pharmaceutical composition according to claim 1, further comprising coarse particle lactose with a (d50) particle size of 50-120 μm.

26. The pharmaceutical composition according to claim 1, further comprising coarse particle lactose with a (d50) particle size of 50-120 μm and a (d10) particle size of 10-50 μm.

27. The pharmaceutical composition according to claim 1, further comprising coarse particle lactose with a (d50) particle size of 50-120 μm and a (d90) particle size of 120-300 μm.

28. The pharmaceutical composition according to claim 1, further comprising fine particle mannitol with a (d50) particle size of 4-10 μm.

29. The pharmaceutical composition according to claim 1, further comprising fine particle mannitol with a (d50) particle size of 4-10 μm and a (d10) particle size of 1-5 μm.

30. The pharmaceutical composition according to claim 1, further comprising fine particle mannitol with a (d50) particle size of 4-10 μm and a (d90) particle size of 7-20 μm.

31. The pharmaceutical composition according to claim 1, wherein the coarse particle mannitol has a (d50) particle size of 50-75 μm.

32. The pharmaceutical composition according to claim 1, wherein the coarse particle mannitol has a (d90) particle size of 75-250 μm.

33. The pharmaceutical composition according to claim 1, wherein a ratio of the (d50) particle size to the (d90) particle size equals to 0.40 or greater for the coarse particle mannitol.

34. The pharmaceutical composition according to claim 33, wherein the mannitol is spray-dried mannitol.

35. The pharmaceutical composition according to claim 1, wherein a ratio of the (d50) particle size to the (d90) particle size is between 0.45 and 0.50 for the coarse particle mannitol.

36. The pharmaceutical composition according to claim 1, wherein a ratio of the (d50) particle size to the (d90) particle size is between 0.50 and 0.70 for the coarse particle mannitol.

37. A dry powder inhalation composition comprising,
at least one muscarinic receptor antagonist or a pharmaceutically acceptable salt thereof, fine particle lactose in the amount of 1-20% by weight of said composition and having a (d50) particle size in the range of 4-10 μm and coarse particle mannitol in the amount of 80-99% by weight of said composition and having a (d50) particle size in the range of 50-120 μm, wherein said fine particle lactose has a (d10) particle size of 1-5 μm.

38. A dry powder inhalation composition comprising,
at least one muscarinic receptor antagonist or a pharmaceutically acceptable salt thereof, fine particle lactose in the amount of 1-20% by weight of said composition and having a (d50) particle size in the range of 4-10 μm and coarse particle mannitol in the amount of 80-99% by weight of said composition and having a (d50) particle size in the range of 50-120 μm, wherein said fine particle lactose has a (d90) particle size of 7-20 μm.

39. A dry powder inhalation composition comprising,
(a) at least one muscarinic receptor antagonist or a pharmaceutically acceptable salt thereof;
(b) fine particle lactose in the amount of 1-20% by weight of said composition and having a (d50) particle size in the range of 4-10 μm; and
(c) coarse particle mannitol in the amount of 80-99% by weight of said composition and having a (d50) particle size in the range of 50-120 μm and a (d10) particle size of 10-50 μm.

40. The pharmaceutical composition according to claim 39, wherein the fine particle lactose has a (d50) particle size of 4-7 μm.

41. The pharmaceutical composition according to claim 39, wherein the fine particle lactose has a (d50) particle size of 4-7 μm and a d(10) particle size of 1-4 μm.

42. The pharmaceutical composition according to claim 39, wherein the fine particle lactose has a (d50) particle size of 4-7 μm and a d(90) particle size of 7-15 μm.

43. The pharmaceutical composition according to claim 39, wherein the fine particle lactose has a (d50) particle size of 4-7 μm, a d(10) particle size of 1-4 μm, and a d(90) particle size of 7-15 μm.

44. A method of treating chronic obstructive pulmonary disease in a mammalian subject, comprising administering to the subject a pharmaceutical composition according to claim 1.

45. The method according to claim 44, wherein a pharmaceutically acceptable amount of said composition is administered once a day or twice a day.

46. A method of treating asthma in a mammalian subject, comprising administering to the subject a pharmaceutical composition according to claim 1.

47. The method according to claim 46, wherein a pharmaceutically acceptable amount of said composition is administered once a day or twice a day.

* * * * *